(12) United States Patent
Knudsen

(10) Patent No.: US 11,421,284 B2
(45) Date of Patent: *Aug. 23, 2022

(54) METHODS FOR PREDICTING DRUG RESPONSIVENESS IN CANCER PATIENTS

(71) Applicant: Oncology Venture ApS, Hørsholm (DK)

(72) Inventor: Steen Knudsen, Scottsdale, AZ (US)

(73) Assignee: Allarity Therapeutics Europe ApS, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/927,725

(22) Filed: Jul. 13, 2020

(65) Prior Publication Data

US 2020/0340067 A1    Oct. 29, 2020

Related U.S. Application Data

(63) Continuation of application No. 15/647,464, filed on Jul. 12, 2017, now abandoned, which is a continuation of application No. 15/289,026, filed on Oct. 7, 2016, now Pat. No. 9,725,769.

(51) Int. Cl.
| | |
|---|---|
| *C12Q 1/68* | (2018.01) |
| *C12Q 1/6886* | (2018.01) |
| *A61K 31/122* | (2006.01) |
| *A61K 45/06* | (2006.01) |
| *A61K 9/00* | (2006.01) |

(52) U.S. Cl.
CPC .......... *C12Q 1/6886* (2013.01); *A61K 9/0019* (2013.01); *A61K 31/122* (2013.01); *A61K 45/06* (2013.01); *C12Q 2600/106* (2013.01); *C12Q 2600/158* (2013.01)

(58) Field of Classification Search
CPC ........................................................ C12Q 1/68
USPC ........................................................... 435/6.1
See application file for complete search history.

(56) References Cited

U.S. PATENT DOCUMENTS

| | | | |
|---|---|---|---|
| 6,911,306 | B1 | 6/2005 | Vertino |
| 7,239,986 | B2 | 7/2007 | Golub et al. |
| 7,709,616 | B2 | 5/2010 | Bentwich et al. |
| 8,445,198 | B2 | 5/2013 | Knudsen |
| 9,598,734 | B2 | 3/2017 | Knudsen |
| 9,725,769 | B1 | 8/2017 | Knudsen |

(Continued)

FOREIGN PATENT DOCUMENTS

| | | |
|---|---|---|
| CA | 2428112 A1 | 11/2003 |
| CN | 102002490 A | 4/2011 |

(Continued)

OTHER PUBLICATIONS

Koeppel et al., Irofulven cytotoxicity depends on transcription-coupled nucleotide excision repair and is correlated with XPG expression in solid tumor cells, Clin Cancer Res. Aug. 15, 2004;10(16):5604-13.*

(Continued)

*Primary Examiner* — Aaron A Priest
(74) *Attorney, Agent, or Firm* — Clark & Elbing LLP

(57) ABSTRACT

The present invention features methods, devices, and kits for detecting expression in a patient having cancer or determining responsive of a patient having cancer to a treatment, such as irofulven. The invention further includes methods of treating a patient having cancer by administering, e.g., irofulven.

20 Claims, 1 Drawing Sheet

Specification includes a Sequence Listing.

(56) References Cited

U.S. PATENT DOCUMENTS

| | | |
|---|---|---|
| 2001/0051344 A1 | 12/2001 | Shalon et al. |
| 2002/0164663 A1 | 11/2002 | Fuqua et al. |
| 2003/0017481 A1 | 1/2003 | Golub et al. |
| 2003/0073083 A1 | 4/2003 | Tamayo et al. |
| 2004/0018525 A1 | 1/2004 | Wirtz et al. |
| 2004/0072722 A1 | 4/2004 | Kornblith et al. |
| 2005/0176669 A1 | 8/2005 | Al-Murrani |
| 2005/0260586 A1 | 11/2005 | Demuth et al. |
| 2005/0260646 A1 | 11/2005 | Baker et al. |
| 2006/0105360 A1 | 5/2006 | Croce et al. |
| 2006/0121511 A1 | 6/2006 | Lee et al. |
| 2007/0172844 A1 | 7/2007 | Lancaster et al. |
| 2008/0227663 A1 | 9/2008 | Tisone et al. |
| 2008/0306006 A1 | 12/2008 | Croce et al. |
| 2009/0023149 A1 | 1/2009 | Knudsen |
| 2009/0221435 A1 | 9/2009 | Baskerville et al. |
| 2009/0239223 A1 | 9/2009 | Gehrmann et al. |
| 2010/0240043 A1 | 9/2010 | Rotter et al. |
| 2011/0123990 A1 | 5/2011 | Baker et al. |
| 2012/0046186 A1 | 2/2012 | Pelham et al. |
| 2012/0177726 A1 | 7/2012 | Petersen et al. |
| 2012/0214703 A1 | 8/2012 | Croce et al. |
| 2012/0302626 A1 | 11/2012 | Dave et al. |
| 2013/0053275 A1 | 2/2013 | Knudsen |
| 2013/0059015 A1 | 3/2013 | Lancaster et al. |
| 2014/0148354 A1* | 5/2014 | Campana .......... C12Q 1/6886 506/9 |
| 2014/0236495 A1* | 8/2014 | Thiery ............... C12Q 1/6886 506/17 |
| 2014/0294730 A1 | 10/2014 | Slack-Davis et al. |
| 2015/0353928 A1 | 12/2015 | Weiner |
| 2016/0199399 A1 | 7/2016 | Knudsen |
| 2017/0283884 A1 | 10/2017 | Knudsen |
| 2018/0087113 A1 | 3/2018 | Knudsen |
| 2018/0100197 A1 | 4/2018 | Knudsen |
| 2018/0202004 A1 | 7/2018 | Knudsen |

FOREIGN PATENT DOCUMENTS

| | | |
|---|---|---|
| EP | 1550731 A1 | 7/2005 |
| EP | 2081950 B1 | 3/2013 |
| JP | 2004-43446 A | 2/2004 |
| RU | 2528247 C2 | 9/2014 |
| WO | WO-00/26247 A2 | 5/2000 |
| WO | WO-00/31930 A1 | 6/2000 |
| WO | WO-00/35473 A2 | 6/2000 |
| WO | WO-03/082078 A2 | 10/2003 |
| WO | WO-03/097052 A2 | 11/2003 |
| WO | WO-2005/005601 A2 | 1/2005 |
| WO | WO-2005/014856 A1 | 2/2005 |
| WO | WO-2005/047534 A2 | 5/2005 |
| WO | WO-2005/066371 A2 | 7/2005 |
| WO | WO-2005/087948 A2 | 9/2005 |
| WO | WO-2005/094863 A1 | 10/2005 |
| WO | WO-2005/100606 A2 | 10/2005 |
| WO | WO-2007/072225 A2 | 6/2007 |
| WO | WO-2008/073177 A2 | 6/2008 |
| WO | WO-2008/073629 A2 | 6/2008 |
| WO | WO-2008/112283 A2 | 9/2008 |
| WO | WO-2008/138578 A2 | 11/2008 |
| WO | WO-2009/036332 A1 | 3/2009 |
| WO | WO-2009/080437 A1 | 7/2009 |
| WO | WO-2009/141450 A2 | 11/2009 |
| WO | WO-2011/032563 A1 | 3/2011 |
| WO | WO-2011/047689 A2 | 4/2011 |
| WO | WO-2011/098578 A2 | 8/2011 |
| WO | WO-2011/135459 A2 | 11/2011 |
| WO | WO-2012/024543 A1 | 2/2012 |
| WO | WO-2012/106718 A2 | 8/2012 |
| WO | WO-2012/109233 A2 | 8/2012 |
| WO | WO-2012/163541 A1 | 12/2012 |
| WO | WO-2013/130465 A2 | 9/2013 |
| WO | WO-2014/195032 A1 | 12/2014 |
| WO | WO-2015135035 A2 * | 9/2015 ......... C07K 16/2818 |

OTHER PUBLICATIONS

Woynarowska et al., Changes in prostate-specific antigen (PSA) level correlate with growth inhibition of prostate cancer cells treated in vitro with a novel anticancer drug, irofulven, Invest New Drugs. 2001;19(4):283-91.*

Senzer et al., Irofulven demonstrates clinical activity against metastatic hormone-refractory prostate cancer in a phase 2 single-agent trial, Am J Clin Oncol. Feb. 2005;28(1):36-42.*

Liang et al., Caspase-mediated apoptosis and caspase-independent cell death induced by irofulven in prostate cancer cells, Mol Cancer Ther. Nov. 2004;3(11):1385-96.*

"Oncology Venture presents LiPlaCis on AACR in New Orleans," Press release issued by Oncology Venture Sweden AB, Hoersholm, Denmark, Mar. 4, 2016 (2 pages).

Abba et al., "Gene expression signature of estrogen receptor alpha status in breast cancer," BMC Genomics. 6:37 (2005) (13 pages).

Affymetrix Expression Probeset Details for HG-U133_PLUS_2:209083_AT, <https://www.affymetrix.com/analysis/netaffx/fullrecord.affx?pk=HG-U133_PLUS_2:209083_AT>, retrieved Nov. 27, 2018 (4 pages).

Agrawal et al., "Long-term effect of fulvestrant on hormone receptors and proliferation marker in breast cancer," EJC Supplements. 8(3):111 (2010).

Arienti et al., "Activity of lipoplatin in tumor and in normal cells in vitro," Anti-Cancer Drugs. 19(10):983-990 (2008) (8 pages).

Baker, "The central role of receiver operating characteristic (ROC) curves in evaluating tests for the early detection of cancer," J Natl Cancer Inst. 95(7):511-5 (2003).

Bild et al., "Oncogenic pathway signatures in human cancers as a guide to targeted therapies," Nature. 439(7074):353-7 (2006).

Boulikas, "Clinical overview on Lipoplatin™: a successful liposomal formulation of cisplatin," Expert Opin Investig Drugs. 18(8):1197-218 (2009) (23 pages).

Buhl et al., "A genetic response profile to predict efficacy of adjuvant 5-FU in colon cancer," Ann Oncol. 25(Suppl. 4):iv167-209 (2014) (1 page).

Canadian Examination Report for Canadian Patent Application No. 2,631,236, dated Mar. 19, 2015 (6 pages).

Casagrande et al., "Preclinical Activity of the Liposomal Cisplatin Lipoplatin in Ovarian Cancer," Clin Cancer Res. 20(21):5496-5506 (2014).

Castelli et al., "In silico analysis of microRNAS targeting the HLA-G 3' untranslated region alleles and haplotypes," Hum Immunol. 70(12):1020-5 (2009).

Chow et al., "Increased expression of annexin I is associated with drug-resistance in nasopharyngeal carcinoma and other solid tumors," Proteomics Clin Appl. 3(6):654-62 (2009).

Dahlén et al., "Activation of the GLI oncogene through fusion with the beta-actin gene (ACTB) in a group of distinctive pericytic neoplasms: pericytoma with t(7;12)," Am J Pathol. 164(5):1645-53 (2004).

De Jonge et al., "Early cessation of the clinical development of LiPlaCis, a liposomal cisplatin formulation," Eur J Cancer. 46(16):3016-3021 (2010) (6 pages).

Decision of Rejection for Japanese Application No. 2008-542865, dated Oct. 21, 2013 (11 pages).

Decision on Rejection for Chinese Application No. 200680052220.2, dated Jun. 5, 2013 (8 pages).

Di Lisio, "MicroRNA expression in B-cell lymphomas," Doctoral Thesis, Facultad de Ciencias, Departamento de Biología Molecular, Universidad Autónoma de Madrid (2012) (223 pages).

Elstrom et al., "Response to second-line therapy defines the potential for cure in patients with recurrent diffuse large B-cell lymphoma: implications for the development of novel therapeutic strategies," Clin Lymphoma Myeloma Leuk. 10(3):192-6 (2010).

Etter et al., "The combination of chemotherapy and intraperitoneal MegaFas Ligand improves treatment of ovarian carcinoma," Gynecol Oncol. 107(1):14-21 (2007).

Fournier et al., "Gene expression signature in organized and growth-arrested mammary acini predicts good outcome in breast cancer," Cancer Res. 66(14):7095-7102 (2006).

(56) References Cited

OTHER PUBLICATIONS

Friis-Hansen et al., "Mir-449 inhibits growth of gastric cancer cells partly by inhibiting the expression of met and amphiregulin," Gastroenterology. 136(5):A-165 (2009) (1 page).

Fumagalli et al., "Oral vinorelbine and capecitabine plus bevacizumab in recurrent inflammatory breast cancer: gene profiling and response to treatment," Thirty-Third Annual CTRC-AACR San Antonio Breast Cancer Symposium, Dec. 8-12, San Antonio, TX. Cancer Res. 70(24 Suppl.): Abstract P6-12-06 (2010) (4 pages).

Gallardo et al., "miR-34a as a prognostic marker of relapse in surgically resected non-small-cell lung cancer," Carcinogenesis. 30(11):1903-9 (2009).

Genbank Accession No. AY889152.1. Retrieved on Mar. 5, 2013 (2 pages).

GenBank Accession No. HC040507.1: Sequence 486 from Patent EP2112235, 2009 (1 page).

Gerspach et al., "Therapeutic Targeting of CD95 and the TRAIL Death Receptors," Recent Pat Anticancer Drug Discov. 6(3):294-310 (2011).

Grimm et al., "Drugs interfering with apoptosis in breast cancer," Curr Pharm Des. 17(3):272-83 (2011).

Juncker-Jensen et al., "Insulin-like growth factor binding protein 2 is a marker for antiestrogen resistant human breast cancer cell lines but is not a major growth regulator," Growth Horm IGF Res. 16(4):224-39 (2006).

Knudsen et al., "Development and validation of a gene expression score that predicts response to fulvestrant in breast cancer patients," PLoS One. 9(2):e87415 (2014) (12 pages).

Koeppel et al., "Irofulven cytotoxicity depends on transcription-coupled nucleotide excision repair and is correlated with XPG expression in solid tumor cells," Clin Cancer Res. 10(16):5604-13 (2004) (11 pages).

Kornmann et al., "Thymidylate synthase and dihydropyrimidine dehydrogenase mRNA expression levels: predictors for survival in colorectal cancer patients receiving adjuvant 5-fluorouracil," Clinical Cancer Res. 9(11):4116-24 (2003).

Kuter et al., "Dose-dependent change in biomarkers during neoadjuvant endocrine therapy with fulvestrant: results from NEWEST, a randomized Phase II study," Breast Cancer Res Treat. 133(1):237-46 (2012).

Lee et al., "Cancer pharmacogenomics: powerful tools in cancer chemotherapy and drug development," Oncologist. 10(2):104-11 (2005) (9 pages).

Li et al., "Intronic microRNA: discovery and biological implications," DNA Cell Biol. 26(4):195-207 (2007).

Li et al., "Selection of optimal oligonucleotide probes for microarrays using multiple criteria, global alignment and parameter estimation," Nucleic Acids Res. 33(19):6114-23 (2005).

Liang et al., "Caspase-mediated apoptosis and caspase-independent cell death induced by irofulven in prostate cancer cells," Mol Cancer Ther. 3(11):1385-96 (2004) (13 pages).

Liang et al., "Characterization of microRNA expression profiles in normal human tissues," BMC Genomics. 8(166): (2007) (20 pages).

Liu et al., "Roles of USF, Ikaros and Sp proteins in the transcriptional regulation of the human reduced folate carrier B promoter," Biochem J. 383(Pt 2):249-57 (2004).

López et al., Chapter 11: MicroRNAs in Lymphoma, *MicroRNAs in Cancer Translational Research*. W.C.S. Cho (ed.), 239-67 (2011).

McCune et al., "Prognosis of hormone-dependent breast cancers: implications of the presence of dysfunctional transcriptional networks activated by insulin via the immune transcription factor T-bet," Cancer Res. 70(2):685-96 (2010).

Medinger et al., "Gene-expression Profiling in Patients with Plasma Cell Myeloma Treated with Novel Agents," Cancer Genomics Proteomics. 13(4):275-9 (2016).

Michels, "The promises and challenges of epigenetic epidemiology," Exp Gerontol. 45(4):297-301 (2010).

Mizutani et al., "Significance of orotate phosphoribosyltransferase activity in renal cell carcinoma," J Urol. 171(2 Pt 1):605-10 (2004).

Nair et al., "A simple practice guide for dose conversion between animals and human," J Basic Clin Pharm. 7(2):27-31 (2016).

Nakamura et al., "Search of a group of genes involved with sensitivity to anticancer agent Cisplatin (CDDP) using cDNA microarray," Chiba Med J. 80(2):88 (2004) (2 pages).

Narita et al., "Lower expression of activating transcription factors 3 and 4 correlates with shorter progression-free survival in multiple myeloma patients receiving bortezomib plus dexamethasone therapy," Blood Cancer J. 5:e373 (2015) (8 pages).

NCode™ Multi-Species miRNA Microarray Probe Set, Version 2.0 (Cat. # MIRMPS2-01), retrieved from <http://www.invitrogen.com/site/us/en/home/Products-and-Services/Applications/epigenetics-noncoding-rna-research/miRNA-Profiling-/miRNA-Probe-Set-Files.html> (2009) (21 pages).

Nielsen et al., "Design of oligonucleotides for microarrays and perspectives for design of multi-transcriptome arrays," Nucleic Acids Res. 31(13):3491-6 (2003).

NIH DailyMed for Fluorouracil Injection, USP, revised May 2010, retrieved Jan. 29, 2019 (2010) (8 pages).

Nikas et al., "Prognosis of treatment response (pathological complete response) in breast cancer," Biomark Insights. 7:59-70 (2012).

Ocio et al., "The Activation of Fas Receptor by APO010, a Recombinant Form of Fas Ligand, Induces In Vitro and In Vivo Antimyeloma Activity," Blood. 110(11):1515 (2007) (4 pages) (Abstract Only).

Okumura et al., "Correlation between chemosensitivity and mRNA expression level of 5-fluorouracil-related metabolic enzymes during liver metastasis of colorectal cancer," Oncol Rep. 15(4):875-82 (2006).

Ooyama et al., "Gene expression analysis using human cancer xenografts to identify novel predictive marker genes for the efficacy of 5-fluorouracil-based drugs," Cancer Sci. 97(6):510-22 (2006).

Paul et al., "Impact of miRNA deregulation on mRNA expression profiles in response to environmental toxicant, nonylphenol," Mol Cell Toxicol. 7:259-69 (2011).

Pourhassan et al., "Revisiting the use of sPLA$_2$-sensitive liposomes in cancer therapy," J Control Release. 261:163-173 (2017).

Pradervand et al., "Concordance among digital gene expression, microarrays, and qPCR when measuring differential expression of microRNAs," Biotechniques. 48(3):219-222 (2010).

Pre-Appeal Examination Report for Japanese Application No. 2008-542865, dated Mar. 27, 2014 (6 pages).

Questioning for Japanese Application No. 2008-542865, dated Aug. 11, 2014 (8 pages).

Reid et al., "Circulating microRNAs: Association with disease and potential use as biomarkers," Grit Rev Oncol Hematol. 80(2):193-208 (2011).

Rouillard et al., "OligoArray 2.0: design of oligonucleotide probes for DNA microarrays using a thermodynamic approach," Nucleic Acids Res. 31(12):3057-62 (2003).

Senzer et al., "Irofulven demonstrates clinical activity against metastatic hormone-refractory prostate cancer in a phase 2 single-agent trial," Am J Clin Oncol. 28(1):36-42 (2005).

Sezaki et al., "Over-expression of the dominant-negative isoform of Ikaros confers resistance to dexamethasone-induced and anti-IgM-induced apoptosis," Br J Haematol. 121(1):165-9 (2003) (Abstract only).

Slonim, "From patterns to pathways: gene expression data analysis comes of age," Nat Genet. 32 Suppl:502-8 (2002).

Suresh et al., "Resistance/response molecular signature for oral tongue squamous cell carcinoma," Dis Markers. 32(1):51-64 (2012).

The Japanese Journal of Urology, 94(2):159 (APP-105) (2003).

Van't Veer et al., "Gene expression profiling predicts clinical outcome of breast cancer," Nature. 415(6871):530-6 (2002).

Vangsted et al., "APO010 sensitivity in relapsed multiple myeloma patients," Annals of Oncol. 27(Supplement 6): vi15-vi42 (2016) (2 pages) (Abstract only).

Verbrugge et al., "Combining radiotherapy with APO010 in cancer treatment," Clin Cancer Res. 15(6):2031-8 (2009) (9 pages).

Wang et al., "Independent Validation of a Model Using Cell Line Chemosensitivity to Predict Response to Therapy," J Natl Cancer Inst. 105(17): 1284-91 (2013).

(56) References Cited

OTHER PUBLICATIONS

Woynarowska et al., "Changes in prostate-specific antigen (PSA) level correlate with growth inhibition of prostate cancer cells treated in vitro with a novel anticancer drug, irofulven," Invest New Drugs. 19(4):283-91 (2001).

Xu et al., "[Association of miRNAs expression profiles with prognosis and relapse in childhood acute lymphoblastic leukemia]," Zhonghua Xue Ye Xue Za Zhi. 32(3):178-81 (Abstract only) (2011).

Yang et al., "The role of microRNA in human lung squamous cell carcinoma," Cancer Genet Cytogenet. 200(2):127-33 (2010).

Yin, "Screening of laryngeal carcinoma multidrug resistance-associated genes and study on reversion by Chinese herbs," China Doctoral Dissertations Full-text Database, Division of Medical and Hygiene Technology. 8:E072-85 (2010) (3 pages) (Abstract only).

Zhang et al., "MicroRNA-650 targets ING4 to promote gastric cancer tumorigenicity," Biochem Biophys Res Commun. 395(2):275-280 (2010).

\* cited by examiner

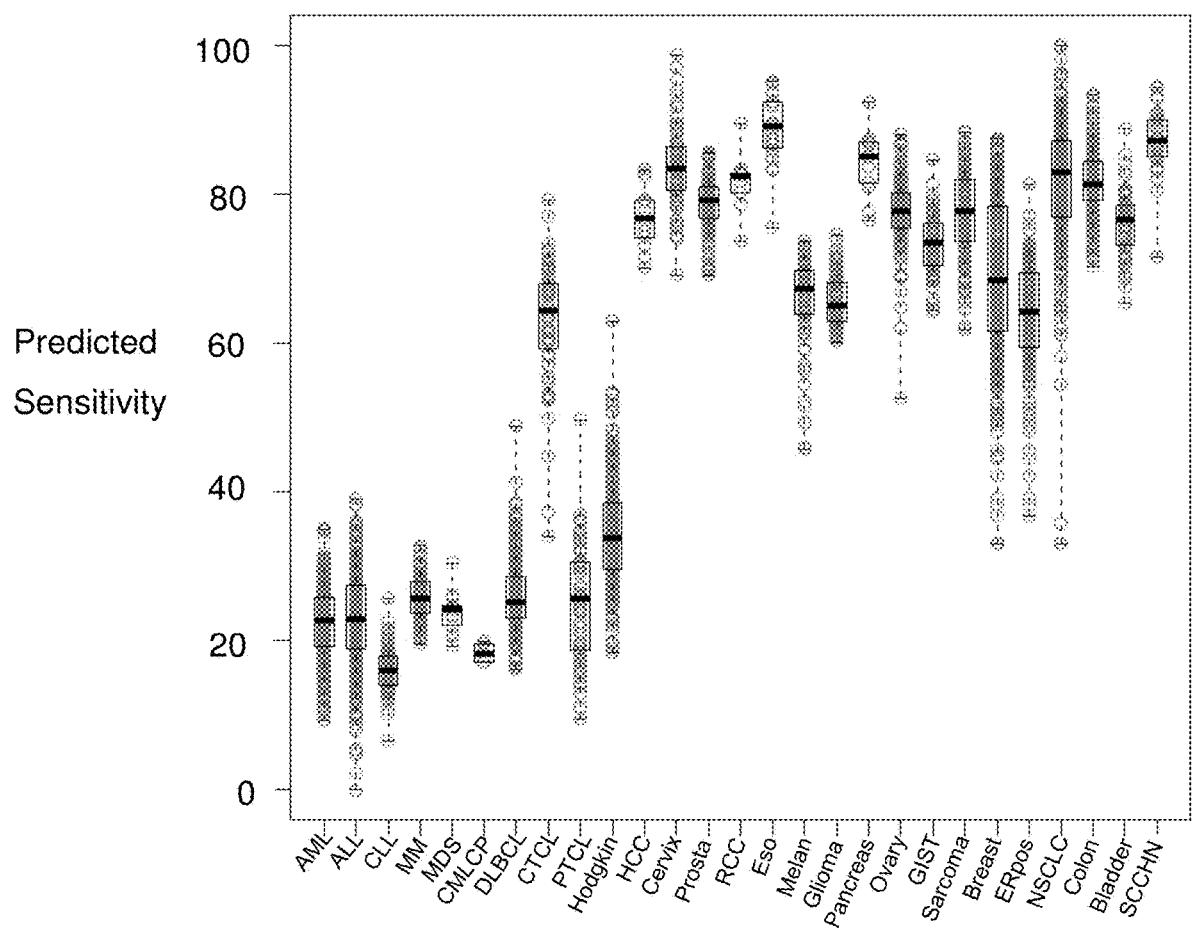

METHODS FOR PREDICTING DRUG RESPONSIVENESS IN CANCER PATIENTS

FIELD OF THE INVENTION

The invention features methods to detect the expression levels of genes encoding biomarkers in cancer patients and to predict the responsiveness of cancer patients to irofulven.

BACKGROUND

DNA microarrays have been used to measure gene expression in samples from patients and to facilitate diagnosis of disease. Gene expression can reveal the presence of cancer in a patient in addition to the type, stage, and origin of the cancer. Gene expression may even have a role in predicting the efficacy of cancer therapies. In recent decades, the National Cancer Institute (NCI) has tested cancer therapeutics for their effect in limiting the growth of 60 human cancer cell lines. The NCI has also measured gene expression in those 60 cancer cell lines using DNA microarrays. Various studies have explored the relationship between gene expression and therapeutic effect using the NCI datasets.

During cancer treatment, critical time is often lost due to a trial and error approach to finding an effective therapy. In addition, cancer cells often develop resistance to a previously effective therapy. In such situations, patient outcome would be greatly improved by early detection of such resistance.

Thus, there exists a need in the art for methods and devices that can predict the responsiveness of cancer patients to a medical treatment.

SUMMARY OF THE INVENTION

The invention features methods for detecting expression of a biomarker (e.g., one, two, three, four, five, ten, twenty, or all of the biomarkers shown in Tables 1-4, such as ATP1B1 (SEQ ID NO: 201)) in a patient having cancer, such as a patient having cancer (e.g., a human) that is resistant to one or more cancer therapies other than irofulven (e.g., a patient with prostate cancer, ovarian cancer, or hepatocellular carcinoma (HCC) that is resistant to one or more cancer therapies other than irofulven), and for determining responsiveness of a cancer patient (e.g., a patient with prostate cancer, ovarian cancer, or HCC) to treatment with irofulven. The invention also features methods of treating cancer in a patient in need thereof (e.g., a patient with prostate cancer, ovarian cancer, or HCC or a treatment resistant form thereof) that include administering irofulven to the patient, in which the patient is or has been determined to be responsive to irofulven according to the diagnostic methods described herein.

Exemplary types of cancer that can be diagnosed or treated with the methods include, e.g., prostate cancer, ovarian cancer (e.g., ovarian adenocarcinoma or embryonal carcinoma), liver cancer (e.g., HCC or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma, and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, or neoplasms of the central nervous system. For example, the cancer may be a solid tumor or a hematological cancer.

A first aspect of the invention features a method for detecting expression of a biomarker (e.g., one, two, three, four, five, ten, twenty, or all of the biomarkers shown in Tables 1 and/or 2, such as ATP1B1 (SEQ ID NO: 201)) in a patient having cancer (e.g., prostate cancer, ovarian cancer, or HCC), such as a patient having cancer that is resistant to one or more cancer therapies other than irofulven (e.g., a patient with prostate cancer, ovarian cancer, or HCC that is resistant to one or more cancer therapies other than irofulven). The method includes (a) contacting a sample (e.g., a tumor sample) from the patient including one or more nucleic acid molecules with a device (e.g., a microarray) including: i) one or more single-stranded nucleic acid molecules capable of specifically hybridizing with the nucleotides of one or more biomarkers of sensitivity selected from the biomarkers of Tables 1 and 3 (e.g., ATP1B1 (SEQ ID NO: 201)); and/or ii) one or more single-stranded nucleic acid molecules capable of specifically hybridizing with the nucleotides of one or more biomarkers of resistance selected from the biomarkers of Tables 2 and 4 (e.g., IGLC1 (SEQ ID NO: 301, 302, 303, or 318)); and (b) detecting a level of expression of one or more of the biomarker(s) of sensitivity and/or one or more of the biomarkers of resistance by performing microarray analysis or quantitative reverse transcriptase polymerase chain reaction (qRT-PCR). Expression of the biomarker(s) may be detected by determining the level of a messenger RNA (mRNA) transcribed from a nucleic acid molecule corresponding to a gene of the biomarker (s; e.g., a mRNA expressed from the ATP1B1 gene (SEQ ID NO: 201)) or a complementary DNA (cDNA) thereof.

A second aspect of the invention features a method of determining responsiveness of a patient having cancer (e.g., one of the cancers noted above, such as prostate cancer, ovarian cancer, or HCC) to irofulven. In particular, the patient may have a cancer that is resistant to one or more cancer therapies other than irofulven, such as prostate cancer, ovarian cancer, or HCC that is resistant to one or more cancer therapies other than irofulven. The method includes a) contacting a sample (e.g., a tumor sample) from the patient including one or more nucleic acid molecules with a device (e.g., a microarray or a device for performing a qRT-PCR reaction) including: i) one or more single-stranded nucleic acid molecules capable of specifically hybridizing with the nucleotides of one or more biomarkers of sensitivity selected from the biomarkers of Tables 1 and 3 (e.g., ATP1B1 (SEQ ID NO: 201)); and/or ii) one or more single-stranded nucleic acid molecules capable of specifically hybridizing with the nucleotides of one or more biomarkers of resistance selected from the biomarkers of Tables 2 and 4 (e.g., IGLC1 (SEQ ID NO: 301, 302, 303, or 318)); and b) measuring hybridization, or an amplification product resulting from hybridization, between the one or more nucleic acid molecules from the patient and the single-stranded nucleic acid molecules of the device to detect a level of expression of one or more of the biomarkers of sensitivity and/or one or more of the biomarkers of resistance. The patient is determined to be responsive to irofulven if: i) the level of expression of the biomarkers of sensitivity is substantially similar to the level of expression of the biomarkers of sensitivity (e.g., ATP1B1 (SEQ ID NO: 201)) in a cell (e.g., a cancer cell) or tissue (e.g., a tumor tissue) known to be sensitive to irofulven; and/or ii) the level of expression of the biomarkers of resistance (e.g., IGLC1 (SEQ ID NO: 301, 302, 303, or 318)) is substantially dissimilar to the level of expression of the biomarkers of resistance in a cell (e.g., a cancer cell) or tissue (e.g., a tumor tissue) known to be resistant to irofulven.

The method of the second aspect can further include administering irofulven to the patient if: i) the level of expression of the biomarkers of sensitivity (e.g., ATP1B1 (SEQ ID NO: 201)) is substantially similar to the level of expression of the biomarkers of sensitivity in a cell (e.g., a cancer cell) or tissue (e.g., a tumor tissue) known to be sensitive to irofulven; and/or ii) the level of expression of the biomarkers of resistance (e.g., IGLC1 (SEQ ID NO: 301, 302, 303, OR 318)) is substantially dissimilar to the level of expression of the biomarkers of resistance in a cell (e.g., a cancer cell) or tissue (e.g., a tumor tissue) known to be resistant to irofulven. The method can further include administering one or more cancer therapies other than irofulven to the patient if: i) the level of expression of the biomarkers of sensitivity (e.g., ATP1B1 (SEQ ID NO: 201)) is substantially dissimilar to the level of expression of the biomarkers of sensitivity in a cell (e.g., a cancer cell) or tissue (e.g., a tumor tissue) known to be sensitive to irofulven; and/or ii) the level of expression of the biomarkers of resistance is substantially similar to the level of expression of the biomarkers of resistance (e.g., IGLC1 (SEQ ID NO: 301, 302, 303, OR 318)) in a cell (e.g., a cancer cell) or tissue (e.g., a tumor tissue) known to be resistant to irofulven. In particular, the one or more of the cancer therapies includes surgery, radiation, or a therapeutic agent, such as a docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, cisplatin, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methylgag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab.

The invention also features a method of treating cancer in a patient in need thereof (e.g., one of the cancers noted above, such as prostate cancer, ovarian cancer, or HCC) that includes administering irofulven to the patient, in which the patient has been determined to be responsive to irofulven according to the method of the first or second aspect of the invention. In particular, the patient may have a cancer that is resistant to one or more cancer therapies other than irofulven (e.g., a patient with prostate cancer, ovarian cancer, or HCC that is resistant to one or more cancer therapies other than irofulven).

A third aspect of the invention features a method of treating a patient having cancer (e.g., one of the cancers noted above, such as prostate cancer, ovarian cancer, or HCC). In particular, the patient may have a cancer that is resistant to one or more cancer therapies other than irofulven (e.g., a patient with prostate cancer, ovarian cancer, or HCC that is resistant to one or more cancer therapies other than irofulven). The method includes a) contacting a sample (e.g., a tumor sample) from the patient including one or more nucleic acid molecules with a device (e.g., a microarray or a device for performing a qRT-PCR reaction) including: i) one or more single-stranded nucleic acid molecules capable of specifically hybridizing with the nucleotides of one or more biomarkers of sensitivity selected from the biomarkers of Tables 1 and 3 (e.g., ATP1B1 (SEQ ID NO: 201)); and/or ii) one or more single-stranded nucleic acid molecules capable of specifically hybridizing with the nucleotides of one or more biomarkers of resistance selected from the biomarkers of Tables 2 and 4 (e.g., IGLC1 (SEQ ID NO: 301, 302, 303, OR 318)); and b) measuring hybridization, or an amplification product resulting from hybridization, between the one or more nucleic acid molecules from the patient and the single-stranded nucleic acid molecules of the device to detect a level of expression of one or more of the biomarkers of sensitivity and/or one or more of the biomarkers of resistance; and c) administering irofulven to the patient if: i) the level of expression of the biomarkers of sensitivity is substantially similar to the level of expression of the biomarkers of sensitivity in a cell (e.g., a cancer cell) or tissue (e.g., a tumor tissue) known to be sensitive to irofulven; and/or ii) the level of expression of the biomarkers of resistance is substantially dissimilar to the level of expression of the biomarkers of resistance in a cell (e.g., a cancer cell) or tissue (e.g., a tumor tissue) known to be resistant to irofulven.

The method of the third aspect of the invention may further include administering one or more additional therapies (e.g., surgery, radiation, or a therapeutic agent) to the patient prior to, concurrently with, or after administration of irofulven. In particular, the therapeutic agent may be selected from the group consisting of docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, cisplatin, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab. The therapeutic agent can be administered parenterally (e.g. intravenously, intramuscularly, transdermally, intradermally, intra-arterially, intracranially, subcutaneously, intraorbitally, intraventricularly, intraspinally, intraperitoneally, or intranasally), enterally, or topically.

In the second or third aspect of the invention, irofulven may be administered parenterally (e.g. intravenously, intramuscularly, transdermally, intradermally, intra-arterially, intracranially, subcutaneously, intraorbitally, intraventricularly, intraspinally, intraperitoneally, or intranasally), enterally, or topically. Preferably, irofulven is administered by intravenous injection. Irofulven may be administered to the patient two or more times, such as one or more times daily, weekly, every two weeks, every three weeks, or monthly (e.g., one or more times per week for two weeks or more). Additionally, a second dose of irofulven may be administered to the patient two weeks, three weeks, four weeks, or five weeks after administration of a prior dose of irofulven. In particular, irofulven is administered in a 3 week treatment regimen in which the irofulven is administered on day 1 an day 8. The treatment regimen may be repeated two to twenty times or more, as needed.

In particular, irofulven may be administered to the patient at a dose of about 0.05 mg/kg to 5 mg/kg, such as at a dose of about 0.1 mg/kg to 1 mg/kg. For example, irofulven may be administered at a dose of about 0.15 mg/kg, 0.20 mg/kg, 0.25 mg/kg, 0.30 mg/kg, 0.35 mg/kg, 0.40 mg/kg, 0.45 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, or 0.95 mg/kg. Irofulven may be administered to the patient in a treatment regimen at least once per week for at least two weeks and/or on day 1 and day 8 of a 3 week treatment regimen, in which the treatment regimen occurs one or more times (e.g., the treatment regimen is repeated two to twenty times). In particular, irofulven is administered to the patient at a dose of about 0.1 mg/kg to 1 mg/kg, such as a dose of about 0.2 mg/kg to about 0.6 mg/kg (e.g., a dose of about 0.45 mg/kg). This dosage of irofulven can be administered in a 3 week treatment regimen, in which irofulven is administered on day 1 and day 8.

In the second or third aspect of the invention, the contacting step (a) and the measuring step (b) may occur prior to, concurrent with, or after administration of irofulven to the patient. Additionally, the contacting step (a) and the measuring step (b) may occur two or more times, e.g., during treatment with irofulven. For example, the contacting step (a) and the measuring step (b) may occur two or more times to assess the continued sensitivity of the patient to irofulven.

In any of the above aspects of the invention, the device can include at least two, at least three, at least four, at least five, at least six, at least seven, at least eight, at least nine, at least ten, or more single-stranded nucleic acid molecules capable of specifically hybridizing with the nucleotides of one or more biomarkers of sensitivity selected from the biomarkers of Tables 1 and 3 (e.g., ATP1B1 (SEQ ID NO: 201)); and/or at least two, at least three, at least four, at least five, at least six, at least seven, at least eight, at least nine, at least ten, or more single-stranded nucleic acid molecules capable of specifically hybridizing with the nucleotides of one or more biomarkers of resistance selected from the biomarkers of Tables 2 and 4 (e.g., IGLC1 (SEQ ID NO: 301, 302, 303, OR 318)). In particular, one or more of the single-stranded nucleic acid molecules of the device have a length in the range of 10 to 100 nucleotides in length (e.g., a length in the range of 20 to 60 nucleotides).

In any of the above aspects of the invention, the method may include converting the level of expression of one or more of the biomarkers of sensitivity (e.g., one, two, three, four, five, ten, twenty, or all of the biomarkers shown in Tables 1 and 3, such as ATP1B1 (SEQ ID NO: 201)) and/or one or more of the biomarkers of resistance (e.g., one, two, three, four, five, ten, twenty, or all of the biomarkers shown in Tables 2 and 4, such as IGLC1 (SEQ ID NO: 301, 302, 303, OR 318)) into a mean score, in which the mean score indicates the responsiveness of the patient to irofulven. The method can further include subtracting the mean score for one or more of the biomarkers of resistance (e.g., one, two, three, four, five, ten, twenty, or all of the biomarkers shown in Tables 2 and 4, such as IGLC1 (SEQ ID NO: 301, 302, 303, OR 318)) from the mean score for one or more of the biomarkers of sensitivity (e.g., one, two, three, four, five, ten, twenty, or all of the biomarkers shown in Tables 1 and 3, such as ATP1B1 (SEQ ID NO: 201)) to obtain a difference score, in which the difference score indicates the responsiveness of the patient to irofulven. In particular, the mean score and/or the difference score above a cutoff value indicates that the patient is responsive to irofulven, such as if the cutoff value is about 0.1, about 0.15, about 0.2, about 0.25, about 0.3, about 0.35, about 0.4, about 0.45, about 0.5, or greater.

In any of the above aspects of the invention, the biomarker of sensitivity may be selected from one or more of ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), and GJA1 (SEQ ID NO: 218). The biomarker of resistance may be selected from one or more of IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and GTSF1 (SEQ ID NO: 321).

For example, the biomarkers of sensitivity may include ATP1B1 (SEQ ID NO: 201 or 219) and UCHL1 (SEQ ID NO: 202). The biomarkers of sensitivity may include ATP1B1 (SEQ ID NO: 201 or 219), UCHL1 (SEQ ID NO: 202), and PTGR1 (SEQ ID NO: 203 or 210). The biomarkers of sensitivity may include ATP1B1 (SEQ ID NO: 201 or 219), UCHL1 (SEQ ID NO: 202), PTGR1 (SEQ ID NO: 203 or 210), and NME7 (SEQ ID NO: 204). The biomarkers of sensitivity may include ATP1B1 (SEQ ID NO: 201 or 219), UCHL1 (SEQ ID NO: 202), PTGR1 (SEQ ID NO: 203 or 210), NME7 (SEQ ID NO: 204), and PLS3 (SEQ ID NO: 205). The biomarkers of sensitivity may include ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), and S100A10 (SEQ ID NO: 206). The biomarkers of sensitivity may include ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), and CD24 (SEQ ID NO: 207 or 209 or 220). The biomarkers of sensitivity may include ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), and NQO1 (SEQ ID NO: 208 or 216). The biomarkers of sensitivity may include ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), and MYOF (SEQ ID NO: 211). The biomarkers of sensitivity may include ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), and LAPTM4B (SEQ ID NO: 212). The biomarkers of sensitivity may include ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), and CALD1 (SEQ ID NO: 213). The biomarkers of sensitivity may include ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), and PDGFC (SEQ ID NO: 214). The biomarkers of sensitivity may include ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), and BASP1 (SEQ ID NO: 215). The biomarkers of sensitivity may include ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), and ID1 (SEQ ID NO: 217). The biomarkers of sensitivity may include ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), and GJA1 (SEQ ID NO: 218).

For example, the biomarkers of resistance may include IGLC1 (SEQ ID NO: 301, 302, 303, or 318) and LAPTM5 (SEQ ID NO: 304 or 338). The biomarkers of resistance may include IGLC1 (SEQ ID NO: 301, 302, 303, or 318), LAPTM5 (SEQ ID NO: 304 or 338), and ARHGDIB (SEQ ID NO: 305 or 311). The biomarkers of resistance may include IGLC1 (SEQ ID NO: 301, 302, 303, or 318), LAPTM5 (SEQ ID NO: 304 or 338), ARHGDIB (SEQ ID NO: 305 or 311), and SLC43A3 (SEQ ID NO: 307). The biomarkers of resistance may include IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), and LCP1 (SEQ ID NO: 308). The biomarkers of resistance may include IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), and HCLS1 (SEQ ID NO: 309). The biomarkers of resistance may include IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), and CD53 (SEQ ID NO: 310). The IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), and MZB1 (SEQ ID NO: 313). The biomarkers of resistance may include IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), and RASSF5 (SEQ ID NO: 314 or 386). The biomarkers of resistance may include IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), and FAM46C (SEQ ID NO: 315). The biomarkers of resistance may include IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), and RCSD1 (SEQ ID NO: 316). The biomarkers of resistance may include IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), and IGJ (SEQ ID NO: 317). The biomarkers of resistance may include IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), and LPXN (SEQ ID NO: 319). The biomarkers of resistance may include IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), and ITGB7 (SEQ ID NO: 320). The biomarkers of resistance may include IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and GTSF1 (SEQ ID NO: 321).

In any of the above aspects of the invention, the device can be a microarray, such as a deoxyribonucleic acid (DNA)-based platform. Alternatively, the device can be for performing a qRT-PCR reaction (e.g., the device is used with a system for detecting the amplification product, for example, by fluorescence or by another method). The methods may also utilize both a microarray and a qRT-PCR. Thus, the expression level of the biomarkers of sensitivity (e.g., one, two, three, four, five, ten, twenty, or all of the biomarkers shown in Tables 1 and 3, such as ATP1B1 (SEQ ID NO: 201)) and/or the biomarkers of resistance (e.g., one, two, three, four, five, ten, twenty, or all of the biomarkers shown in Tables 2 and 4, such as IGLC1 (SEQ ID NO: 301, 302, 303, OR 318)) can be measured using qRT-PCR. In particular, the level of expression of one or more of the biomarkers of sensitivity and/or one or more of the biomarkers of resistance is determined by detecting the level of mRNA transcribed from one or more genes encoding one or more of the biomarkers of Tables 1-4.

In any of the above aspects of the invention, the cancer is selected from a solid tumor cancer and a hematological cancer. For example, the cancer is prostate cancer, ovarian cancer, HCC, multiple myeloma, breast cancer, acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), Hodgkin's lymphoma, cervical cancer, renal cell carcinoma (RCC), esophageal cancer, melanoma, glioma, pancreatic cancer, gastrointestinal stromal tumors (GIST), sarcoma, estrogen receptor-positive (ERpos) breast cancer, non-small cell lung carcinoma (NSCLC), colon cancer, bladder cancer, or squamous cell carcinoma of the head and neck (SCCHN). In particular, the cancer is prostate cancer, such as prostate cancer that is resistant to one or more cancer therapies other than irofulven. The cancer may also be ovarian cancer, such as ovarian cancer that is resistant to one or more cancer therapies other than irofulven. Alternatively, the cancer may be HCC, such as HCC that is resistant to one or more cancer therapies other than irofulven.

In any of the above aspects of the invention, the patient may exhibit cancer relapse (e.g., relapse of prostate cancer, ovarian cancer, or HCC), such as relapse after treatment with a therapeutic agent other than irofulven. In particular, the patient may exhibit cancer relapse prior to treatment with irofulven. Alternatively, the patient may have not been administered a treatment for cancer.

Definitions

As used herein, "a" or "an" means "at least one" or "one or more" unless otherwise indicated. In addition, the singular forms "a", "an", and "the" include plural referents unless the context clearly dictates otherwise.

As used herein, "about" refers to an amount ±10% of the recited value.

By "biomarker" is meant a nucleic acid molecule (e.g., a mRNA or its complement, for example, a cDNA) or a protein encoded by the nucleic acid molecule present in, or from, a cell or tissue. The expression of the biomarker correlates to the responsiveness (e.g., sensitivity or resistance) of the cell or tissue (and thus, the patient in which the cell or tissue resides or the patient from which the cell or tissue was obtained) to a cancer treatment (e.g., irofulven). In particular, a biomarker of sensitivity is a nucleic acid molecule (e.g., a mRNA or its complement) expressed from any one of the genes shown in Tables 1 and 3, or the protein encoded by the nucleic acid molecule, and a biomarker of resistance is a nucleic acid molecule (e.g., a mRNA or its complement) expressed from any one of the genes shown in Tables 2 and 4, or the protein encoded by the nucleic acid molecule.

The terms "cancer" and "cancerous" refer to or describe the physiological condition in mammals (e.g., humans) that is typically characterized by unregulated cell proliferation. Examples of cancer include, but are not limited to, prostate cancer, ovarian cancer (e.g., ovarian adenocarcinoma or embryonal carcinoma), liver cancer (e.g., hepatocellular carcinoma (HCC) or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. The term cancer includes solid tumors (e.g., prostate cancer, ovarian cancer, or hepatocellular carcinoma (HCC)) and hematological cancers (e.g., cancer of the blood, such as lymphoma (e.g., cutaneous T-cell lymphoma (CTCL))).

The terms "expression level" and "level of expression," as used herein, refer to the amount of a gene product in a cell, tissue, biological sample, organism, or patient, e.g., amounts of DNA, RNA (e.g. messenger RNA (mRNA)), or proteins corresponding to a given gene.

"Gene" as used herein indicates a coding or noncoding gene whose activity can be determined by measuring the produced RNA. Examples include protein coding genes, microRNAs, small nuclear RNAs and other RNAs with catalytic, regulatory or coding properties.

To "inhibit growth" as used herein means causing a reduction in cell growth (e.g., cancer cell growth, such as the NCI60 cancer cell lines) in vivo or in vitro by, e.g., 10%, 20%, 30%, 40%, 50%, 60%, 70%, 80%, 90%, 95%, or 99% or more, as evident by a reduction in the proliferation of cells exposed to a treatment (e.g., irofulven), relative to the proliferation of cells in the absence of the treatment. Growth inhibition may be the result of a treatment (e.g., irofulven) that induces apoptosis in a cell, induces necrosis in a cell, slows cell cycle progression, disrupts cellular metabolism, induces cell lysis, or induces some other mechanism that reduces the proliferation of cells.

The term "irofulven" as used herein refers to an antitumor agent that is a cytotoxic semi-synthetic derivative of illudin S, a sesquiterpene toxin found in the Jack 'o' Lantern mushroom. Irofulven or 6-hydroxymethylacylfulvene is an alkylating agent that initiates the apoptotic degradation of DNA leading to cell death. Irofulven ((6R)-6'-hydroxy-3'-(hydroxymethyl)-2',4',6'-trimethylspiro[cyclopropane-1,5'-inden]-7'(6'H)-one) has the structural molecular formula shown below:

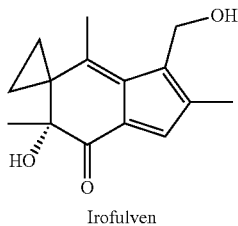

Irofulven

Irofulven is also described in MacDonald et al. (*Cancer Res.* 57 (2): 279-283, 1997), hereby incorporated by reference.

"Microarray" as used herein means a device employed by any method that quantifies one or more subject oligonucleotides, e.g., RNA, DNA, cDNA, or analogues thereof, at a time. For example, many DNA microarrays, including those made by Affymetrix (e.g., an Affymetrix HG-U133A or HG-U133_Plus_2 array), use several probes for determining the expression of a single gene. The DNA microarray may contain oligonucleotide probes that may be, e.g., full-length cDNAs complementary to an RNA or cDNA fragments that hybridize to part of an RNA. The DNA microarray may also contain modified versions of DNA or RNA, such as locked nucleic acids or LNA. Exemplary RNAs include mRNA, miRNA, and miRNA precursors.

As used herein, the term "percent (%) sequence identity" refers to the percentage of nucleic acid residues of a candidate sequence, e.g., a probe or primer of the invention, that are identical to the nucleic acid residues of a reference sequence, e.g., a biomarker sequence of the invention, after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using computer software, such as BLAST, BLAST-2, BLAST-P, BLAST-N, BLAST-X, WU-BLAST-2, ALIGN, ALIGN-2, CLUSTAL, Megalign (DNASTAR). In addition, those skilled in the art can determine appropriate parameters for measuring alignment, including any algorithms needed to achieve optimal alignment over the length of the sequences being compared.

"NCI60" as used herein means a panel of 60 cancer cell lines from lung, colon, breast, ovarian, leukemia, renal, melanoma, prostate and brain cancers including the following cancer cell lines: NSCLC_NCIH23, NSCLC_NCIH522, NSCLC_A549ATCC, NSCLC_EKVX, NSCLC_NCIH226, NSCLC_NCIH332M, NSCLC_H460, NSCLC_HOP62, NSCLC_HOP92, COLON_HT29, COLON_HCC-2998, COLON_HCT116, COLON_SW620, COLON_COLO205, COLON_HCT15, COLON_KM12, BREAST_MCF7, BREAST_MCF7ADRr, BREAST_MDAMB231, BREAST_HS578T, BREAST_MDAMB435, BREAST_MDN, BREAST_BT549, BREAST_T47D, OVAR_OVCAR3, OVAR_OVCAR4, OVAR_OVCAR5, OVAR_OVCAR8, OVAR_IGROV1, OVAR_SKOV3, LEUK_CCRFCEM, LEUK_K562, LEUK_MOLT4, LEUK_HL60, LEUK_RPMI8266, LEUK_SR, RENAL_UO31, RENAL_SN12C, RENAL_A498, RENAL_CAKI1, RENAL_RXF393, RENAL_7860, RENAL_ACHN, RENAL_TK10, MELAN_LOXIMVI, MELAN_MALME3M, MELAN_SKMEL2, MELAN_SKMEL5, MELAN_SKMEL28, MELAN_M14, MELAN_UACC62, MELAN_UACC257, PROSTATE_PC3, PROSTATE_DUI45, CNS_SNB19, CNS_SNB75, CNS_U251, CNS_SF268, CNS_SF295, and CNS_SF539.

The terms "patient" and "subject," as used interchangeably herein, refer to any animal (e.g., a mammal, such as a human). A patient to be treated or tested for responsiveness to a treatment (e.g., irofulven) according to the methods described herein may be one who has been diagnosed with a cancer, such as those described herein, e.g., prostate cancer, ovarian cancer, or hepatocellular carcinoma (HCC). Diagnosis may be performed by any method or techniques known in the art, such as x-ray, MRI, or biopsy, and confirmed by a physician. To minimize exposure of a patient to drug treatments that may not be therapeutic, the patient may be determined to be either responsive or non-responsive to a cancer treatment, such as irofulven, according to the methods described herein.

"Resistant" or "resistance" as used herein means that a cell (e.g., a cancer cell), a tissue (e.g., a tumor), or a patient having cancer (e.g., a human having cancer) is able to withstand treatment with an anti-cancer agent (e.g., irofulven). In particular, the treatment does not inhibit the growth of a cancer cell in vitro by about 70%, 80%, 90%, 95%, 99% or 100% relative to the growth of a cancer cell not exposed to the treatment. Resistance to treatment may be determined by a cell proliferation assay, e.g., a cell-based assay, which measures the growth of treated cells as a function of the absorbance of the cells of an incident light beam, such as the NCI60 assays described herein. In this assay, greater absorbance indicates greater cell growth, and thus, resistance to the treatment.

A cancer patient (e.g., a patient with prostate cancer, ovarian cancer, or a hepatocellular carcinoma) may also have resistance to a cancer therapy other than irofulven, such as surgery, radiation, or a therapeutic agent (e.g., docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, or 5-fluorouracil (5-FU)).

The terms "responsive" and "responsiveness," as used herein, refer to the likelihood that a cancer treatment (e.g., irofulven) has (e.g., induces) a desired effect, or, alternatively, refer to the strength of a desired effect caused or induced by the treatment in a cell (e.g., a cancer cell), a tissue (e.g., a tumor), or a patient having cancer (e.g., a human having cancer). For example, the desired effect can include inhibition of the growth of a cancer cell in vitro by more than 10%, 20%, 30%, 40%, 50%, 60%, 70%, 80%, 90%, or 100% relative to the growth of a cancer cell not exposed to the treatment. The desired effect can also include reduction in tumor mass by, e.g., about 10%, 20%, 30%, 40%, 50%, 60%, 70%, 80%, 90%, or 100%. Responsiveness to treatment may be determined by a cell proliferation assay, e.g., a cell-based assay, which measures the growth of treated cells as a function of the absorbance of the cells of an incident light beam, such as the NCI60 assays described herein. In this assay, lesser absorbance indicates lesser cell growth, and thus, sensitivity to the treatment. A greater reduction in growth indicates more sensitivity to the treatment. In particular, "responsiveness" is a measure of the sensitivity or resistance of a patient to a treatment for cancer (e.g., irofulven).

The term "sample," as used herein, refers to any specimen (such as cells, tissue (e.g., a tissue sample obtained by biopsy), blood, serum, plasma, urine, cerebrospinal fluid, or pancreatic fluid) taken from a subject. Preferably, the sample is taken from a portion of the body affected by a cancer (e.g., a biopsy of the cancer tissue, such as prostate, ovarian, or lung cancer tissue). Biopsy may involve fine needle aspiration biopsy, core needle biopsy (e.g., stereotactic core needle biopsy, vacuum-assisted core biopsy, or magnetic resonance imaging (MRI) guided biopsy), or surgical biopsy (e.g., incisional biopsy or excisional biopsy). The sample may undergo additional purification and processing, for example, to remove cell debris and other unwanted molecules. Additional processing may further involve amplification, e.g., using PCR (RT-PCR). The standard methods of sample purification, such as removal of unwanted molecules, are known in the art.

"Sensitive" and "sensitivity" as used herein refer to a cell (e.g., a cancer cell), a tissue (e.g., a tumor), or a patient having cancer (e.g., a human having cancer) that is responsive to treatment, such as an anti-cancer agent (e.g., irofulven) or radiation treatment. In particular, the treatment inhibits the growth of a cancer cell in vitro by about 70%, 80%, 90%, 95%, 99% or 100% relative to the growth of a cancer cell not exposed to the treatment. Sensitivity to treatment may be determined by a cell proliferation assay, e.g., a cell-based assay, which measures the growth of treated cells as a function of the absorbance of the cells of an incident light beam, such as the NCI60 assays described herein. In this assay, lesser absorbance indicates lesser cell growth, and thus, sensitivity to the treatment.

"Treatment," "medical treatment," to "treat," and "therapy," as used interchangeably herein, refer to administering or exposing a patient having cancer (e.g., a human), a cell, or a tumor to an anti-cancer agent (e.g., a drug, a protein, an antibody, a nucleic acid, a chemotherapeutic agent, or a radioactive agent), or to some other form of medical intervention used to treat or prevent a disease, disorder, or condition (e.g., surgery, cryotherapy, radiation therapy, or combinations thereof). In particular, a medical treatment can include irofulven. For example, the cancer to be treated is a solid tumor or a hematological cancer. Examples of cancer include, e.g., prostate cancer, ovarian cancer (e.g., ovarian adenocarcinoma or embryonal carcinoma), liver cancer (e.g., hepatocellular carcinoma (HCC) or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. Radiation therapy includes the administration of a radioactive agent to a patient or exposure of a patient to radiation. The radiation may be generated from sources such as particle accelerators and related medical devices or agents that emit, e.g., X-radiation, gamma radiation, or electron (Beta radiation) beams. A treatment may be or further include surgery, e.g., to remove a tumor from a subject or living organism.

Other features and advantages of the invention will be apparent from the following Detailed Description, the drawings, and the claims.

BRIEF DESCRIPTION OF THE DRAWINGS

FIG. 1 is a graph grouping predicted sensitivity to irofulven by cancer type. Each gray circle represents the predicted irofulven sensitivity of one patient calculated as the difference between the mean of the expression levels of the biomarkers of sensitivity and the mean of the expression levels of the biomarkers of resistance for the patient. Patients are grouped according to cancer type. The median predicted sensitivity (black bar) for a cancer type is related to the relative response rate for that cancer type. The predictions are used for relative comparisons to compare cancer types and cannot be used for absolute predictions of response rate for a given cancer type. The predictions are normalized to a scale of 0 to 100 for all 3,522 patients.

DETAILED DESCRIPTION OF THE INVENTION

I have discovered that the expression levels of the biomarkers shown in Tables 1-4 may be detected in a patient having cancer and are useful for predicting the responsiveness of the patient to irofulven. These patients may already be determined to be resistance to a therapy other than irofulven, such as docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, cisplatin, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, or rituximab.

A device, such as a microarray, with one or more single-stranded oligonucleotide probes that have substantial identity (e.g., at least 85%, 90%, 95%, 99%, or 100% sequence identity) to a sequence that is complementary or identical to the nucleic acid sequence of one or more biomarkers shown in Tables 1-4 can be used according to the methods described herein to assess the responsiveness of a cancer patient to treatment with irofulven. For example, the probes can be used to detect one or more (e.g., two, three, four, five, ten, twenty, or all) of the biomarkers of sensitivity listed in Tables 1 and 3, such as ATP1B1 (SEQ ID NO: 201 or 219), in a sample (e.g., a tumor sample) from a patient having cancer (e.g., prostate cancer, ovarian cancer, or hepatocellular carcinoma (HCC)). Additionally, the probes can be used to detect one or more (e.g., two, three, four, five, ten, twenty, or all) of the biomarkers of resistance listed in Tables 2 and 4, such as IGLC1 (SEQ ID NO: 301, 302, 303, or 318), in a sample (e.g., a tumor sample) from a patient having cancer (e.g., prostate cancer, ovarian cancer, or hepatocellular carcinoma (HCC)).

Accordingly, the invention features individual biomarkers (e.g., ATP1B1 (SEQ ID NO: 201 or 219) or IGLC1 (SEQ ID NO: 301, 302, 303, or 318)) and sets of biomarkers shown in Tables 1-4 that can be used to determine the responsiveness of a cancer patient to irofulven at various stages of disease progression (e.g., patients diagnosed with cancer or patients after cancer recurrence) and at different times during the treatment process (e.g., prior to administration of any cancer treatment, after administration of one or more cancer treatments other than irofulven, prior to administration of irofulven, or during administration of irofulven). Additionally, the methods can be used to determine the irofulven responsiveness of a patient with cancer that is resistant to one or more cancer therapies other than irofulven, such as docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, cisplatin, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, or rituximab.

In particular, the invention provides methods for determining whether a patient may be responsive to irofulven by, e.g., detecting the expression level (e.g., mRNA or protein produced therefrom) of one or more of the biomarkers shown in Tables 1-4 (e.g., ATP1B1 (SEQ ID NO: 201 or 219)) in a biological sample (e.g., a tumor biopsy) obtained from the subject using a device (e.g., a microarray or a protein array). The expression level of one or more of the biomarkers of sensitivity may then be compared to the expression level of the biomarkers in a cell or tissue known to be sensitive or resistant to irofulven to determine the patient's responsiveness to irofulven. The patient may be responsive to irofulven if the expression level of the one or more of the biomarkers of sensitivity (e.g., one or more of ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), and GJA1 (SEQ ID NO: 218)) is substantially similar to the expression level of the biomarkers of sensitivity in a cell or tissue known to be sensitive to irofulven (e.g., from a patient sensitive to irofulven). The patient may also be responsive to irofulven if the level of expression of one or more of the biomarkers of resistance (e.g., one or more of IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and GTSF1 (SEQ ID NO: 321)) is substantially dissimilar to the expression level of the biomarkers of resistance in a cell or tissue known to be resistant to irofulven (e.g., from a patient resistant to irofulven).

The invention also features methods of treating a patient having cancer, such as a patient having a cancer that is resistant to one or more cancer therapies other than irofulven, by detecting the expression levels of one or more of the biomarkers shown in Tables 1-4 (e.g., ATP1B1 (SEQ ID NO: 201)) in a sample (e.g., a tumor sample) from the patient, and then administering irofulven based on the expression levels of the biomarkers. In particular, a patient having cancer may be administered irofulven if the expression level of one or more biomarkers of sensitivity is substantially similar to the expression level of the biomarkers of sensitivity in a cell or tissue known to be sensitive to irofulven. Additionally, a patient having cancer may be administered irofulven if the expression level of one or more biomarkers of resistance is substantially dissimilar to the expression level of the biomarkers of resistance in a cell or tissue known to be resistant to irofulven. Thus, the methods can be used to treat cancer patients predicted to be responsive to irofulven, such as patients having, e.g., prostate cancer, ovarian cancer, hepatocellular carcinoma (HCC), cervical cancer, renal cell carcinoma (RCC), esophageal cancer, melanoma, glioma, pancreatic cancer, gastrointestinal stromal tumors (GIST), sarcoma, estrogen receptor-positive (ERpos) breast cancer, non-small cell lung carcinoma (NSCLC), colon cancer, bladder cancer, squamous cell carcinoma of the head and neck (SCCHN), acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), and Hodgkin's lymphoma. Alternatively, a patient having cancer may not be administered irofulven if the expression level of one or more biomarkers of sensitivity is substantially dissimilar to the expression level of the biomarkers of sensitivity in a cell or tissue known to be sensitive to irofulven. Likewise, a patient having cancer may not be administered irofulven if the expression level of one or more biomarkers of resistance is substantially similar to the expression level of the biomarkers of resistance in a cell or tissue known to be resistant to irofulven.

Methods are described herein for identifying biomarkers of drug responsiveness, detecting biomarker gene expression in cancer patients, determining the responsiveness of a cancer patient to irofulven, and treating cancer patients with irofulven. Also described are devices and kits for use in these methods.

Methods for Identifying Biomarkers of Drug Responsiveness

The invention features methods for identifying biomarkers (e.g., one or more of the biomarkers of Tables 1-4) for determining the responsiveness of a cancer patient to a cancer treatment, such as irofulven. Such methods can involve, for example, an algorithm based on growth inhibition values (GI50) of cell lines (e.g., NCI60 cell lines) subjected to treatment with irofulven, followed by measurement of gene expression (e.g., using a microarray (e.g., an Affymetrix HG-U133A or HG-U133_Plus_2 array)).

Methodology of the In Vitro Cancer Growth Inhibition Screen

The human tumor cell lines of the cancer screening panel may be grown in RPMI 1640 medium containing 5% fetal bovine serum and 2 mM L-glutamine. Cells may be inoculated into 96 well microtiter plates in 100 µL at plating densities ranging from 5,000 to 40,000 cells/well depending on the doubling time of individual cell lines. After cell inoculation, the microtiter plates may be incubated at 37° C., 5% CO2, 95% air and 100% relative humidity for 24 hours prior to addition of experimental compounds.

After 24 hours, two plates of each cell line may be fixed in situ with TCA, to represent a measurement of the cell population for each cell line at the time of compound addition (Tz). Experimental compounds may be solubilized in dimethyl sulfoxide at 400-fold the desired final maximum test concentration and stored frozen prior to use. At the time of compound (e.g., irofulven) addition, an aliquot of frozen concentrate may be thawed and diluted to twice the desired final maximum test concentration with complete medium containing 50 µg/ml Gentamicin. A total of four additional 10-fold or ½ log serial dilutions are made to provide a total of five concentrations plus control. Aliquots of 100 µl of these different compound dilutions are added to the appropriate microtiter wells already containing 100 µl of medium, resulting in the required final compound concentrations.

Following compound (e.g., irofulven) addition, the plates may be incubated for an additional 48 h at 37° C., 5% CO2, 95% air, and 100% relative humidity. For adherent cells, the assay may be terminated by the addition of cold TCA. Cells may be fixed in situ by the gentle addition of 50 µl of cold 50% (w/v) TCA (final concentration, 10% TCA) and incubated for 60 minutes at 4° C. The supernatant may be discarded, and the plates may be washed five times with tap water and air-dried. Sulforhodamine B (SRB) solution (100 µl) at 0.4% (w/v) in 1% acetic acid may be added to each well, and the plates may be incubated for 10 minutes at room temperature. After staining, unbound dye may be removed by washing five times with 1% acetic acid and the plates may be air-dried. Bound stain may be subsequently solubilized with 10 mM trizma base, and the absorbance may be read on an automated plate reader at a wavelength of 515 nm. For suspension cells, the methodology may be the same, except that the assay may be terminated by fixing settled cells at the bottom of the wells by gently adding 50 µl of 80% TCA (final concentration, 16% TCA). Using the seven absorbance measurements [time zero, (Tz), control growth, (C), and test growth in the presence of compound (e.g., irofulven) at the five concentration levels (Ti)], the percentage growth may be calculated at each of the compound concentrations levels. Percentage growth inhibition may be calculated as:

$$[(Ti-Tz)/(C-Tz)] \times 100 \text{ for concentrations for which } Ti >/= Tz$$

$$[(Ti-Tz)/Tz] \times 100 \text{ for concentrations for which } Ti < Tz$$

Three dose response parameters may be calculated for each experimental agent (e.g., irofulven). Growth inhibition of 50% (GI50) is calculated from $[(Ti-Tz)/(C-Tz)]\times$ 100=50, which is the agent (e.g., irofulven) concentration resulting in a 50% reduction in the net protein increase (as measured by SRB staining) in control cells during the compound incubation. The compound concentration resulting in total growth inhibition (TGI) is calculated from Ti=Tz. The LC50 (concentration of compound resulting in a 50% reduction in the measured protein at the end of the compound treatment as compared to that at the beginning) indicating a net loss of cells following treatment is calculated from $[(Ti-Tz)/Tz] \times 100 = -50$. Values are calculated for each of these three parameters if the level of activity is reached; however, if the effect is not reached or is exceeded, the value for that parameter is expressed as greater or less than the maximum or minimum concentration tested.

Gene Expression and Growth Inhibition Analysis

The gene expression measurements of NCI60 cancer cell lines can be obtained from a publically available database (e.g., the National Cancer Institute and the Massachusetts Institute of Technology). Each dataset can be normalized so that sample expression measured by different chips can be compared. The preferred method of normalization is the logit transformation, which may be performed for each gene y on each chip, as follows:

$$\text{logit}(y) = \log[(y-\text{background})/(\text{saturation}-y)],$$

where background is calculated as the minimum intensity measured on the chip minus 0.1% of the signal intensity range: min−0.001*(max−min), and saturation is calculated as the maximum intensity measured on the chip plus 0.1% of the signal intensity range: max+0.001*(max−min). The resulting logit transformed data may then be z-transformed to mean zero and standard deviation 1.

Next, gene expression can be correlated to cancer cell growth inhibition. Growth inhibition data (GI50) of the NCI60 cell lines in the presence of a cancer treatment, such as irofulven, can be obtained from the NCI. The correlation between the logit-transformed expression level of each gene in each cell line and the logarithm of GI50 (the concentration of a given compound that results in a 50% inhibition of growth) can be calculated, e.g., using the Pearson correlation coefficient or the Spearman Rank-Order correlation coefficient. Instead of using GI50s, any other measure of patient sensitivity to a given treatment (e.g., irofulven) may be correlated to gene expression levels of the patient. Since a plurality of measurements may be available for a single gene, the most accurate determination of correlation coefficient can be, e.g., the median of the correlation coefficients calculated for all probes measuring expression of the same gene.

For example, the median correlation coefficient of gene expression measured on a probe to growth inhibition or patient sensitivity to irofulven can be calculated for all genes of interest. Genes that have a median correlation above, e.g., 0.20, 0.21 0.22. 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, or higher (e.g., 0.2 or higher), can be used as biomarkers of sensitivity for assessing responsiveness of a cancer patient (e.g., a patient having cancer that is resistant to one or more cancer therapies other than irofulven) to irofulven. Likewise, genes that have a median correlation below, e.g., −0.20, −0.21, −0.22, −0.23, −0.24, −0.25, −0.26, −0.27, −0.28, −0.29, −0.30, −0.31, −0.32, −0.33, −0.34, −0.35, −0.36, −0.37, −0.38, −0.39, −0.40, or lower (e.g., −0.2 or lower), can be used as biomarkers of resistance for assessing responsiveness of a cancer patient (e.g., a patient having cancer that is resistant to one or more cancer therapies other than irofulven) to irofulven. Preferably, the correlation coefficient of a biomarker of sensitivity will exceed 0.2, while the correlation coefficient of a biomarker of resistance will be less than −0.2. The result is a list of biomarker genes that correlate to sensitivity or resistance to irofulven, as shown in Tables 1 and 3 and Tables 2 and 4, respectively.

Cancer Types

The methods, devices, and kits of the invention can be used for diagnosing, prognosing, monitoring, treating, and/or reducing cancer in a subject suffering from, diagnosed with, or susceptible to cancer. Non-limiting examples of cancers that can be diagnosed, prognosed, monitored, treated, or reduced using the methods include hematological and solid tumors. In particular, cancers include, e.g., prostate cancer, ovarian cancer (e.g., ovarian adenocarcinoma or embryonal carcinoma), liver cancer (e.g., hepatocellular carcinoma (HCC) or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system.

In particular, the methods are useful for diagnosing, prognosing, monitoring, treating, or preventing, e.g., prostate cancer, ovarian cancer, hepatocellular carcinoma (HCC), cervical cancer, renal cell carcinoma (RCC), esophageal cancer, melanoma, glioma, pancreatic cancer, gastrointestinal stromal tumors (GIST), sarcoma, estrogen receptor-positive (ERpos) breast cancer, non-small cell lung carcinoma (NSCLC), colon cancer, bladder cancer, squamous cell carcinoma of the head and neck (SCCHN), acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), and Hodgkin's lymphoma.

For example, the cancer can be prostate cancer, such as Stage I, II (e.g., IIA or IIB), III, or IV prostate cancer. In particular, the cancer may be prostate cancer that is resistant to one or more cancer therapies, such as docetaxel, cabazitaxel, mitoxantrone, estramustine, prednisone, and/or surgery. Alternatively, the cancer is an ovarian cancer. The ovarian cancer can be, for example, a Stage I (e.g., Stage IA, IB, or IC), Stage II (e.g., Stage IIA or IIB), Stage III (e.g., Stage IIIA1, IIIA2, IIIB, or IIIC), or Stage IV (e.g., Stage IVA or IVB) ovarian cancer. In particular, the cancer can be ovarian cancer that is resistant to one or more cancer therapies, such as docetaxel, carboplatin, bevacizumab, paclitaxel, gemcitabine, doxorubicin, topotecan, etoposide, tamoxifen, and/or letrozole. Additionally, the cancer can be HCC, such as Stage I, Stage II, Stage III (e.g., Stage IIIA, IIIB, or IIIC), or Stage IV (e.g., Stage IVA or IVB) HCC. In particular, the cancer can be HCC that is resistant to one or more cancer therapies, such as sorafenib, doxorubicin, cisplatin, gemcitabine, capecitabine, oxaliplatin, interferon-alpha, and/or 5-fluorouracil (5-FU).

Methods for Detecting Biomarker Gene Expression in Cancer Patients

A cancer patient can be assessed for sensitivity or resistance to irofulven by detecting gene expression of a biomarker (e.g., one or more of the biomarkers of Tables 1-4) in a biological sample obtained from the cancer patient (e.g., a patient having cancer that is resistant to one or more cancer therapies other than irofulven). The biological sample can include, for example, cells, tissue (e.g., a tissue sample obtained by biopsy), blood, serum, plasma, urine, sputum, cerebrospinal fluid, lymph tissue or fluid, or pancreatic fluid. For example, the biological sample can be fresh frozen or formalin-fixed paraffin embedded (FFPE) tissue obtained from the subject, such as a tumor sample (e.g., a biopsy) from the tissue of interest (e.g., prostate, ovarian, lung, lymph nodes, thymus, spleen, bone marrow, breast, colorectal, pancreatic, cervical, bladder, gastrointestinal, head, or neck tissue).

RNA Extraction and Biomarker Expression Measurement

Cell samples or tissue samples may be snap frozen in liquid nitrogen until processing. RNA may be extracted using, e.g., Trizol Reagent from Invitrogen following manufacturer's instructions, and detected directly or converted to cDNA for detection. RNA may be amplified using, e.g., MessageAmp kit from Ambion following manufacturer's instructions. Amplified RNA may be quantified using, e.g., HG-U133A or HG-U133_Plus2 GeneChip from Affymetrix Inc. or a compatible apparatus, e.g., the GCS3000Dx GeneChip® System from Affymetrix Inc., using the manufacturer's instructions. The resulting biomarker expression measurements may be further analyzed as described herein. The procedures described can be implemented using, e.g., R software available from R-Project and supplemented with packages available from Bioconductor.

One or more of the biomarkers shown in Tables 1-4 (e.g., ATP1B1 (SEQ ID NO: 201)) may be measured in a biological sample (e.g., a tumor sample) obtained from the cancer patient (e.g., a patient with any of the cancer types described herein, such as a patient having cancer that is resistant to one or more cancer therapies other than irofulven) using, e.g., polymerase chain reaction (PCR), reverse transcriptase PCR (RT-PCR), quantitative real-time PCR (qRT-PCR), an array (e.g., a microarray), a genechip, pyrosequencing, nanopore sequencing, sequencing by synthesis, sequencing by expansion, single molecule real time technology, sequencing by ligation, microfluidics, infrared fluorescence, next generation sequencing (e.g., RNA-Seq techniques), Northern blots, Western blots, Southern blots, NanoString nCounter technologies (e.g., those described in U.S. Patent Application Nos. US 2011/0201515, US 2011/0229888, and US 2013/0017971, each of which is incorporated by reference in its entirety), proteomic techniques (e.g., mass spectrometry or protein arrays), and combinations thereof.

Devices

Devices of the invention can be used for detecting the level of expression of one or more biomarkers shown in Tables 1-4. The device may include at least one single-stranded nucleic acid (e.g., a probe) having at least 85% sequence identity (e.g., 85%, 90%, 95%, 97%, 98%, 99%, or 100% sequence identity) to a nucleic acid sequence that is complementary or identical to at least 5 (e.g., at least 10, at least 15, at least 20, or more) consecutive nucleotides of one or more biomarkers shown in Tables 1-4 (e.g., ATP1B1 (SEQ ID NO: 201 or 219) or IGLC1 (SEQ ID NO: 301, 302, 303, or 318)), in which the at least one single-stranded nucleic acid is sufficient for the detection of the expression level of the one or more biomarkers. The device may be used to detect the expression level of a given biomarker by specific hybridization between the single-stranded nucleic acid and the biomarker (e.g., an mRNA, genomic DNA, or non-coding RNA), a nucleic acid encoding the biomarker (e.g., an mRNA), or a complementary nucleic acid thereof. The device may be or include a microarray. The device may also include or be used with reagents and materials for next generation sequence (e.g., sequencing by synthesis). The device may also include or be used with NanoString reagents and at least one nCounter cartridge. The device may be or include a protein array, which contains one or more protein binding moieties (e.g., proteins, antibodies, nucleic acids, aptamers, affibodies, lipids, phospholipids, small molecules, labeled variants of any of the above, and any other moieties useful for protein detection as well known in the art) capable of detectably binding to the polypeptide product(s) of one or more biomarkers shown in Tables 1-4. The device may also be a cartridge for measuring an amplification product resulting from hybridization between one or more nucleic acid molecules from the patient and at least one single-stranded nucleic acid single-stranded nucleic acid molecules of the device, such as a device for performing qRT-PCR.

Microarrays

The expression levels of the biomarkers (e.g., the biomarkers listed in Tables 1-4 (e.g., ATP1B1 (SEQ ID NO: 201)) may be determined using high-throughput expression profiling platforms, such as microarrays. In particular, a microarray for use in the methods for assessing the responsiveness of a cancer patient (e.g., a patient having cancer that is resistant to one or more cancer therapies other than irofulven) to irofulven contains or is produced by generating oligonucleotide probes (e.g., DNA, cDNA, or RNA probes) capable of hybridizing to one or more biomarkers of interest (e.g., one or more of the biomarkers of Tables 1-4) or the complement sequences thereof. Each probe can have, e.g., at least 10, 15, 20, 25, 30, or more contiguous nucleic acid residues (e.g., at least 15) that are complementary or identical to a nucleic acid sequence of a selected biomarker. The probe nucleic sequence can also have at least 85% (e.g., 90%, 95%, 99%, or 100%) sequence identity to the nucleic acid sequence of the gene coding the biomarker (e.g., ATP1B1 (SEQ ID NO: 201 or 219)) or the complement sequence thereof. In particular, the probe sequences can be complementary to all or a portion of the nucleic acid sequence of the biomarker(s).

For example, microarrays of the invention for determining irofulven responsiveness can include probes for one or more (e.g., at least 5, 10, 15, or 20 or more (e.g., all)) biomarkers of sensitivity shown in Tables 1 and 3, such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), and/or GJA1 (SEQ ID NO: 218). Microarrays for determining irofulven responsiveness can also include probes for one or more (e.g., at least 5, 10, 15, or 20 or more (e.g., all)) biomarkers of resistance listed in Tables 2 and 4, such as IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). Microarrays for determining irofulven responsiveness can also include probes for one or more (e.g., at least 5, 10, 15, or 20 or more (e.g., all)) biomarkers of sensitivity and biomarkers of resistance shown in Tables 1-4, such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321).

A microarray probe may be single-stranded or double-stranded. The probe may be labeled (e.g., detectably labeled with a fluorescent molecule, dye molecule, small molecule, epitope tag, barcode sequence, polypeptide, or any other detectable molecule). Probes can be detectably labeled and immobilized on a solid support to form the microarray. For example, probes can be either prefabricated and spotted to the surface or directly synthesized on to the surface (in situ) of the microarray. The microarray can also be configured such that the sequence and position of each member (e.g., probe) of the array is known. For example, a selection of biomarkers whose expression correlates with an increased likelihood of responsiveness to irofulven can be arrayed on a solid support. Hybridization of a labeled probe with a particular target nucleic acid (e.g., an mRNA corresponding to one or more biomarkers of Tables 1-4) indicates that the sample from which the mRNA was derived expresses that biomarker (e.g., the biomarker of sensitivity or resistance to irofulven).

PCR-Based Techniques

As few as one to thirty (e.g., 5 to 30 or 10 to 30, or at least the first 15 of the biomarkers listed in Tables 1-2) biomarkers may be used to determine patient responsiveness to irofulven using the methods described herein. Tissue or cell samples from a cancer patient (e.g., a patient having cancer that is resistant to one or more cancer therapies other than irofulven) can be conveniently assayed for gene expression levels using polymerase chain reaction (PCR) analysis, such as quantitative real-time PCR (qPCR), or quantitative loop-mediated isothermal amplification (q-LAMP). For example, an mRNA corresponding to a biomarker of Tables 1-4 can be detected in a biological sample by (a) producing cDNA from the sample by reverse transcription using at least one primer; (b) amplifying the cDNA so produced using a target polynucleotide as sense and antisense primers to amplify target cDNAs therein; and (c) detecting the presence of the amplified target cDNA using polynucleotide probes. The primers and probes including the target sequences shown in Tables 1-4, such as ATP1B1 (SEQ ID NO: 201 or 219) and/or IGLC1 (SEQ ID NO: 301, 302, 303, or 318), may be used to detect expression of one or more of the indicated biomarkers using PCR. The methods can include one or more steps that allow determination of the levels of target mRNA in a biological sample (e.g., by simultaneously examining the levels of a comparative control mRNA sequence or "housekeeping" gene, such as an actin family member or GAPDH). The primers for these PCR-based assays may be labeled for detection according to methods known in the art.

Sequencing

The expression levels of the biomarkers shown in Tables 1-4, such as ATP1B1 (SEQ ID NO: 201 or 219) and/or IGLC1 (SEQ ID NO: 301, 302, 303, or 318), may be determined using sequencing technologies, such as next generation sequencing platforms (e.g., RNA-Seq), as described in Mortazavi et al., Nat. Methods 5: 621-628, 2008, hereby incorporated by reference. RNA-Seq is a robust technology for monitoring expression by direct sequencing of the RNA molecules in a sample. This methodology may include fragmentation of RNA to an average length of, e.g., 200 nucleotides, conversion to cDNA by random priming, and synthesis of double-stranded cDNA (e.g., using the PROTOSCRIPT® First Strand cDNA Synthesis Kit from New England Biosciences). The cDNA may then be converted into a molecular library for sequencing by addition of sequence adapters for each library (e.g., from ILLUMINA®/Solexa), and the resulting 50 to 100 nucleotide reads are mapped onto the genome. Exemplary sequencing platforms suitable for use according to the methods include, e.g., pyrosequencing, ILLUMINA® sequencing by synthesis, SOLID® sequencing, ION TORRENT® sequencing, and SMRT® sequencing.

Methods of Determining the Responsiveness of a Patient to Irofulven

The invention features diagnostic methods for the detection and screening of cancer patients (e.g., a patient having cancer that is resistant to one or more cancer therapies other than irofulven) that may be responsive to irofulven using one or more of the biomarkers shown in Tables 1-4 (e.g., ATP1B1 (SEQ ID NO: 201 or 219) or IGLC1 (SEQ ID NO: 301, 302, 303, or 318)). The methods of the invention may be used for predicting a patient's responsiveness to irofulven, and optionally, treating the cancer patient throughout the progression of cancer and/or in cases of recurrence (e.g., after a first line treatment, a second line treatment, and/or a third line treatment).

The invention provides individual biomarkers (e.g., ATP1B1 (SEQ ID NO: 201)) and sets of biomarkers (e.g., two or more of the biomarkers listed in Tables 1-4), the expression levels of which, as detected in a biological sample (e.g., a tumor sample, such as a biopsy) obtained from a cancer patient (e.g., a human with cancer), are indicative of responsiveness to irofulven. The biomarkers were identified using methods similar to those previously described in, e.g., Chen et al. (*Mol. Cancer Ther.* 11:34-33, 2012), Wang et al. (*J. Nat. Cancer Inst.* 105: 1284-1291, 2013), and Knudsen et al. (*PLoS One,* 9: e87415, 2014), each of which are incorporated by reference herein in their entirety. In particular, an algorithm based on growth inhibition values (GI50) of a cell line (e.g., NCI60 cells) is subjected to treatment with irofulven and gene expression is determined (e.g., by microarray analysis, reverse transcriptase polymerase chain reaction (RT-PCR), quantitative real-time PCR (qPCR), or next generation sequencing). After normalization, genes with, e.g., a Pearson correlation coefficient greater than about 0.2 or below about –0.2 can be classified as biomarkers of sensitivity or resistance, respectively. In particular, a correlation coefficient of about 0.2 or greater is a statistically significant cut-off known in the art for establishing whether the expression level of A GENE, e.g., the genes shown in Tables 1-4, correlate with the likelihood of cancer treatment sensitivity, such as sensitivity to irofulven. Thus, a correlation coefficient of about 0.2 or greater or about –0.2 or lower can be used to estimate the statistical significance of the expression level of the genes of Tables 1-4 for predicting patient responsiveness to treatment with irofulven according to the methods described herein.

Comparison of Biomarker Expression Levels

One or more biomarkers of sensitivity and/or resistance, identified as described herein, can be used to predict responsiveness to irofulven by measuring the expression level of the biomarkers in a biological sample obtained from the cancer patient. A single biomarker (e.g., any of the biomarkers of Tables 1-4, such as ATP1B1 (SEQ ID NO: 201)) may be used to determine the responsiveness of a cancer patient (e.g., a patient having cancer that is resistant to one or more cancer therapies other than irofulven) to irofulven. After determining the expression level of the biomarker(s) in a sample (e.g., a tumor sample) from the cancer patient, the expression level of the biomarker(s) in the sample may be compared to the expression level of the biomarker(s) in a cell (e.g., a cancer cell) or tissue (e.g., a tumor tissue) known to be sensitive to treatment with irofulven. If the expression level of the biomarker(s) in the sample from the cancer patient is substantially similar (e.g., identical to or has the same trend of expression level) to the expression level of the biomarker(s) in the cell or tissue known to be sensitive to irofulven, then the cancer patient is predicted to be responsive to treatment with irofulven. Alternatively, if the expression level of the biomarker(s) in the sample from the cancer patient is substantially dissimilar to the expression level of the biomarker(s) in the cell or tissue known to be sensitive to irofulven, then the cancer patient is predicted to be non-responsive to treatment with irofulven.

The expression level of the biomarker (e.g., ATP1B1 (SEQ ID NO: 201)) in a sample from the cancer patient may also be compared to the expression level of the biomarker in a cell (e.g., a cancer cell) or tissue (e.g., a tumor tissue) known to be resistant to treatment with irofulven. If the expression level of the biomarker in the sample from the cancer patient is substantially similar to the expression level of the biomarker in the cell or tissue known to be resistant to irofulven, then the cancer patient is predicted to be non-responsive to treatment with irofulven. Alternatively, if the expression level of the biomarker in the sample from the cancer patient is substantially dissimilar to the expression level of the biomarker in the cell or tissue known to be sensitive to irofulven, then the cancer patient is predicted to be responsive to treatment with irofulven.

The responsiveness of a cancer patient (e.g., a patient having cancer that is resistant to one or more cancer therapies other than irofulven) to irofulven can also be predicted by comparing the expression level of a biomarker (e.g., ATP1B1 (SEQ ID NO: 201)) to the expression level of the biomarker in one or more cells or tissues (e.g., from a cancer patient population) known to be sensitive to treatment with irofulven and one or more cells or tissues (e.g., from a cancer patient population) known to be resistant to treatment with irofulven. In particular, the patient may be responsive to treatment with irofulven if the expression level of the biomarker is more similar to the expression level of the biomarker in a cell or tissue known to be sensitive to treatment with irofulven than to a cell or tissue known to be resistant to treatment with irofulven. Alternatively, the patient may be non-responsive to treatment with irofulven if the expression level of the biomarker is more similar to the expression level of the biomarker in a cell or tissue known to be resistant to treatment with irofulven than to a cell or tissue known to be sensitive to treatment with irofulven.

Additionally, one or more biomarkers of sensitivity (e.g., one or more of ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), and GJA1 (SEQ ID NO: 218)) and one or more biomarkers of resistance (e.g., one or more of IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and GTSF1 (SEQ ID NO: 321)) may be used in combination to determine the responsiveness of a cancer patient (e.g., a patient having cancer that is resistant to one or more cancer therapies other than irofulven) to treatment with irofulven. For example, the predicted responsiveness of a cancer patient may be determined from, e.g., the difference score, which may be defined as the difference between the mean of the expression level of the one or more biomarkers of sensitivity of Tables 1 and 3 and the mean of the expression level of the one or more biomarkers of resistance of Tables 2 and 4.

The difference score of the cancer patient can then be compared to the difference score based on the expression level of the biomarkers in a cell (e.g., a cancer cell) or tissue (e.g., a tumor tissue) known to be sensitive or resistant to treatment with irofulven. In particular, the patient may be responsive to treatment with irofulven if the difference score is substantially similar to the expression level of the biomarkers in a cell or tissue known to be sensitive to treatment with irofulven. Alternatively, the patient may be non-responsive to treatment with irofulven if the difference score is substantially similar to the expression level of the biomarkers in a cell or tissue known to be resistant to treatment with irofulven. Additionally, the patient may be responsive to treatment with irofulven if the difference score is substantially similar to the expression level of the biomarkers in a cell or tissue known to be sensitive to treatment with irofulven than a cell or tissue known to be resistant to treatment with irofulven. Alternatively, the patient may be non-responsive to treatment with irofulven if the difference score is substantially similar to the expression level of the biomarkers in a cell or tissue known to be resistant to treatment with irofulven than a cell or tissue known to be sensitive to treatment with irofulven.

One or more biomarkers of sensitivity and/or resistance, identified as described herein, can be used to predict responsiveness to irofulven by measuring the expression level of the biomarkers in a biological sample obtained from the cancer patient. A single biomarker (e.g., any of the biomarkers of Tables 1-4, such as ATP1B1 (SEQ ID NO: 201)) may be used to determine the responsiveness of a cancer patient (e.g., a patient having cancer that is resistant to one or more cancer therapies other than irofulven) to irofulven. After determining the expression level of the biomarker(s) in a sample (e.g., a tumor sample) from the cancer patient, the expression level of the biomarker(s) in the sample may be compared to the expression level of the biomarker(s) in a cell (e.g., a cancer cell) or tissue (e.g., a tumor tissue) known to be sensitive to treatment with irofulven. If the expression level of the biomarker(s) in the sample from the cancer patient corresponds to (e.g., is identical to or has the same trend of expression level as) the expression level of the biomarker(s) in the cell or tissue known to be sensitive to irofulven, then the cancer patient is predicted to be responsive to treatment with irofulven. Alternatively, if the expression level of the biomarker(s) in the sample from the cancer patient is substantially dissimilar to the expression level of the biomarker(s) in the cell or tissue known to be sensitive to irofulven, then the cancer patient is predicted to be non-responsive to treatment with irofulven.

The expression level of the biomarker (e.g., ATP1B1 (SEQ ID NO: 201)) in a sample from the cancer patient may also be compared to the expression level of the biomarker in a cell (e.g., a cancer cell) or tissue (e.g., a tumor tissue) known to be resistant to treatment with irofulven. If the expression level of the biomarker in the sample from the cancer patient corresponds to the expression level of the biomarker in the cell or tissue known to be resistant to irofulven, then the cancer patient is predicted to be non-responsive to treatment with irofulven. Alternatively, if the expression level of the biomarker in the sample from the cancer patient is substantially dissimilar to the expression level of the biomarker in the cell or tissue known to be resistant to irofulven, then the cancer patient is predicted to be responsive to treatment with irofulven.

The responsiveness of a cancer patient (e.g., a patient having cancer that is resistant to one or more cancer therapies other than irofulven) to irofulven can also be predicted by comparing the expression level of a biomarker (e.g., ATP1B1 (SEQ ID NO: 201)) to the expression level of the biomarker in one or more cells or tissues (e.g., from a cancer patient population) known to be sensitive to treatment with irofulven and one or more cells or tissues (e.g., from a cancer patient population) known to be resistant to treatment with irofulven. In particular, the patient may be responsive to treatment with irofulven if the expression level of the biomarker(s) corresponds to the expression level of the biomarker(s) in a cell or tissue known to be sensitive to treatment with irofulven relative to the expression level of the biomarkers in a cell or tissue known to be resistant to treatment with irofulven. Alternatively, the patient may be non-responsive to treatment with irofulven if the expression level of the biomarker(s) corresponds to the expression level of the biomarker(s) in a cell or tissue known to be resistant to treatment with irofulven relative to the expression level of the biomarkers in a cell or tissue known to be resistant to treatment with irofulven.

Additionally, one or more biomarkers of sensitivity (e.g., one or more of ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), and GJA1 (SEQ ID NO: 218)) and one or more biomarkers of resistance (e.g., one or more of IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and GTSF1 (SEQ ID NO: 321)) may be used in combination to determine the responsiveness of a cancer patient (e.g., a patient having cancer that is resistant to one or more cancer therapies other than irofulven) to treatment with irofulven. For example, the predicted responsiveness of a cancer patient may be determined from, e.g., the difference score, which may be defined as the difference between the mean of the expression level of the one or more biomarkers of sensitivity of Tables 1 and 3 and the mean of the expression level of the one or more biomarkers of resistance of Tables 2 and 4.

The difference score of the cancer patient can then be compared to the difference score based on the expression level of the biomarkers in a cell (e.g., a cancer cell) or tissue (e.g., a tumor tissue) known to be sensitive or resistant to treatment with irofulven. In particular, the patient may be responsive to treatment with irofulven if the difference score corresponds to the expression level of the biomarkers in a cell or tissue known to be sensitive to treatment with irofulven. Alternatively, the patient may be non-responsive to treatment with irofulven if the difference score corresponds to the expression level of the biomarkers in a cell or tissue known to be resistant to treatment with irofulven. Additionally, the patient may be responsive to treatment with irofulven if the difference score corresponds to the expression level of the biomarkers in a cell or tissue known to be sensitive to treatment with irofulven relative to the expression level of the biomarkers in a cell or tissue known to be resistant to treatment with irofulven. Alternatively, the patient may be non-responsive to treatment with irofulven if the difference score corresponds to the expression level of the biomarkers in a cell or tissue known to be resistant to treatment with irofulven relative to the expression level of the biomarkers in a cell or tissue known to be sensitive to treatment with irofulven.

Preferably, the cell or tissue known to be either sensitive or resistant to irofulven is of the same cancer type as the cancer patient with an unknown responsiveness to irofulven. For example, the cancer patient and the cell or tissue known to be either sensitive or resistant to irofulven may both have a cancer type selected from a solid tumor or a hematological cancer, e.g., prostate cancer, ovarian cancer (e.g., ovarian adenocarcinoma or embryonal carcinoma), liver cancer (e.g., hepatocellular carcinoma (HCC) or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. In particular, the cancer of the patient and the cell or tissue with known resistance or sensitivity to irofulven is, e.g., prostate cancer, ovarian cancer, hepatocellular carcinoma (HCC), multiple myeloma, breast cancer, acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), Hodgkin's lymphoma, cervical cancer, renal cell carcinoma (RCC), esophageal cancer, melanoma, glioma, pancreatic cancer, gastrointestinal stromal tumors (GIST), sarcoma, estrogen receptor-positive (ERpos) breast cancer, non-small cell lung carcinoma (NSCLC), colon cancer, bladder cancer, or squamous cell carcinoma of the head and neck (SCCHN).

Machine learning techniques such as Neural Networks, Support Vector Machines, K Nearest Neighbor, and Nearest Centroids may also be employed to develop models that discriminate patients sensitive to treatment with irofulven from those resistant to treatment with irofulven using biomarker expression as model variables which assign each patient a classification as sensitive or resistant to treatment with irofulven. Machine learning techniques used to classify patients using various measurements are described in U.S. Pat. No. 5,822,715; U.S. Patent Application Publication Nos. 2003/0073083, 2005/0227266, 2005/0208512, 2005/0123945, 2003/0129629, and 2002/0006613; and in Vapnik V N. Statistical Learning Theory, John Wiley & Sons, New York, 1998; Hastie et al., 2001, The Elements of Statistical Learning: Data Mining, Inference, and Prediction, Springer, N.Y.; Agresti, 1996, An Introduction to Categorical Data Analysis, John Wiley & Sons, New York; V. Tresp et al., "Neural Network Modeling of Physiological Processes," in Hanson S. J. et al. (Eds.), Computational Learning Theory and Natural Learning Systems 2, MIT Press, 1994, each of which are hereby incorporated by reference in their entirety.

Biomarkers of Sensitivity and Resistance

The expression levels of one or more biomarkers of Tables 1-4 can be used to determine cancer patient responsiveness to treatment with irofulven. Once determined to be responsive, the patient can be treated with irofulven. In particular, the biomarker ATP1B1 (SEQ ID NO: 201 or 219) may be used to assess a cancer patient's (e.g, a patient having cancer that is resistant to one or more cancer therapies other than irofulven) responsiveness to irofulven. The expression level of the biomarker ATP1B1 (SEQ ID NO: 201 or 219) may be assessed using nucleic acid amplification methods (e.g., PCR) or a device (e.g., a microarray). As is described above, the expression level of ATP1B1 (SEQ ID NO: 201 or 219) in the patient sample may then be compared, e.g., to the expression level of ATP1B1 (SEQ ID NO: 201 or 219) in a cell (e.g., a cancer cell) or tissue (e.g., a tumor tissue) known to be sensitive or resistant to treatment with irofulven and used to determine the cancer patient's responsiveness to irofulven. The biomarker ATP1B1 (SEQ ID NO: 201 or 219) may be used alone to predict cancer patient responsiveness to treatment with irofulven or in combination with one or more additional biomarkers (e.g., one, two, three, four, five, ten, or all of the biomarkers shown in Tables 1-4), such as UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The expression level of the biomarker UCHL1 (SEQ ID NO: 202) may be assessed using nucleic acid amplification methods (e.g., PCR) or a device (e.g., a microarray). As is described above, the expression level of UCHL1 (SEQ ID NO: 202) in the patient sample may then be compared, e.g., to the expression level of UCHL1 (SEQ ID NO: 202) in a cell (e.g., a cancer cell) or tissue (e.g., a tumor tissue) known to be sensitive or resistant to treatment with irofulven and used to determine the cancer patient's responsiveness to irofulven. The biomarker UCHL1 (SEQ ID NO: 202) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker PTGR1 (SEQ ID NO: 203 or 210) may be used to assess a cancer patient's (e.g, a patient having cancer that is resistant to one or more cancer therapies other than irofulven) responsiveness to irofulven. The expression level of the biomarker PTGR1 (SEQ ID NO: 203 or 210) may be assessed using nucleic acid amplification methods (e.g., PCR) or a device (e.g., a microarray). As is described above, the expression level of PTGR1 (SEQ ID NO: 203 or 210) in the patient sample may then be compared, e.g., to the expression level of PTGR1 (SEQ ID NO: 203 or 210) in a cell (e.g., a cancer cell) or tissue (e.g., a tumor tissue) known to be sensitive or resistant to treatment with irofulven and used to determine the cancer patient's responsiveness to irofulven. The biomarker PTGR1 (SEQ ID NO: 203 or 210) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker NME7 (SEQ ID NO: 204) may be used to assess a cancer patient's (e.g, a patient having cancer that is resistant to one or more cancer therapies other than irofulven) responsiveness to irofulven. The expression level of the biomarker NME7 (SEQ ID NO: 204) may be assessed using nucleic acid amplification methods (e.g., PCR) or a device (e.g., a microarray). As is described above, the expression level of NME7 (SEQ ID NO: 204) in the patient sample may then be compared, e.g., to the expression level of NME7 (SEQ ID NO: 204) in a cell (e.g., a cancer cell) or tissue (e.g., a tumor tissue) known to be sensitive or resistant to treatment with irofulven and used to determine the cancer patient's responsiveness to irofulven. The biomarker NME7 (SEQ ID NO: 204) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker PLS3 (SEQ ID NO: 205) may be used to assess a cancer patient's (e.g, a patient having cancer that is resistant to one or more cancer therapies other than irofulven) responsiveness to irofulven. The expression level of the biomarker PLS3 (SEQ ID NO: 205) may be assessed using nucleic acid amplification methods (e.g., PCR) or a device (e.g., a microarray). As is described above, the expression level of PLS3 (SEQ ID NO: 205) in the patient sample may then be compared, e.g., to the expression level of PLS3 (SEQ ID NO: 205) in a cell (e.g., a cancer cell) or tissue (e.g., a tumor tissue) known to be sensitive or resistant to treatment with irofulven and used to determine the cancer patient's responsiveness to irofulven. The biomarker PLS3 (SEQ ID NO: 205) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3

(SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker S100A10 (SEQ ID NO: 206) may be used to assess a cancer patient's (e.g, a patient having cancer that is resistant to one or more cancer therapies other than irofulven) responsiveness to irofulven. The expression level of the biomarker S100A10 (SEQ ID NO: 206) may be assessed using nucleic acid amplification methods (e.g., PCR) or a device (e.g., a microarray). As is described above, the expression level of S100A10 (SEQ ID NO: 206) in the patient sample may then be compared, e.g., to the expression level of S100A10 (SEQ ID NO: 206) in a cell (e.g., a cancer cell) or tissue (e.g., a tumor tissue) known to be sensitive or resistant to treatment with irofulven and used to determine the cancer patient's responsiveness to irofulven. The biomarker S100A10 (SEQ ID NO: 206) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker CD24 (SEQ ID NO: 207, 209, or 220) may be used to assess a cancer patient's (e.g, a patient having cancer that is resistant to one or more cancer therapies other than irofulven) responsiveness to irofulven. The expression level of the biomarker CD24 (SEQ ID NO: 207, 209, or 220) may be assessed using nucleic acid amplification methods (e.g., PCR) or a device (e.g., a microarray). As is described above, the expression level of CD24 (SEQ ID NO: 207, 209, or 220) in the patient sample may then be compared, e.g., to the expression level of CD24 (SEQ ID NO: 207, 209, or 220) in a cell (e.g., a cancer cell) or tissue (e.g., a tumor tissue) known to be sensitive or resistant to treatment with irofulven and used to determine the cancer patient's responsiveness to irofulven. The biomarker CD24 (SEQ ID NO: 207, 209, or 220) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker NQO1 (SEQ ID NO: 208 or 216) may be used to assess a cancer patient's (e.g, a patient having cancer that is resistant to one or more cancer therapies other than irofulven) responsiveness to irofulven. The expression level of the biomarker NQO1 (SEQ ID NO: 208 or 216) may be assessed using nucleic acid amplification methods (e.g., PCR) or a device (e.g., a microarray). As is described above, the expression level of NQO1 (SEQ ID NO: 208 or 216) in the patient sample may then be compared, e.g., to the expression level of NQO1 (SEQ ID NO: 208 or 216) in a cell (e.g., a cancer cell) or tissue (e.g., a tumor tissue) known to be sensitive or resistant to treatment with irofulven and used to determine the cancer patient's responsiveness to irofulven. The biomarker NQO1 (SEQ ID NO: 208 or 216) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The expression levels of one or more biomarkers of Tables 1-4 can be used to determine cancer patient responsiveness to treatment with irofulven. Once determined to be responsive, the patient can be treated with irofulven. In particular, the biomarker MYOF (SEQ ID NO: 211) may be used to assess a cancer patient's (e.g, a patient having cancer that is resistant to one or more cancer therapies other than irofulven) responsiveness to irofulven. The expression level of the biomarker MYOF (SEQ ID NO: 211) may be assessed using nucleic acid amplification methods (e.g., PCR) or a device (e.g., a microarray). As is described above, the expression level of MYOF (SEQ ID NO: 211) in the patient sample may then be compared, e.g., to the expression level of MYOF (SEQ ID NO: 211) in a cell (e.g., a cancer cell) or tissue (e.g., a tumor tissue) known to be sensitive or resistant to treatment with irofulven and used to determine the cancer patient's responsiveness to irofulven. The biomarker MYOF (SEQ ID NO: 211) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker LAPTM4B (SEQ ID NO: 212) may be used to assess a cancer patient's (e.g, a patient having cancer that is resistant to one or more cancer therapies other than irofulven) responsiveness to irofulven. The expression level of the biomarker LAPTM4B (SEQ ID NO: 212) may be assessed using nucleic acid amplification methods (e.g., PCR) or a device (e.g., a microarray). As is described above, the expression level of LAPTM4B (SEQ ID NO: 212) in the patient sample may then be compared, e.g., to the expression level of LAPTM4B (SEQ ID NO: 212) in a cell (e.g., a cancer cell) or tissue (e.g., a tumor tissue) known to be sensitive or resistant to treatment with irofulven and used to determine the cancer patient's responsiveness to irofulven. The biomarker LAPTM4B (SEQ ID NO: 212) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker CALD1 (SEQ ID NO: 213) may be used to assess a cancer patient's (e.g, a patient having cancer that is resistant to one or more cancer therapies other than irofulven) responsiveness to irofulven. The expression level of the biomarker CALD1 (SEQ ID NO: 213) may be assessed using nucleic acid amplification methods (e.g., PCR) or a device (e.g., a microarray). As is described above, the expression level of CALD1 (SEQ ID NO: 213) in the patient sample may then be compared, e.g., to the expression level of CALD1 (SEQ ID NO: 213) in a cell (e.g., a cancer cell) or tissue (e.g., a tumor tissue) known to be sensitive or resistant to treatment with irofulven and used to determine the cancer patient's responsiveness to irofulven. The biomarker CALD1 (SEQ ID NO: 213) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker PDGFC (SEQ ID NO: 214) may be used to assess a cancer patient's (e.g, a patient having cancer that is resistant to one or more cancer therapies other than irofulven) responsiveness to irofulven. The expression level of the biomarker PDGFC (SEQ ID NO: 214) may be assessed using nucleic acid amplification methods (e.g., PCR) or a device (e.g., a microarray). As is described above, the expression level of PDGFC (SEQ ID NO: 214) in the patient sample may then be compared, e.g., to the expression level of PDGFC (SEQ ID NO: 214) in a cell (e.g., a cancer cell) or tissue (e.g., a tumor tissue) known to be sensitive or resistant to treatment with irofulven and used to determine the cancer patient's responsiveness to irofulven. The biomarker PDGFC (SEQ ID NO: 214) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker BASP1 (SEQ ID NO: 215) may be used to assess a cancer patient's (e.g, a patient having cancer that is resistant to one or more cancer therapies other than irofulven) responsiveness to irofulven. The expression level of the biomarker BASP1 (SEQ ID NO: 215) may be assessed using nucleic acid amplification methods (e.g., PCR) or a device (e.g., a microarray). As is described above, the expression level of BASP1 (SEQ ID NO: 215) in the patient sample may then be compared, e.g., to the expression level of BASP1 (SEQ ID NO: 215) in a cell (e.g., a cancer cell) or tissue (e.g., a tumor tissue) known to be sensitive or resistant to treatment with irofulven and used to determine the cancer patient's responsiveness to irofulven. The biomarker BASP1 (SEQ ID NO: 215) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker ID1 (SEQ ID NO: 217) may be used to assess a cancer patient's (e.g, a patient having cancer that is resistant to one or more cancer therapies other than irofulven) responsiveness to irofulven. The expression level of the biomarker ID1 (SEQ ID NO: 217) may be assessed using nucleic acid amplification methods (e.g., PCR) or a device (e.g., a microarray). As is described above, the expression level of ID1 (SEQ ID NO: 217) in the patient sample may then be compared, e.g., to the expression level of ID1 (SEQ ID NO: 217) in a cell (e.g., a cancer cell) or tissue (e.g., a tumor tissue) known to be sensitive or resistant to treatment with irofulven and used to determine the cancer patient's responsiveness to irofulven. The biomarker ID1 (SEQ ID NO: 217) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker GJA1 (SEQ ID NO: 218) may be used to assess a cancer patient's (e.g, a patient having cancer that is resistant to one or more cancer therapies other than irofulven) responsiveness to irofulven. The expression level of the biomarker GJA1 (SEQ ID NO: 218) may be assessed using nucleic acid amplification methods (e.g., PCR) or a device (e.g., a microarray). As is described above, the expression level of GJA1 (SEQ ID NO: 218) in the patient sample may then be compared, e.g., to the expression level of GJA1 (SEQ ID NO: 218) in a cell (e.g., a cancer cell) or tissue (e.g., a tumor tissue) known to be sensitive or resistant to treatment with irofulven and used to determine the cancer patient's responsiveness to irofulven. The biomarker GJA1 (SEQ ID NO: 218) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker IGLC1 (SEQ ID NO: 301, 302, 303, or 318) may be used to assess a cancer patient's (e.g, a patient having cancer that is resistant to one or more cancer therapies other than irofulven) responsiveness to irofulven. The expression level of the biomarker IGLC1 (SEQ ID NO: 301, 302, 303, or 318) may be assessed using nucleic acid amplification methods (e.g., PCR) or a device (e.g., a microarray). As is described above, the expression level of IGLC1 (SEQ ID NO: 301, 302, 303, or 318) in the patient sample may then be compared, e.g., to the expression level of IGLC1 (SEQ ID NO: 301, 302, 303, or 318) in a cell (e.g., a cancer cell) or tissue (e.g., a tumor tissue) known to be sensitive or resistant to treatment with irofulven and used to determine the cancer patient's responsiveness to irofulven. The biomarker IGLC1 (SEQ ID NO: 301, 302, 303, or 318) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker LAPTM5 (SEQ ID NO: 304 or 338) may be used to assess a cancer patient's (e.g, a patient having cancer that is resistant to one or more cancer therapies other than irofulven) responsiveness to irofulven. The expression level of the biomarker LAPTM5 (SEQ ID NO: 304 or 338) may be assessed using nucleic acid amplification methods (e.g., PCR) or a device (e.g., a microarray). As is described above, the expression level of LAPTM5 (SEQ ID NO: 304 or 338) in the patient sample may then be compared, e.g., to the expression level of LAPTM5 (SEQ ID NO: 304 or 338) in a cell (e.g., a cancer cell) or tissue (e.g., a tumor tissue) known to be sensitive or resistant to treatment with irofulven and used to determine the cancer patient's responsiveness to irofulven. The biomarker LAPTM5 (SEQ ID NO: 304 or 338) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker ARHGDIB (SEQ ID NO: 305 or 311) may be used to assess a cancer patient's (e.g, a patient having cancer that is resistant to one or more cancer therapies other than irofulven) responsiveness to irofulven. The expression level of the biomarker ARHGDIB (SEQ ID NO: 305 or 311) may be assessed using nucleic acid amplification methods (e.g., PCR) or a device (e.g., a microarray). As is described above, the expression level of ARHGDIB (SEQ ID NO: 305 or 311) in the patient sample may then be compared, e.g., to the expression level of ARHGDIB (SEQ ID NO: 305 or 311) in a cell (e.g., a cancer cell) or tissue (e.g., a tumor tissue) known to be sensitive or resistant to treatment with irofulven and used to determine the cancer patient's responsiveness to irofulven. The biomarker ARHGDIB (SEQ ID NO: 305 or 311) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker SLC43A3 (SEQ ID NO: 307) may be used to assess a cancer patient's (e.g, a patient having cancer that is resistant to one or more cancer therapies other than irofulven) responsiveness to irofulven. The expression level of the biomarker SLC43A3 (SEQ ID NO: 307) may be assessed using nucleic acid amplification methods (e.g., PCR) or a device (e.g., a microarray). As is described above, the expression level of SLC43A3 (SEQ ID NO: 307) in the patient sample may then be compared, e.g., to the expression level of SLC43A3 (SEQ ID NO: 307) in a cell (e.g., a cancer cell) or tissue (e.g., a tumor tissue) known to be sensitive or resistant to treatment with irofulven and used to determine the cancer patient's responsiveness to irofulven. The biomarker SLC43A3 (SEQ ID NO: 307) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker LCP1 (SEQ ID NO: 308) may be used to assess a cancer patient's (e.g, a patient having cancer that is resistant to one or more cancer therapies other than irofulven) responsiveness to irofulven. The expression level of the biomarker LCP1 (SEQ ID NO: 308) may be assessed using nucleic acid amplification methods (e.g., PCR) or a device (e.g., a microarray). As is described above, the expression level of LCP1 (SEQ ID NO: 308) in the patient sample may then be compared, e.g., to the expression level of LCP1 (SEQ ID NO: 308) in a cell (e.g., a cancer cell) or tissue (e.g., a tumor tissue) known to be sensitive or resistant to treatment with irofulven and used to determine the cancer patient's responsiveness to irofulven. The biomarker LCP1 (SEQ ID NO: 308) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker HCLS1 (SEQ ID NO: 309) may be used to assess a cancer patient's (e.g, a patient having cancer that is resistant to one or more cancer therapies other than irofulven) responsiveness to irofulven. The expression level of the biomarker HCLS1 (SEQ ID NO: 309) may be assessed using nucleic acid amplification methods (e.g., PCR) or a device (e.g., a microarray). As is described above, the expression level of HCLS1 (SEQ ID NO: 309) in the patient sample may then be compared, e.g., to the expression level of HCLS1 (SEQ ID NO: 309) in a cell (e.g., a cancer cell) or tissue (e.g., a tumor tissue) known to be sensitive or resistant to treatment with irofulven and used to determine the cancer patient's responsiveness to irofulven. The biomarker HCLS1 (SEQ ID NO: 309) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker CD53 (SEQ ID NO: 310) may be used to assess a cancer patient's (e.g, a patient having cancer that is resistant to one or more cancer therapies other than irofulven) responsiveness to irofulven. The expression level of the biomarker CD53 (SEQ ID NO: 310) may be assessed using nucleic acid amplification methods (e.g., PCR) or a device (e.g., a microarray). As is described above, the expression level of CD53 (SEQ ID NO: 310) in the patient sample may then be compared, e.g., to the expression level of CD53 (SEQ ID NO: 310) in a cell (e.g., a cancer cell) or tissue (e.g., a tumor tissue) known to be sensitive or resistant to treatment with irofulven and used to determine the cancer patient's responsiveness to irofulven. The biomarker CD53 (SEQ ID NO: 310) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker MZB1 (SEQ ID NO: 313) may be used to assess a cancer patient's (e.g, a patient having cancer that is resistant to one or more cancer therapies other than irofulven) responsiveness to irofulven. The expression level of the biomarker MZB1 (SEQ ID NO: 313) may be assessed using nucleic acid amplification methods (e.g., PCR) or a device (e.g., a microarray). As is described above, the expression level of MZB1 (SEQ ID NO: 313) in the patient sample may then be compared, e.g., to the expression level of MZB1 (SEQ ID NO: 313) in a cell (e.g., a cancer cell) or tissue (e.g., a tumor tissue) known to be sensitive or resistant to treatment with irofulven and used to determine the cancer patient's responsiveness to irofulven. The biomarker MZB1 (SEQ ID NO: 313) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker RASSF5 (SEQ ID NO: 314 or 386) may be used to assess a cancer patient's (e.g, a patient having cancer that is resistant to one or more cancer therapies other than irofulven) responsiveness to irofulven. The expression level of the biomarker RASSF5 (SEQ ID NO: 314 or 386) may be assessed using nucleic acid amplification methods (e.g., PCR) or a device (e.g., a microarray). As is described above, the expression level of RASSF5 (SEQ ID NO: 314 or 386) in the patient sample may then be compared, e.g., to the expression level of RASSF5 (SEQ ID NO: 314 or 386) in a cell (e.g., a cancer cell) or tissue (e.g., a tumor tissue) known to be sensitive or resistant to treatment with irofulven and used to determine the cancer patient's responsiveness to irofulven. The biomarker RASSF5 (SEQ ID NO: 314 or 386) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker FAM46C (SEQ ID NO: 315) may be used to assess a cancer patient's (e.g, a patient having cancer that is resistant to one or more cancer therapies other than irofulven) responsiveness to irofulven. The expression level of the biomarker FAM46C (SEQ ID NO: 315) may be assessed using nucleic acid amplification methods (e.g., PCR) or a device (e.g., a microarray). As is described above, the expression level of FAM46C (SEQ ID NO: 315) in the patient sample may then be compared, e.g., to the expression level of FAM46C (SEQ ID NO: 315) in a cell (e.g., a cancer cell) or tissue (e.g., a tumor tissue) known to be sensitive or resistant to treatment with irofulven and used to determine the cancer patient's responsiveness to irofulven. The biomarker FAM46C (SEQ ID NO: 315) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FRCSD1 (SEQ ID NO: 316), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker RCSD1 (SEQ ID NO: 316) may be used to assess a cancer patient's (e.g, a patient having cancer that is resistant to one or more cancer therapies other than irofulven) responsiveness to irofulven. The expression level of the biomarker RCSD1 (SEQ ID NO: 316) may be assessed using nucleic acid amplification methods (e.g., PCR) or a device (e.g., a microarray). As is described above, the expression level of RCSD1 (SEQ ID NO: 316) in the patient sample may then be compared, e.g., to the expression level of RCSD1 (SEQ ID NO: 316) in a cell (e.g., a cancer cell) or tissue (e.g., a tumor tissue) known to be sensitive or resistant to treatment with irofulven and used to determine the cancer patient's responsiveness to irofulven. The biomarker RCSD1 (SEQ ID NO: 316) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), IGJ (SEQ ID NO: 317), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker IGJ (SEQ ID NO: 317) may be used to assess a cancer patient's (e.g, a patient having cancer that is resistant to one or more cancer therapies other than irofulven) responsiveness to irofulven. The expression level of the biomarker IGJ (SEQ ID NO: 317) may be assessed using nucleic acid amplification methods (e.g., PCR) or a device (e.g., a microarray). As is described above, the expression level of IGJ (SEQ ID NO: 317) in the patient sample may then be compared, e.g., to the expression level of IGJ (SEQ ID NO: 317) in a cell (e.g., a cancer cell) or tissue (e.g., a tumor tissue) known to be sensitive or resistant to treatment with irofulven and used to determine the cancer patient's responsiveness to irofulven. The biomarker IGJ (SEQ ID NO: 317) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), LPXN (SEQ ID NO: 319), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker LPXN (SEQ ID NO: 319) may be used to assess a cancer patient's (e.g, a patient having cancer that is resistant to one or more cancer therapies other than irofulven) responsiveness to irofulven. The expression level of the biomarker LPXN (SEQ ID NO: 319) may be assessed using nucleic acid amplification methods (e.g., PCR) or a device (e.g., a microarray). As is described above, the expression level of LPXN (SEQ ID NO: 319) in the patient sample may then be compared, e.g., to the expression level of LPXN (SEQ ID NO: 319) in a cell (e.g., a cancer cell) or tissue (e.g., a tumor tissue) known to be sensitive or resistant to treatment with irofulven and used to determine the cancer patient's responsiveness to irofulven. The biomarker LPXN (SEQ ID NO: 319) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), ITGB7 (SEQ ID NO: 320), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker ITGB7 (SEQ ID NO: 320) may be used to assess a cancer patient's (e.g, a patient having cancer that is resistant to one or more cancer therapies other than irofulven) responsiveness to irofulven. The expression level of the biomarker ITGB7 (SEQ ID NO: 320) may be assessed using nucleic acid amplification methods (e.g., PCR) or a device (e.g., a microarray). As is described above, the expression level of ITGB7 (SEQ ID NO: 320) in the patient sample may then be compared, e.g., to the expression level of ITGB7 (SEQ ID NO: 320) in a cell (e.g., a cancer cell) or tissue (e.g., a tumor tissue) known to be sensitive or resistant to treatment with irofulven and used to determine the cancer patient's responsiveness to irofulven. The biomarker ITGB7 (SEQ ID NO: 320) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), and/or GTSF1 (SEQ ID NO: 321). The expression level of the biomarker(s) may be determined using, e.g., a microarray, PCR, or other techniques described herein, for example, using a nucleic acid probe sequence based on the target sequences shown in Tables 1-4.

The biomarker GTSF1 (SEQ ID NO: 321) may be used to assess a cancer patient's (e.g, a patient having cancer that is resistant to one or more cancer therapies other than irofulven) responsiveness to irofulven. The expression level of the biomarker GTSF1 (SEQ ID NO: 321) may be assessed using nucleic acid amplification methods (e.g., PCR) or a device (e.g., a microarray). As is described above, the expression level of GTSF1 (SEQ ID NO: 321) in the patient sample may then be compared, e.g., to the expression level of GTSF1 (SEQ ID NO: 321) in a cell (e.g., a cancer cell) or tissue (e.g., a tumor tissue) known to be sensitive or resistant to treatment with irofulven and used to determine the cancer patient's responsiveness to irofulven. The biomarker GTSF1 (SEQ ID NO: 321) may be used alone to predict cancer patient responsiveness to treatment with irofulven or in combination with one or more additional biomarkers (e.g., one, two, three, four, five, ten, or all of the biomarkers shown in Tables 1-4), such as ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), GJA1 (SEQ ID NO: 218), IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO:

308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), and/or ITGB7 (SEQ ID NO: 320). The expression level of the biomarker(s) may be determined using, e.g., a microarray, PCR, or other techniques described herein, for example, using a nucleic acid probe sequence based on the target sequences shown in Tables 1-4.

Methods of Treatment

The diagnostic methods of the invention permit the assessment of whether a patient is likely to be responsive to treatment with irofulven, and can thus be used to direct the patient's treatment (e.g., as a first line therapy and/or as a second or third line therapy). A patient to be treated or tested for responsiveness to irofulven according to the methods may include, e.g., a patient that has been diagnosed with cancer, a patient that has not received a cancer treatment (e.g., irofulven, an anti-cancer agent other than irofulven, or radiation), a patient that has received a cancer treatment (e.g., an anti-cancer agent other than irofulven or radiation), or a patient during treatment with irofulven.

For example, the patient may have a solid tumor or a hematological cancer, such as a cancer type selected from prostate cancer, ovarian cancer (e.g., ovarian adenocarcinoma or embryonal carcinoma), liver cancer (e.g., hepatocellular carcinoma (HCC) or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. In particular, the cancer of the patient is, e.g., prostate cancer, ovarian cancer, hepatocellular carcinoma (HCC), multiple myeloma, breast cancer, acute myelogenous leukemia (AML), acute lymphoblastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), Hodgkin's lymphoma, cervical cancer, renal cell carcinoma (RCC), esophageal cancer, melanoma, glioma, pancreatic cancer, gastrointestinal stromal tumors (GIST), sarcoma, estrogen receptor-positive (ERpos) breast cancer, non-small cell lung carcinoma (NSCLC), colon cancer, bladder cancer, or squamous cell carcinoma of the head and neck (SCCHN).

The patient may have a cancer (e.g., prostate cancer, ovarian cancer, or hepatocellular carcinoma (HCC)) that is resistant to one or more cancer therapies other than irofulven (e.g., docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, cisplatin, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab), surgery, or radiation. The patient may also have experienced a recurrence following a treatment with a cancer therapy other than irofulven, surgery, or radiation.

A patient found to be responsive to irofulven according to the methods of the invention may be preferentially selected for treatment with irofulven. For example, a patient can be identified as responsive to irofulven by determining the expression level of one or more biomarkers (e.g., one or more of the biomarkers shown in Tables 1-4, such as ATP1B1 (SEQ ID NO: 201)) in a biological sample (e.g., a tumor sample) obtained from the patient, and subsequently administered irofulven. Alternatively, a patient can be identified as less likely to be responsive to irofulven by determining the expression level of one or more biomarkers (e.g., one or more of the biomarkers shown in Tables 1-4, such as ATP1B1 (SEQ ID NO: 201)) in a biological sample obtained from the patient. If the patient exhibits expression levels of one or more biomarkers indicative of non-responsiveness to irofulven, the patient may be treated with or offered a treatment with an agent other than irofulven. In particular, the patient may be treated with, e.g., radiation and/or administration of a therapeutic agent, such as docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, cisplatin, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, or rituximab.

Administration of Irofulven

Once a patient has been determined to be responsive to irofulven, according to the methods described herein, irofulven may be administered to the patient, for example, parenterally, enterally, or topically. Enteral routes of irofulven administration include oral, buccal, sublabial, sublingual, or by inhalation. Parenteral routes of irofulven administration include intravenous, transdermal, intradermal, intramuscular, intra-arterial, intracranial, subcutaneous, intraorbital, intraventricular, intraspinal, intraperitoneal, or intranasal. The preferred route for administration of irofulven may be intravenous, such as intravenous infusion.

Irofulven can be administered at, e.g., a dose of about 0.05 mg/kg to 5 mg/kg, about 0.06 mg/kg to 4 mg/kg, about 0.1 mg/kg to 3 mg/kg, about 0.2 mg/kg to 2 mg/kg, about 0.3 mg/kg to 1 mg/kg, about 0.4 mg/kg to 1 mg/kg, about 0.2 mg/kg to 4 mg/kg, about 0.35 mg/kg to 4.5 mg/kg, about 0.25 mg/kg to 3.5 mg/kg, about 0.15 mg/kg to 2.5 mg/kg, about 0.45 mg/kg to about 1 mg/kg, about 0.45 mg/kg to about 2 mg/kg, or about 0.45 mg/kg to about 4 mg/kg. Irofulven may be administered at a frequency of, e.g., at least once hourly, once daily, twice daily, once weekly, once every two weeks, once every three weeks, once every four weeks, once monthly, once every two months, once every three months, once every six months, or once every year.

For example, irofulven may be administered at a treatment regimen of, e.g., about 0.05 mg/kg to 5 mg/kg, about 0.06 mg/kg to 4 mg/kg, about 0.1 mg/kg to 3 mg/kg, about 0.2 mg/kg to 2 mg/kg, about 0.3 mg/kg to 1 mg/kg, about 0.4 mg/kg to 1 mg/kg, about 0.2 mg/kg to 4 mg/kg, about 0.35 mg/kg to 4.5 mg/kg, about 0.25 mg/kg to 3.5 mg/kg, about 0.15 mg/kg to 2.5 mg/kg, about 0.45 mg/kg to about 1 mg/kg, about 0.45 mg/kg to about 2 mg/kg, or about 0.45 mg/kg to about 4 mg/kg on day 1 and day 8 every 3 weeks. In particular, irofulven may be administered at a treatment regimen of about 0.45 mg/kg on day 1 and day 8 every 3 weeks. The treatment regimen may be repeated one to five times, one to ten times, one to fifteen times, one to twenty times, or more. The administration of irofulven can be repeated at such a frequency for a certain period of time, followed by a period without treatment. Such repeated administrations can occur over a course of therapy lasting a specified length of time (e.g., at least 1 week, 2 weeks, 3 weeks, 1 month, 2 months, 3 months, 6 months, 8 months, 10 months, 12 months, 18 months, 24 months, 36 months, 48 months, or 60 months).

Irofulven can be administered in a pharmaceutical composition that includes one or more pharmaceutically acceptable carriers, excipients, or diluents. Examples of suitable carriers, excipients, or diluents of irofulven include, e.g., saline, sterile water, polyalkylene glycols, oils of vegetable origin, hydrogenated napthalenes, suitable buffer, 1,3-butanediol, Ringer's solution and/or sodium chloride solution. Exemplary formulations for parenteral administration can include solutions prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Other exemplary carriers, excipients, or diluents are described in the Handbook of Pharmaceutical Excipients, 6th Edition, Rowe et al., Eds., Pharmaceutical Press (2009), hereby incorporated by reference in its entirety.

Kits

Kits of the invention can be used for determining the responsiveness of a cancer patient (e.g., a patient having a solid tumor cancer, such as prostate cancer, ovarian cancer, or hepatocellular carcinoma (HCC), or a hematological cancer, such as lymphoma (e.g., cutaneous T-cell lymphoma (CTCL)) to irofulven. Kits of the invention can include reagents and/or materials for, e.g., collecting and/or purifying nucleic acids from biological samples (such as those obtained from a patient to be treated with a target drug(s) of the invention), reagents for amplifying such nucleic acids to produce an amplified sample, and/or at least one device of the invention. Reagents for amplifying nucleic acids may include, e.g., PCR reagents, including but not limited to DNA polymerase, RNA polymerase, PCR buffer, magnesium chloride solutions, nucleic acid primers (e.g., primers designed to target particular biomarkers of responsiveness to a target drug(s) of interest), and/or any other PCR reagents as are well known in the art. In particular, kits useful in the method may include includes one or more of the following: a kit for RNA extraction from tumors (e.g., Trizol for mRNA, mirVana miRNA isolation kit from Ambion Inc), a kit for RNA labeling (e.g., MessageAmp from Ambion Inc., FlashTag from Genisphere Inc), a microarray for measuring biomarker expression (e.g., HG-U133A, HG-U133_Plus2 or miRNA-1.0 from Affymetrix Inc), a microarray hybridization station and scanner (e.g., GeneChip System 3000Dx from Affymetrix Inc), and/or software for analyzing the expression of biomarker genes or RNAs (e.g., miRNAs) as described in herein (e.g., implemented in R from R-Project or S-Plus from Insightful Corp.).

For example, a kit of the invention can include one or more probes capable of detecting one or more biomarkers of Tables 1-4 (e.g., the kit may include probes for the biomarkers of Tables 1-4). Such probes can, for example, include nucleic acids capable of hybridizing to the biomarker based on nucleic acid sequence complementarity. In particular, a probe has at least 85% sequence identity (e.g., 85%, 90%, 95%, 97%, 98%, 99%, or 100% sequence identity) to a nucleic acid sequence that is complementary or identical to at least 5 (e.g., at least 15) consecutive nucleotides of one or more biomarkers. The probes can be attached a solid surface, such as a microarray. The kit may include NanoString capture probes, NanoString reporter probes, and/or one or more nCounter cartridges. The kit may include reagents for next generation sequencing, including but not limited to poly(T) oligonucleotides, dye terminators, sequencing adapters, adapter ligation reagents, reverse transcriptase, primers (e.g., random primers), DNA-cleaving enzymes, polymerases, and/or any combination thereof. The kit may also be one that includes a protein array and/or reagents for detection of the polypeptide product(s) of one or more biomarkers of Tables 1-4.

The following examples are intended to illustrate, rather than limit, the invention.

EXAMPLES

Example 1

Identification of Biomarkers of Sensitivity and Resistance to Irofulven Using Affymetrix HG-U133A Arrays DNA chip measurements of the 60 cancer cell lines of the NCI60 data set were performed using Affymetrix HG-U133A arrays and logit normalized. For each array, the logit transformation was performed followed by a Z-transformation to mean zero and SD 1, and correlated to growth inhibition (log(GI50)). Growth inhibition data of irofulven against the same cell lines were downloaded from the National Cancer Institute. Each gene's expression in each cell line was correlated to the growth of those cell lines (log(GI50)) in the presence of irofulven. The Pearson correlation coefficient was then determined to identify genes positively and negatively correlated to sensitivity to irofulven. Tables 1 and 2 show the top positively correlated genes (the biomarkers of sensitivity) and negatively correlated genes (the biomarkers of resistance) using the Affymetrix HG-U133A arrays.

TABLE 1

Biomarkers of sensitivity to irofulven. Dashes indicate that the Affymetrix probeset has not been mapped to a specific gene. Affymetrix IDs refer to the array type HG-U133A.

| Gene | Affymetrix ID | Correlation | Affymetrix Probe Sequence | Affymetrix Probe SEQ ID NO: |
|---|---|---|---|---|
| S100A10 | 200872_at | 0.571 | AGAGTTGTCCAAAGGGTCGCTTAAG | 1 |
| ATP1B1 | 201242_s_at | 0.554 | TGATCACAAGCACAAATCTTTCCCA | 2 |
| CTBP2 | 201220_x_at | 0.549 | ACACCCTGCTCTACAATGTTGCATC | 3 |
| ASPH | 209135_at | 0.539 | AAAGCTGTGCTGTCGGTGATACAGA | 4 |
| LAPTM4B | 214039_s_at | 0.525 | GTTACAAAGTCAGCAACTCTCCTGT | 5 |
| CTBP2 | 210835_s_at | 0.524 | TGCACGCATAGGATTGAAGACAGTA | 6 |
| MYOF | 201798_s_at | 0.519 | CCAGTAGCAGGTTACGCCATGTCAC | 7 |
| TJP1 | 202011_at | 0.518 | AATACACCACTACATTCTGTTAATC | 8 |
| ASPH | 210896_s_at | 0.517 | GTAACGCCTTGAGCTGGGTTGATTG | 9 |
| LPP | 202822_at | 0.511 | GTTTGGTGCACTCTCGTGGGAGACA | 10 |
| PFN2 | 204992_s_at | 0.503 | CCCCAGGGACATTCCATCATTGCAA | 11 |
| ACTN1 | 208636_at | 0.499 | CAAGCACAAAGTTATATTCCATCCT | 12 |
| CKAP4 | 200999_s_at | 0.474 | TGTGTAATTGTTTGCTGTATCTCCC | 13 |
| MYOF | 211864_s_at | 0.46 | TACCAAATCGACCAGAAACCTCCTT | 14 |
| PPIC | 204517_at | 0.455 | CACCTGCTTAGGGACTTTGAACTTA | 15 |
| MET | 203510_at | 0.454 | AAACTTGTCCTTAGATTAATGTGTC | 16 |
| CEBPD | 203973_s_at | 0.454 | AAGCGGCGCAACCAGGAGATGCAGC | 17 |
| PAPSS2 | 203060_s_at | 0.452 | GATTTCAAGCTGTTCTGAGACATCT | 18 |
| UGDH | 203343_at | 0.448 | TTAATTTCCAGTCACCCCAAATATG | 19 |
| FKBP9 | 212169_at | 0.448 | AACAAGGTGACATTTTTCTGCTGCC | 20 |
| NQO1 | 210519_s_at | 0.446 | GTGGCTTCCAAGTCTTAGAACCTCA | 21 |
| EGFR | 201983_s_at | 0.443 | AAAATCCAGACTCTTTCGATACCCA | 22 |
| LAPTM4B | 208767_s_at | 0.44 | AACTTCCCCCAAATCTGATGGACCT | 23 |
| RBPMS | 209488_s_at | 0.44 | AATTCCGCAAACACTACGACTAGAG | 24 |
| ANXA2 | 210427_x_at | 0.439 | CGTGGCCATCCCTGTGAGGGTGACG | 25 |
| NQO1 | 201468_s_at | 0.435 | TTCATCTTCACTGCAATTTTGTGTA | 26 |
| LAPTM4B | 208029_s_at | 0.433 | ACATGGGGTGACATGCCTCGTATGT | 27 |

TABLE 1-continued

Biomarkers of sensitivity to irofulven. Dashes indicate that the Affymetrix probeset has not been mapped to a specific gene. Affymetrix IDs refer to the array type HG-U133A.

| Gene | Affymetrix ID | Correlation | Affymetrix Probe Sequence | Affymetrix Probe SEQ ID NO: |
|---|---|---|---|---|
| ANXA2 | 213503_x_at | 0.433 | CTCACCATGCTTCCAGCTAACAGGT | 28 |
| ANXA2 | 201590_x_at | 0.43 | GAGGGTGACGTTAGCATTACCCCCA | 29 |
| SEPT10 | 212698_s_at | 0.43 | TGATGACTTCATGCTTTATTATGCC | 30 |
| ALCAM | 201952_at | 0.425 | ACAGCTGTCAGAACCTCGAGAGCAG | 31 |
| NQO1 | 201467_s_at | 0.423 | TCTCTGCAAGGGATCCACGGGACA | 32 |
| SKAP2 | 204362_at | 0.422 | GCAAATGGCAGTGTGCTGTCACCTG | 33 |
| CAPN2 | 208683_at | 0.422 | GACACGAGGCCCTTGGCAGGGAATA | 34 |
| RCN1 | 201063_at | 0.42 | ACAATGCATTTCCTCAGTGATCACT | 35 |
| TXNRD1 | 201266_at | 0.418 | ACACGTGCTTGTGGACATCAGCCTC | 36 |
| ACTN1 | 208637_x_at | 0.418 | GGCGCTGTACGGCGAGAGTGACCTC | 37 |
| CALM1 CALM2 CALM3 | 209563_x_at | 0.416 | TGGCCAGTTTTTCATGCATGCAGCT | 38 |
| LAMB1 | 201505_at | 0.412 | AAGAGTCAGCTGATGCCAGAAGGAA | 39 |
| CTSL1 | 202087_s_at | 0.411 | GAAACCATTGTGGAATTGCCTCAGC | 40 |
| TGIF1 | 203313_s_at | 0.41 | ACTTACAGCTTAACCCATTTTCAAG | 41 |
| ANXA2P2 | 208816_x_at | 0.41 | AAGCCCTTGTATTTTGCTGATCAGC | 42 |
| CALM1 CALM2 CALM3 | 200653_s_at | 0.408 | GAAGAAATCCGTGAGGCATTCCGAG | 43 |
| CD24 | 209771_x_at | 0.403 | GAACACTCTTGCTTTATTCCAGAAT | 44 |
| CALM1 CALM2 CALM3 | 211984_at | 0.403 | AATTTGGTCAAGTCTACTCTTCCGT | 45 |
| PLXNB2 | 208890_s_at | 0.397 | AGAAAAAGCGGTACGATGCCTTCCT | 46 |
| SDC4 | 202071_at | 0.396 | CAGTAACCACATGCGGCTGTTTAAA | 47 |
| ACTN4 | 200601_at | 0.394 | TAACCAAGGAGGGGCCAGTGGATTC | 48 |
| TNFRSF12A | 218368_s_at | 0.389 | AACACTAGGGGCTGGCCCACTAGGA | 49 |
| LOC100652886 LOC100653157 TGFBI | 201506_at | 0.386 | CTTTTATGGGGCCCTGTCCAGGTAG | 50 |
| SQSTM1 | 201471_s_at | 0.385 | CTGCCTTCTTCCAGGATCAGGGGTT | 51 |
| CD24 | 216379_x_at | 0.384 | AATAGACACTCCCCGAAGTCTTTTG | 52 |
| ALDH7A1 | 208951_at | 0.381 | ACACAGAGACTTTTGCTCCGATTCT | 53 |
| LIF | 205266_at | 0.379 | GTAGCATTTCCCTGCAGATGGTACA | 54 |
| AMOTL2 | 203002_at | 0.377 | TTTTTAGTTCTCCTTGATTCTTTGT | 55 |
| MYO1B | 212364_at | 0.377 | ATGACCAGGTTAAATCCCTCTACAT | 56 |
| CDC42BPA | 214464_at | 0.377 | AGCTCTGCAGTATTCAACTGTTGAT | 57 |
| CCND1 | 208712_at | 0.374 | AACCAAAAGAATTTGCACCCCGCTG | 58 |
| AGRN | 212285_s_at | 0.374 | GAGCTCACTGTGGGATGGGGTTGAC | 59 |

TABLE 1-continued

Biomarkers of sensitivity to irofulven. Dashes indicate that the Affymetrix probeset has not been mapped to a specific gene. Affymetrix IDs refer to the array type HG-U133A.

| Gene | Affymetrix ID | Correlation | Affymetrix Probe Sequence | Affymetrix Probe SEQ ID NO: |
|---|---|---|---|---|
| CD24 | 266_s_at | 0.373 | GTAATCTAATATGGCCACAGTAGTC | 60 |
| CD24 | 208651_x_at | 0.372 | AATAGCCACATTTAGAACACTTTTT | 61 |
| CD24 | 208650_s_at | 0.371 | AATCTGCTGGAGTTTCATGTACAAG | 62 |
| RBPMS | 209487_at | 0.37 | AATTAGATTTGTCTCTGGGAATGTG | 63 |
| CALM1 CALM2 CALM3 | 200655_s_at | 0.368 | AACCATCAACATTGCTGTTCAAAGA | 64 |
| LGALS3 | 208949_s_at | 0.367 | CACTTTAACCCACGCTTCAATGAGA | 65 |
| CALM1 CALM2 CALM3 | 211985_s_at | 0.367 | TCGGCAACTTACACACATTGAAAAT | 66 |
| PPP1R3C | 204284_at | 0.365 | TGTACACAACTCACATCCTTCATAT | 67 |
| LMNA | 212086_x_at | 0.362 | TTCGGGGACAATCTGGTCACCCGCT | 68 |
| ADAM9 | 202381_at | 0.361 | ATCTGAACTTTCAAAGCTTGCTATT | 69 |
| FZD6 | 203987_at | 0.361 | GAGTGTCCACTATTGATTGTATTAT | 70 |
| TMSB10 | 217733_s_at | 0.361 | GCAGGAGAAGAACACCCTGCCGACC | 71 |
| AMIGO2 | 222108_at | 0.359 | ATATTGGTTCATGTGCTTGTGTATA | 72 |
| PLK2 | 201939_at | 0.358 | AGCTTTTGGCTGCGTAACTGTGAAC | 73 |
| NFIB | 209289_at | 0.357 | TGAACGAATTTATTTTCCCCTCAGT | 74 |
| ULK2 | 204062_s_at | 0.355 | ACAGTTCACCAAATAGCTAGTCATG | 75 |
| AVPI1 | 218631_at | 0.354 | CATTTCACCACTCATGCTACTAATC | 76 |
| CYR61 | 201289_at | 0.353 | GTGGAGTTGATGACTTTCTGTTTTC | 77 |
| EXT1 | 201995_at | 0.353 | GGCCAATGAGAACTCAACTCCTGGC | 78 |
| TM4SF1 | 209386_at | 0.353 | AAAGCCTTTTGTCCTCCAAAGATGA | 79 |
| COTL1 | 221059_s_at | 0.351 | TGCAAGCTGCGAGGATGGCTTGGGC | 80 |
| PRSS23 | 202458_at | 0.35 | GAGGGGTGACACAGTGTTCCCTCCT | 81 |
| YES1 | 202933_s_at | 0.348 | AGCTTTTCGTCTTCAGTGTCTTAAT | 82 |
| G6PD | 202275_at | 0.347 | CCAGAGCTTATTGGCCACTGGGTCT | 83 |
| BASP1 | 202391_at | 0.347 | CATTCTTCCTCTCCAGATATTTTTG | 84 |
| ZFP36L1 | 211962_s_at | 0.347 | ATGGTTTTGCTCTAGAATACCGTA | 85 |
| FAIM | 220643_s_at | 0.345 | GGACCAAAGTCACTAATGTTTTACA | 86 |
| FLNB | 208614_s_at | 0.344 | TCAGCCTGGGCAGTCTTACCAAAAT | 87 |
| CAV2 | 203323_at | 0.343 | CCTAGGCCATTGCAGCATCCTTAGA | 88 |
| ABCC3 | 208161_s_at | 0.343 | CACCCCTAGGAACTCAGTCCTGTAC | 89 |
| MIR21 VMP1 | 220990_s_at | 0.342 | TAAGGTAAGGTATCCACCCTCGATG | 90 |
| FTH1 | 214211_at | 0.341 | TAGAACTAAGGGTTCCCGACTCTGA | 91 |
| PLOD2 | 202620_s_at | 0.34 | TCCATTTTATTCTTCTGAGTGTCTA | 92 |
| MXRA7 | 212509_s_at | 0.34 | CAGCATCAACCCCTATGGCATGCAT | 93 |

TABLE 1-continued

Biomarkers of sensitivity to irofulven. Dashes indicate that the Affymetrix probeset has not been mapped to a specific gene. Affymetrix IDs refer to the array type HG-U133A.

| Gene | Affymetrix ID | Correlation | Affymetrix Probe Sequence | Affymetrix Probe SEQ ID NO: |
|---|---|---|---|---|
| ANXA4 | 201301_s_at | 0.339 | AAAGTACTGCTTGTTCTCTGTGGAG | 94 |
| PYGL | 202990_at | 0.339 | AGAGAACCTGTTCATCTTTGGCATG | 95 |
| OLFML2A | 213075_at | 0.338 | CCAATTGTGCTGAGTCTCCTACTAG | 96 |
| CYP1B1 | 202437_s_at | 0.336 | TAGCCTTTACTGTTTGATATACCAA | 97 |
| CAMSAP2 | 212765_at | 0.335 | GAGCATTGCTTACAGGTTTTTGTT | 98 |
| GOLM1 | 217771_at | 0.335 | TGGGGCCTAGAAGTTACAGAGCATC | 99 |
| IER3 | 201631_s_at | 0.334 | GAGACTTCGGCGGACCATTAGGAAT | 100 |

TABLE 2

Biomarkers of resistance to irofulven. Dashes indicate that the Affymetrix probeset has not been mapped to a specific gene. Affymetrix IDs refer to the array type HG-U133A.

| Gene | Affymetrix ID | Correlation | Affymetrix Probe Sequence | Affymetrix Probe SEQ ID NO: |
|---|---|---|---|---|
| IGJ | 212592_at | -0.609 | GCTCACCTGAAAGAGGTATGCTCTC | 101 |
| MZB1 | 221286_s_at | -0.608 | AAAGAAGCTGGGGCTTGCTCTGACG | 102 |
| CD8B | 207979_s_at | -0.59 | GTAACATTGGGTCCTGGGTCTTTCA | 103 |
| ITGB7 | 205718_at | -0.588 | GAGGATGACGCCAGAGGCACGGTCG | 104 |
| CD28 | 206545_at | -0.582 | GATCAAACTCAGCAGTACTTGGGTG | 105 |
| CD53 | 203416_at | -0.573 | AAAGGGCAAGATCTCATTTCAATTT | 106 |
| IQGAP2 | 203474_at | -0.567 | ACTGTGATATAGGTACTCTGATTTA | 107 |
| HCLS1 | 202957_at | -0.554 | GTACGTCTAGATTGTGTGGTTTGCC | 108 |
| CD37 | 204192_at | -0.536 | CAACGACTCCACAATCCTAGATAAG | 109 |
| ICAM3 | 204949_at | -0.527 | GTACCCCGAGCTGCGGTGTTTGAAG | 110 |
| PIM2 | 204269_at | -0.526 | ACCGGACACCACCAGACAATAGGAT | 111 |
| ICAM2 | 213620_s_at | -0.516 | CTTGGGACATTGCCTTTTCTAGCCC | 112 |
| ICAM2 | 204683_at | -0.512 | CAAACACTCAGCCCCGAAGATGTTG | 113 |
| GLYR1 SEPT6 | 212414_s_at | -0.509 | ATGTGGCTGTTAATATGTGCTTGTT | 114 |
| CORO1A | 209083_at | -0.504 | GATCGCCAGGTTCTACAAGCTGCAC | 115 |
| SLC43A3 | 213113_s_at | -0.498 | CTTTAGGCCTGTTTGGCTCCGAAGC | 116 |
| NFATC3 | 210555_s_at | -0.497 | TTGTGTGATCCAGCGTCATTTCCAC | 117 |
| SSBP2 | 203787_at | -0.493 | GTATATGTCTGCAATCATGGATAGG | 118 |
| PTPN7 | 204852_s_at | -0.492 | GGGTACAAGCTCCAGAACAGTAACC | 119 |
| NCKAP1L | 209734_at | -0.486 | GTGGAAGCTGTGGTCACTTTCGCAG | 120 |
| RHOH | 204951_at | -0.474 | GAGGCTTGGCCACTGGATGTTTTCA | 121 |
| MYB | 204798_at | -0.465 | TGTGGTTGATAGCCAGTCACTGCCT | 122 |

TABLE 2-continued

Biomarkers of resistance to irofulven. Dashes indicate that the Affymetrix probeset has not been mapped to a specific gene. Affymetrix IDs refer to the array type HG-U133A.

| Gene | Affymetrix ID | Correlation | Affymetrix Probe Sequence | Affymetrix Probe SEQ ID NO: |
|---|---|---|---|---|
| LCP1 | 208885_at | −0.462 | TTTGGAGGCAATCCTACCTTGCTTT | 123 |
| ARHGAP15 | 218870_at | −0.458 | ACCTCATGTCCACGCAAAGCTTGGG | 124 |
| LRMP | 204674_at | −0.454 | AGTGGGATGTCTCTTCAGTTTATGA | 125 |
| FARSA | 216602_s_at | −0.453 | TGGTGGGCCACAAGGTGAACCTGCA | 126 |
| SEPT6 | 212415_at | −0.452 | TAACCACCGATCAGCACAGCTGTCC | 127 |
| LAPTM5 | 201721_s_at | −0.448 | CATAGGCGAATCTGTTCTGCCCGAG | 128 |
| EVI2B | 211742_s_at | −0.447 | ACATATACTTATTACCCAGTACAGT | 129 |
| USP7 | 201498_at | −0.439 | GAACATGTACAATTTGCCACTGGGA | 130 |
| CCND2 | 200953_s_at | −0.436 | ATGTTGTATTGGCTATGATGGTGAC | 131 |
| SEPT6 | 213666_at | −0.435 | AAAGGTGTGACCAGTCATTGCCCCT | 132 |
| RNASE6 | 213566_at | −0.433 | ATTTCTAACCCTGCAACTTTTGCCA | 133 |
| MYC | 202431_s_at | −0.432 | AAAAGCCACAGCATACATCCTGTCC | 134 |
| CYTIP | 209606_at | −0.431 | AAATCTTAGGTTTGCTTATGCCCAG | 135 |
| HBA1 HBA2 | 209458_x_at | −0.429 | AGAGAACCCACCATGGTGCTGTCTC | 136 |
| EVI2A | 204774_at | −0.428 | AATTTAATGGTATCTTCCTTGCTGG | 137 |
| NARF | 219862_s_at | −0.428 | CGGAGAGGTGGTGTTACGCTTTGCT | 138 |
| LAPTM5 | 201720_s_at | −0.426 | AGCTGCTCACAACTGGGTCAACGCT | 139 |
| MFNG | 204153_s_at | −0.426 | GGTCCCAGCCAATTGTGATGATCCT | 140 |
| ARHGDIB | 201288_at | −0.424 | GTCACTCAACGTGGTCCCTAGAACA | 141 |
| ZFP36L2 | 201369_s_at | −0.422 | GACGACTGAGGCAAGAGGGCGCCAG | 142 |
| MAGEA9 MAGEA9B | 210437_at | −0.42 | GGTTCCTTGTCTATTGGGTGATTTG | 143 |
| NASP | 201970_s_at | −0.417 | GTGACTGATATTTCCCACCTTGTCA | 144 |
| SMARCC1 | 201074_at | −0.414 | GAAGAAGGCCTAATCTCTCTCTTTT | 145 |
| ARHGAP6 | 206167_s_at | −0.413 | AAGTGCATAACTATTTTTGACCAGC | 146 |
| PTP4A3 | 206574_s_at | −0.413 | TGGCATCACCGTTGTGGACTGGCCG | 147 |
| SAMSN1 | 220330_s_at | −0.411 | TGGACACATTTTATCCTGATCCACA | 148 |
| HBA1 HBA2 | 211745_x_at | −0.409 | TGGCGAGTATGGTGCGGAGGCCCTG | 149 |
| CXCR4 | 211919_s_at | −0.409 | GTGGTCTATGTTGGCGTCTGGATCC | 150 |
| FEN1 | 204767_s_at | −0.408 | TGGACCTAGACTGTGCTTTTCTGTC | 151 |
| HBA1 HBA2 | 204018_x_at | −0.405 | CTGACCTCCAAATACCGTTAAGCTG | 152 |
| HBA1 HBA2 | 211699_x_at | −0.402 | CGCACAAGCTTCGGGTGGACCCGGT | 153 |
| SLC19A1 | 211576_s_at | −0.401 | GATGTGATGTGAATACTCTTCCCAC | 154 |
| ARHGEF3 | 218501_at | −0.399 | TCATGTGCATTCAAGCTGTGTGACA | 155 |

TABLE 2-continued

Biomarkers of resistance to irofulven. Dashes indicate that the Affymetrix probeset has not been mapped to a specific gene. Affymetrix IDs refer to the array type HG-U133A.

| Gene | Affymetrix ID | Correlation | Affymetrix Probe Sequence | Affymetrix Probe SEQ ID NO: |
|---|---|---|---|---|
| CXCR4 | 209201_x_at | -0.398 | AGCACATCATGGTTGGCCTTATCCT | 156 |
| UTP3 | 209486_at | -0.397 | GAAATTCGTCATCTGTTGACACTTA | 157 |
| PDSS1 | 220865_s_at | -0.396 | GCAGCTATCTTACCAGACTGTGCCT | 158 |
| MAZ | 207824_s_at | -0.395 | AAATGTGAGGCAGCTTTCGCCACGA | 159 |
| SELPLG | 209879_at | -0.395 | CACTGCACTGCCATTGTCTTTTGGT | 160 |
| FARSA | 202159_at | -0.394 | TCCTGTGTGGTGTGTCTACTGTGAG | 161 |
| LCP2 | 205269_at | -0.394 | TGTTTTTTACAGCCAAACCTCTGTC | 162 |
| STAT5A | 203010_at | -0.393 | CCTCCCTCTGAGGCGTGAGGACTCG | 163 |
| CISH | 221223_x_at | -0.392 | AAAGCCCATCCTGAGACATCTTGCT | 164 |
| MAN1A1 | 221760_at | -0.391 | GGTTTTCATATGAGCTACACATTGT | 165 |
| HBA1 HBA2 | 217414_x_at | -0.388 | TCAAGGCCGCCTGGGGTAAGGTCGG | 166 |
| TCF4 | 222146_s_at | -0.388 | AACAGCTGTATTATCTTAAACCCAC | 167 |
| LAIR1 | 210644_s_at | -0.385 | CAGTTCCCTGGCTGTTTCTAGAGAC | 168 |
| MYLIP | 220319_s_at | -0.382 | AGCTACGCAAGCTGAAGGAAGCCAT | 169 |
| IKZF1 | 205039_s_at | -0.38 | CGCCCATCCGTGCTATGACATGGAG | 170 |
| CXCR4 | 217028_at | -0.379 | GTATGTCTCGTGGTAGGACTGTAGA | 171 |
| TAPBPL | 218747_s_at | -0.377 | GAACAGCCTTGGGAGTCATCTTTGC | 172 |
| ZFP36L2 | 201368_at | -0.376 | GTGAAGCAACCGCCTTAGTGCTGAA | 173 |
| IL2RG | 204116_at | -0.374 | AACCCCAATCCTCTGACAGAAGAAC | 174 |
| TNFAIP8 | 210260_s_at | -0.374 | GTGTCATTGCCTTGAAATGCTTGCT | 175 |
| PRKCB | 209685_s_at | -0.372 | GAAAAGGGCATTTGGCACCACTCTC | 176 |
| PAICS | 201014_s_at | -0.371 | GATGTCTGGGAACACTGCATATCCA | 177 |
| IKZF1 | 205038_at | -0.371 | CCCATATCCCTTCTGTAATTTGTAC | 178 |
| EZH2 | 203358_s_at | -0.368 | CTGCCTTAGCTTCAGGAACCTCGAG | 179 |
| ADCK3 | 218168_s_at | -0.368 | CCCTTCCAATCTCTGTTCAGTGCAA | 180 |
| SRSF2 | 214882_s_at | -0.365 | AGTGCAGAGTGCTTGGCTGTTTCCT | 181 |
| VARS | 201797_s_at | -0.364 | TGAGCTGGCGCTAAGCATCACGCGA | 182 |
| NDUFV1 | 208714_at | -0.364 | GACGGTGCTGATGGACTTCGATGCG | 183 |
| REPIN1 | 219041_s_at | -0.363 | CCTATAATTTCTACCTATTGGGCCT | 184 |
| GMFG | 204220_at | -0.362 | GGCTGGGGACTGAATTCCTGATGTC | 185 |
| MCM7 | 208795_s_at | -0.357 | GTCAAAGGACTCTCTTCTAGGAGAC | 186 |
| TUFM | 201113_at | -0.356 | ATGCCCGGGGAGGACCTGAAGTTCA | 187 |
| HMHA1 | 212873_at | -0.355 | CTCCCTTTTCCAGAACACCAGGTGT | 188 |
| SON | 213538_at | -0.355 | TTGGGTACATAGCCCATTGCCCTTA | 189 |
| TXNIP | 201008_s_at | -0.353 | TACAAGTTCGGCTTTGAGCTTCCTC | 190 |
| NPRL2 | 203246_s_at | -0.353 | GACTCGGGAAGAGCAGAGCCACCCT | 191 |

TABLE 2-continued

Biomarkers of resistance to irofulven. Dashes indicate that the Affymetrix probeset has not been mapped to a specific gene. Affymetrix IDs refer to the array type HG-U133A.

| Gene | Affymetrix ID | Correlation | Affymetrix Probe Sequence | Affymetrix Probe SEQ ID NO: |
|---|---|---|---|---|
| TCF4 | 213891_s_at | -0.353 | GGGAAATTTTTGCGACTGTACACA | 192 |
| NADK | 208918_s_at | -0.352 | ATTTTTCCGCAAATCAGTCGGTTGA | 193 |
| RRP1B | 212846_at | -0.352 | TGTTATCCTTTCTAATTTTTACTGA | 194 |
| MAP4K1 | 214219_x_at | -0.352 | CCAGCAACCTCTACATCCAGGAATG | 195 |
| DDX39A | 201584_s_at | -0.35 | GCAGTTCAAGGATTTCCAGCGGCGG | 196 |
| MAP4K1 | 206296_x_at | -0.35 | GGTCAGCTTCAGGCCTTCTGGAAGC | 197 |
| TXNIP | 201009_s_at | -0.349 | GAAGCAGCTTTACCTACTTGTTTCT | 198 |
| USP20 | 203965_at | -0.348 | GCGTCTTTGTTTCTATCAGTCTTTG | 199 |
| IFI16 | 208965_s_at | -0.347 | GACCTGGCTGAAACTCTTAAAAAAG | 200 |

Example 2

Identification of Biomarkers of Sensitivity and Resistance to Irofulven Using Affymetrix HG-U133_Plus_2 Arrays DNA chip measurements of the 60 cancer cell lines of the NCI60 data set were also performed using HG-U133_Plus_2 arrays and logit normalized. For each array, the logit transformation was performed followed by a Z-transformation to mean zero and SD 1, and correlated to growth inhibition (log(GI50)). Growth inhibition data of irofulven against the same cell lines were downloaded from the National Cancer Institute. Each gene's expression in each cell line was correlated to the growth of those cell lines (log(GI50)) in the presence of irofulven. The Pearson correlation coefficient was then determined to identify genes positively and negatively correlated to sensitivity to irofulven. Tables 3 and 4 show the top positively correlated genes (the biomarkers of sensitivity) and negatively correlated genes (the biomarkers of resistance) using the Affymetrix HG-U133_Plus_2 arrays. The Affymetrix HG-U133_Plus_2 array includes additional genes (e.g., PTGR1 and NME7) that are not included in the Affymetrix HG-U133A array, which were top ranking biomarkers of sensitivity and biomarkers of resistance, as shown in Tables 3 and 4.

TABLE 3

Biomarkers of sensitivity to irofulven. Dashes indicate that the Affymetrix probeset has not been mapped to a specific gene. Affymetrix IDs refer to the array type HG-U133_Plus_2.

| Gene | Affymetrix ID | Correlation | Affymetrix Probe Sequence | Affymetrix Probe SEQ ID NO: |
|---|---|---|---|---|
| ATP1B1 | 201242_s_at | 0.33 | GGACCTACACTTAATCTATATGCTT | 201 |
| UCHL1 | 201387_s_at | 0.3 | AGCCCATGATGCCGTGGCACAGGAA | 202 |
| PTGR1 | 231897_at | 0.3 | AGGATTTGAAAACATGCCAGCTGCA | 203 |
| NME7 | 227556_at | 0.29 | GACACAGCTTTAGAACATACCGGAG | 204 |
| PLS3 | 201215_at | 0.27 | TGTACTCTTGCTTTGTCAAGCTGTT | 205 |
| S100A10 | 200872_at | 0.27 | GGACCTGGACCAGTGTAGAGATGGC | 206 |
| CD24 | 209771_x_at | 0.27 | GAACCTGGTCCTAAGCCTAAAAGTG | 207 |
| NQO1 | 210519_s_at | 0.26 | ATATAGCATTGGGCACACTCCAGCA | 208 |
| CD24 | 216379_x_at | 0.26 | CATGGTCACACACTGATGCTTAGAT | 209 |
| PTGR1 | 228824_s_at | 0.26 | AATGGAGAGGTCCTGCTTGAAGCTT | 210 |
| MYOF | 201798_s_at | 0.26 | CCAGTAGCAGGTTACGCCATGTCAC | 211 |
| LAPTM4B | 214039_s_at | 0.26 | ATATTTGATATACTTCTGCCTAACA | 212 |
| CALD1 | 212077_at | 0.25 | ATCACTGCTGACTTTTATTCCAATA | 213 |

TABLE 3-continued

Biomarkers of sensitivity to irofulven. Dashes indicate that the Affymetrix probeset has not been mapped to a specific gene. Affymetrix IDs refer to the array type HG-U133_Plus_2.

| Gene | Affymetrix ID | Correlation | Affymetrix Probe Sequence | Affymetrix Probe SEQ ID NO: |
|---|---|---|---|---|
| PDGFC | 218718_at | 0.25 | AAGTAGACATTCAGATCCAGCCATT | 214 |
| BASP1 | 202391_at | 0.25 | TGGATCTCAATGCCAATCCTCCATT | 215 |
| NQO1 | 201468_s_at | 0.25 | AATAGTCAATTTCTACTTCTGGAAG | 216 |
| ID1 | 208937_s_at | 0.25 | CACCCTCAACGGCGAGATCAGCGCC | 217 |
| GJA1 | 201667_at | 0.25 | GAGTGGACTATTAAATGTGCCTAAA | 218 |
| ATP1B1 | 201243_s_at | 0.25 | GTTATGCTTGTATTGAATGCTGTCT | 219 |
| CD24 | 208650_s_at | 0.24 | GAGAGGTTTGACTAGATGATGGATG | 220 |
| EGR1 | 227404_s_at | 0.24 | TGAGCATGTCCCTCACAATTGCACA | 221 |
| PERP | 222392_x_at | 0.24 | GTGCCACTAAAACAGCCTCAGGAGA | 222 |
| CYR61 | 201289_at | 0.24 | CTTCATTTTGGAGCTTGTGGAGTTG | 223 |
| AKR1B10 | 206561_s_at | 0.24 | GCAACCATACTCAGCTTCAACAGAA | 224 |
| PFN2 | 204992_s_at | 0.24 | TTGCTTCTATTGTTTGGGCCTTGTG | 225 |
| TFPI2 | 209278_s_at | 0.23 | GCTTTCACCTATACTGGCTGTGGAG | 226 |
| CTBP2 | 201218_at | 0.23 | GAGCCTTTGTATAGGTACATTCCTG | 227 |
| ASPH | 209135_at | 0.23 | AGTAAGTTTTGCTGGATTTTTGTAG | 228 |
| PLK2 | 201939_at | 0.23 | CAGTTCTTGACTTTGGACAATCCCA | 229 |
| FAM213A | 228155_at | 0.22 | CATATGATGTTTGAGTGCTGTTGTT | 230 |
| NQO1 | 201467_s_at | 0.22 | CATTCTCTGGCCAATTCAGAGTGGC | 231 |
| MYOF | 211864_s_at | 0.22 | TACCAAATCGACCAGAAACCTCCTT | 232 |
| TM4SF1 | 209386_at | 0.22 | AAAGCCTTTTGTCCTCCAAAGATGA | 233 |
| ALCAM | 201952_at | 0.22 | GGCAGCCACATGCACGAAGATGCTA | 234 |
| WWTR1 | 202133_at | 0.22 | CCATTTCTTTCACTGATTACACCAT | 235 |
| EDIL3 | 225275_at | 0.22 | ATAACCTTTGCAAACCTTCAAGCTG | 236 |
| COL1A1 | 1556499_s_at | 0.22 | TTTTTATCTTTGACCAACCGAACAT | 237 |
| TJP1 | 202011_at | 0.22 | GATACAATGCTGTGCCCTAAAGTGT | 238 |
| PLOD2 | 202620_s_at | 0.22 | TGTTGACTTGATGTTTTATCACTTC | 239 |
| YAP1 | 224894_at | 0.22 | ACACAGGGAAGTGACTTTGCTACAA | 240 |
| EGFR | 201983_s_at | 0.21 | GTGTCAACAGCACATTCGACAGCCC | 241 |
| MET | 203510_at | 0.21 | GCTGAACTGAATGGTACTTCGTATG | 242 |
| AJUBA | 225806_at | 0.21 | AAAGCTCAATTCCTATTTTGGTGTG | 243 |
| CEBPD | 203973_s_at | 0.21 | AGAAGCTACAGCCTGGACTTACCAC | 244 |
| ASPH | 210896_s_at | 0.21 | CGCTCAGTGCTCTTACTAGATGAAC | 245 |
| AMIGO2 | 222108_at | 0.21 | GAGTAACTTCTTAAATCCCTGTTCT | 246 |
| AKR1C1 | 204151_x_at | 0.21 | ATCTCTCCTGCTTGGTGATTTCAGC | 247 |
| AKR1C2 LOC101930400 | 209699_x_at | 0.21 | CACATCGCCTCTGGTTAAATCTCTC | 248 |

TABLE 3-continued

Biomarkers of sensitivity to irofulven. Dashes indicate that the Affymetrix probeset has not been mapped to a specific gene. Affymetrix IDs refer to the array type HG-U133_Plus_2.

| Gene | Affymetrix ID | Correlation | Affymetrix Probe Sequence | Affymetrix Probe SEQ ID NO: |
|---|---|---|---|---|
| AKR1C3 | 209160_at | 0.21 | CAGTCAACTACAGCTGAGTCCATAG | 249 |
| LAPTM4B | 208767_s_at | 0.21 | TTCACTAACCTTCCCTAGGCATTGA | 250 |
| PRSS23 | 202458_at | 0.21 | AGAATCACTCCTCTCAAATATGCCC | 251 |
| CKAP4 | 200999_s_at | 0.21 | CCATGAAGAGGTTTGCCGTCTGGGC | 252 |
| GPX8 | 227628_at | 0.21 | GAGCACTGTGTATGACTGAAATTTC | 253 |
| LOC101928916 NNMT | 202237_at | 0.21 | CAACAACGAAGGACTTTTCTCCCTG | 254 |
| LAMC1 | 200771_at | 0.21 | TCACTTTAGCTGTTTGCCTTACTCT | 255 |
| TGFBI | 201506_at | 0.21 | AGAAACTTGGATGTCACTGCCTGAC | 256 |
| LAPTM4B | 208029_s_at | 0.2 | AAGACCATTAGAAAGCACCAGGCCG | 257 |
| CD24 | 266_s_at | 0.2 | CTACTGTGTGTGTGAATGAACACTC | 258 |
| PERP | 217744_s_at | 0.2 | TTCTACACATCTGCCTAACTTGGGA | 259 |
| AKR1C2 LOC101930400 | 211653_x_at | 0.2 | CCCCCCTAATTATCCATTTTCTGAT | 260 |
| YAP1 | 224895_at | 0.2 | GTTTTATGTCCTTGTTCCTAATGTA | 261 |
| ABCC3 | 208161_s_at | 0.2 | CACCCCTAGGAACTCAGTCCTGTAC | 262 |
| LIMCH1 | 212328_at | 0.2 | TGGGTTCTTTGCATGTGGGTTCCAT | 263 |
| KRT19 | 201650_at | 0.2 | GCTGAGCATGAAAGCTGCCTTGGAA | 264 |
| CD24 | 208651_x_at | 0.2 | AACACTTTTGTTATCAGTCAATAT | 265 |
| CRIM1 | 228496_s_at | 0.2 | TAAAGTTCAGCAACCTCTGTCCAAG | 266 |
| SEMA3C | 203789_s_at | 0.2 | GTGACTTAATATCTATTCCATTTGT | 267 |
| TRIM16 | 204341_at | 0.2 | ATATGGTGCTGTTCTCTATGTGTTT | 268 |
| TSPAN6 | 209108_at | 0.2 | CTTGGGTCTAAGGCATCCACGACTG | 269 |
| PTPN14 | 226282_at | 0.2 | TCACCATCTCTTATGTTGTTGCCGT | 270 |
| NGFRAP1 | 217963_s_at | 0.2 | CAAGTGGGTCTTGTGTTGCCAGCTT | 271 |
| SLPI | 203021_at | 0.19 | TCTGTCCTCCTAAGAAATCTGCCCA | 272 |
| LGALS3 | 208949_s_at | 0.19 | CACTTTAACCCACGCTTCAATGAGA | 273 |
| CTBP2 | 210554_s_at | 0.19 | GCACCCCAACGAGCAATAGCAGAGA | 274 |
| C19orf33 | 223631_s_at | 0.19 | TTCTCTTACCGCCATGGAGTTCGAC | 275 |
| PLOD2 | 202619_s_at | 0.19 | CTTAATGTCTGCTCTGAGCCTTAAA | 276 |
| PPIC | 204517_at | 0.19 | CCCTTCCTCAAGTGGTGCTATTTTA | 277 |
| ERRFI1 | 224657_at | 0.19 | GGTACATTACTGCAATGTTCTCTTA | 278 |
| CTBP2 | 201220_x_at | 0.19 | GTTTGCCTGTGGTAGACACCTGCAC | 279 |
| NARR RAB34 | 1555630_a_at | 0.19 | AATGCATTGCATCAACCTACTATAG | 280 |
| FAM213A | 224435_at | 0.19 | AAACCACAGACTTTGGCCTCAGAGA | 281 |
| SEPT10 | 212698_s_at | 0.19 | ATAAAGTACCTTTGAGCATGAGTGT | 282 |
| LAPTM4B | 1554679_a_at | 0.19 | GGTCCTTATTATTCTTCTGTTTATT | 283 |

TABLE 3-continued

Biomarkers of sensitivity to irofulven. Dashes indicate that the Affymetrix probeset has not been mapped to a specific gene. Affymetrix IDs refer to the array type HG-U133_Plus_2.

| Gene | Affymetrix ID | Correlation | Affymetrix Probe Sequence | Affymetrix Probe SEQ ID NO: |
|---|---|---|---|---|
| PON2 | 201876_at | 0.19 | GACTACTATGGCTGTTTAGAACTAC | 284 |
| CD24 | 209772_s_at | 0.19 | TGGAACTTCAAGTAACTCCTCCCAG | 285 |
| TPM1 | 210986_s_at | 0.19 | ATTCCTTTCTGATTGGCACACGTGC | 286 |
| RAB13 | 202252_at | 0.19 | ACTAGGGAATTTGCTCCTGTTCTGT | 287 |
| AKR1C1 | 216594_x_at | 0.19 | TGTGGTCCTGGCCAAGAGCTACAAT | 288 |
| PTK2 | 208820_at | 0.19 | AAAGCCATGTTGACTATTTTACAGC | 289 |
| LAMB1 | 201505_at | 0.18 | AAAGCTCAAGAATTAGCAAGACTGG | 290 |
| GPRC5A | 203108_at | 0.18 | TCCCCAAACTTGCTGTCAATTCCGA | 291 |
| PAPSS2 | 203060_s_at | 0.18 | GATTTCAAGCTGTTCTGAGACATCT | 292 |
| LPP | 241879_at | 0.18 | TAAACAGCCACAATCGCATTCAGTC | 293 |
| GNG11 | 204115_at | 0.18 | GGGAGAAACTGCATCCTAAGTGGAA | 294 |
| DDAH1 | 209094_at | 0.18 | TATGGTTATCCACTCTGTGTGCCAA | 295 |
| CYR61 | 210764_s_at | 0.18 | GAAATACCGGCCCAAGTACTGCGGT | 296 |
| GNG12 | 212294_at | 0.18 | GTAATAATGTCTTGTTTTTAGCCAT | 297 |
| TSPAN6 | 209109_s_at | 0.18 | ATTTCCTTTGGAGTTGCTTGCTTCC | 298 |
| LIMCH1 | 212327_at | 0.18 | TCCAAAAGCTAGTCCCTACTCTTTA | 299 |
| SFN | 33323_r_at | 0.18 | CCATGTTTCCTCTCAATAAAGTTCC | 300 |

TABLE 4

Biomarkers of resistance to irofulven. Dashes indicate that the Affymetrix probeset has not been mapped to a specific gene. Affymetrix IDs refer to the array type HG-U133_Plus_2.

| Gene | Affymetrix ID | Correlation | Affymetrix Probe Sequence | Affymetrix Probe SEQ ID NO: |
|---|---|---|---|---|
| IGLC1 | 214677_x_at | -0.31 | AAGTCCCACAGAAGCTACAGCTGCC | 301 |
| IGLC1 | 209138_x_at | -0.29 | AAGACAGTGGCCCCTACAGAATGTT | 302 |
| CYAT1 IGLC1 IGLV1-44 | 215121_x_at | -0.28 | GAGCCGTGACAGTGGCCTGGAAGGC | 303 |
| LAPTM5 | 201721_s_at | -0.26 | AAAACAGTCCCTTCAAACACACAAT | 304 |
| ARHGDIB | 201288_at | -0.25 | GTCTCCATCTCAGTACACAATCATT | 305 |
| IGLV1-44 | 215379_x_at | -0.25 | CTCCTCTGAGGAGCTTCAAGCCAAC | 306 |
| SLC43A3 | 213113_s_at | -0.24 | CGAAGCCTATATGTGCCTGGATCCT | 307 |
| LCP1 | 208885_at | -0.24 | TAAGCATCCTTAGGGTTCTGCCTCT | 308 |
| HCLS1 | 202957_at | -0.22 | CTGTCTACTGCAACTGTGATTTCCC | 309 |
| CD53 | 203416_at | -0.22 | AAAGGGCAAGATCTCATTTCAATTT | 310 |
| ARHGDIB | 1555812_a_at | -0.22 | CTGTGGTGACAGATCCGAAAGCCCC | 311 |

TABLE 4-continued

Biomarkers of resistance to irofulven. Dashes indicate that the Affymetrix probeset has not been mapped to a specific gene. Affymetrix IDs refer to the array type HG-U133_Plus_2.

| Gene | Affymetrix ID | Correlation | Affymetrix Probe Sequence | Affymetrix Probe SEQ ID NO: |
|---|---|---|---|---|
| SLC43A3 | 210692_s_at | -0.21 | TCATCCTGCAAGTGATCAGCCGCTC | 312 |
| MZB1 | 221286_s_at | -0.21 | TAAAACCCAGTGACCTCACTTCTTT | 313 |
| RASSF5 | 223322_at | -0.21 | TGCTGCAACCGCTGTGAATGCTGCT | 314 |
| FAM46C | 226811_at | -0.2 | TGTTCTATATTTGCATAGCCTTTGA | 315 |
| RCSD1 | 225763_at | -0.2 | CAAAAGGCCTTATGTCACCACTGG | 316 |
| IGJ | 212592_at | -0.2 | ATAGGTCAATTATATGTCTCCATTA | 317 |
| IGLC1 IGLJ3 IGLV2-14 IGLV@ | 217148_x_at | -0.19 | TAATCGGCCCTCAGGGGTTTCTAAT | 318 |
| LPXN | 216250_s_at | -0.19 | TTTCACCTCTAGTGATGGCCCTACT | 319 |
| ITGB7 | 205718_at | -0.19 | TGCAAAGAGCGGACCCTGGACAACC | 320 |
| GTSF1 | 227711_at | -0.19 | AACTGACAAGCACACTTTTTTCCTC | 321 |
| IGLL3P | 215946_x_at | -0.19 | GTGGCCCCTGCAGAATGTTCATAGG | 322 |
| ICAM2 | 213620_s_at | -0.19 | TAGTCACGGTGGTGTCGGTGTTGCT | 323 |
| PRSS2 | 205402_x_at | -0.18 | GAGAGCACAACATCGAAGTCCTGGA | 324 |
| MZB1 | 223565_at | -0.18 | TACACGATGTCCTGGACCGGAGCTG | 325 |
| IFITM1 | 214022_s_at | -0.18 | CAACCTTTGCACTCCACTGTGCAAT | 326 |
| IKZF1 | 227346_at | -0.18 | TGCAGTCATATTTCCAGTCTGCCTC | 327 |
| CELF2 | 202157_s_at | -0.18 | GTCACCTTTGCTGAACTCACAGTT | 328 |
| RAC2 | 213603_s_at | -0.18 | GCCAGATGGTTGCTGCCACAACTTG | 329 |
| IFITM1 IFITM2 | 201601_x_at | -0.18 | ACCCTCTTCTTGAACTGGTGCTGTC | 330 |
| PVALB | 205336_at | -0.18 | GATGTCGATGACAGACTTGCTGAAC | 331 |
| CYFIP2 | 215785_s_at | -0.18 | CAGCCTGCCATAGGATCCAACTGGA | 332 |
| CDK6 | 224847_at | -0.18 | GTGTTTCTGTTGCAGTGGCAAAGGT | 333 |
| MYB | 204798_at | -0.18 | AAGCATGCGTTGCACTTCTTTTTTG | 334 |
| TCF4 | 212386_at | -0.18 | GTCTAGTGCTCTTTTGCTATAAAAT | 335 |
| CCND2 | 200953_s_at | -0.17 | TATGTTCATCACCCTTATATCATGT | 336 |
| PPM1K | 235061_at | -0.17 | AAGACTCTTAGGCAGCTATGGGTTT | 337 |
| LAPTM5 | 201_720_s_at | -0.17 | TGTTCAAGTGCGTGTGGCGGTGCTA | 338 |
| CDK6 | 224851_at | -0.17 | GCTTCAGGCAACTTAGCTGTGTACA | 339 |
| IFI16 | 208966_x_at | -0.17 | GACATACTCAATCCTGATTCCAAGT | 340 |
| IFI16 | 206332_s_at | -0.17 | AGAAAGACATACTCAATCCTGATTC | 341 |
| EVI2A | 204774_at | -0.17 | ACACCAGCTTATCAACCAACACAGC | 342 |
| CDK6 | 224848_at | -0.17 | GGGTGCATGTTCCTTAAAGGTGCAT | 343 |
| CORO1A | 209083_at | -0.17 | GCTCCAGAAGCGCTTGGACAGGCTG | 344 |
| LINC00341 SYNE3 | 219563_at | -0.17 | GAGGGACCATATCTACTCTTGTCAT | 345 |

TABLE 4-continued

Biomarkers of resistance to irofulven. Dashes indicate that the Affymetrix probeset has not been mapped to a specific gene. Affymetrix IDs refer to the array type HG-U133_Plus_2.

| Gene | Affymetrix ID | Correlation | Affymetrix Probe Sequence | Affymetrix Probe SEQ ID NO: |
|---|---|---|---|---|
| LOC101928620 POU2AF1 | 205267_at | -0.16 | GCAGGTGTGCTTAGCTCTTGATAGT | 346 |
| CX3CR1 | 205898_at | -0.16 | GAAAATACCCCATCATTCATGCTAC | 347 |
| DOCK2 | 213160_at | -0.16 | GAAGGCAAACAGATCCCAGACTCGC | 348 |
| WIPF1 | 202664_at | -0.16 | GGTAGAGACTACCCTAGACATCTGC | 349 |
| TCF4 | 213891_s_at | -0.16 | AGGTTGTGTGCTGGAGTTCCTTCAA | 350 |
| ST3GAL6 | 210942_s_at | -0.16 | ACAGGAATTATTGCCATCACATTGG | 351 |
| GLYR1 SEPT6 | 212414_s_at | -0.16 | CAGTGTAGATGGCTCTTGTTTTTGT | 352 |
| TRBC1 | 211796_s_at | -0.16 | CAATGACTCCAGATACTGCCTGAGC | 353 |
| AZGP1 | 209309_at | -0.16 | AAAAAATCATCTCACCTTGAGCCCA | 354 |
| LY96 | 206584_at | -0.16 | ATCTCTATATAACTGTCAACACCAT | 355 |
| GIMAP2 | 232024_at | -0.16 | TGTTTTGTTGCTTACTCTTTAGTAT | 356 |
| HERC5 | 219863_at | -0.16 | ACATCATATTCCTTACCTCTTTTGG | 357 |
| IGLL5 | 217235_x_at | -0.15 | GGCTCCAGGCTGAGGATGAGGCTGA | 358 |
| ST3GAL6 | 213355_at | -0.15 | GGCTCTGGAAATCTAAGTTCATACT | 359 |
| ICAM3 | 204949_at | -0.15 | TGGTACTTATCAGTGCCAAGCGTCC | 360 |
| LCP2 | 205269_at | -0.15 | TGTTTTTTACAGCCAAACCTCTGTC | 361 |
| NCKAP1L | 238668_at | -0.15 | GAATAGTTGTCTTTTGAGCCTCAGA | 362 |
| P2RY8 | 229686_at | -0.15 | TTGAGTCCGGGTGTTCAAGGGCCAA | 363 |
| CCR1 | 205098_at | -0.15 | CCAAGGACCCCTTATTTATCATGCC | 364 |
| GMFG | 204220_at | -0.15 | AGCTGAGGAAATTCCGCTTCCGAAA | 365 |
| EVI2B | 211742_s_at | -0.15 | TCCATCCTCAAATGACTCTTTTTTC | 366 |
| — | 229670_at | -0.15 | GTGAAATCAGGGTGCTGTTACCAAA | 367 |
| BCL2 | 203685_at | -0.15 | GATGGAAAGGCTCGCTCAATCAAGA | 368 |
| RAC2 | 207419_s_at | -0.15 | ATCCACAGACGGACGTCTTCCTCAT | 369 |
| IQGAP2 | 203474_at | -0.15 | TACTGCCTCATGTAAAGACTCTTGC | 370 |
| IFI16 | 208965_s_at | -0.15 | ACTTCATTTTCTTAGCGTTTCTGGA | 371 |
| PPM1K | 226773_at | -0.15 | CTGATGTGTCCCCAAACTGATTTAA | 372 |
| LEF1 | 221558_s_at | -0.15 | TGTAACACATAGTGGCTTCTCCGCC | 373 |
| SLC1A4 | 209610_s_at | -0.15 | GCTAACCCAGTATGTTCTTCTTTTT | 374 |
| CD38 | 205692_s_at | -0.15 | CTCCTTGACTCCTTGTGGTTTATGT | 375 |
| ALDH1A2 LOC101928635 | 207016_s_at | -0.15 | TGAGCCCTGACAGATGCCGTATTTC | 376 |
| SSBP2 | 203787_at | -0.15 | ACATTGACCCACAGGACATTGTAAA | 377 |
| PTPRC | 212588_at | -0.15 | GCATTTAGTCCAATGTCTTTTTAAG | 378 |
| ERN1 | 227755_at | -0.15 | AGAAAGCATTACCAGTCACCTACTC | 379 |

TABLE 4-continued

Biomarkers of resistance to irofulven. Dashes indicate that the Affymetrix probeset has not been mapped to a specific gene. Affymetrix IDs refer to the array type HG-U133_Plus_2.

| Gene | Affymetrix ID | Correlation | Affymetrix Probe Sequence | Affymetrix Probe SEQ ID NO: |
|---|---|---|---|---|
| IRF4 | 204562_at | -0.14 | TGTGGGAGTCTTGGGTACTCGCACC | 380 |
| RHOH | 204951_at | -0.14 | CCTCCTGCGTCAATGCCATGGAAGG | 381 |
| FAM26F | 229390_at | -0.14 | ATACGGTGATTCCTGTTCTTGGCTT | 382 |
| IGK IGKC | 224795_x_at | -0.14 | CTCGCCCGTCACAAAGAGCTTCAAC | 383 |
| PTPRC | 207238_s_at | -0.14 | AATGAGGAAACTCCAAACCTCCTGT | 384 |
| TCF4 | 222146_s_at | -0.14 | TATCTTAAACCCACATAAACACTTC | 385 |
| RASSF5 | 1554834_a_at | -0.14 | AGCACATTCCTTTTGCAGGTCTGAG | 386 |
| ARHGAP15 LOC101928361 | 218870_at | -0.14 | ACGTTGTCACCGGAGCACTGAAGAT | 387 |
| — | 236191_at | -0.14 | GGAACACATTAGTCTATGGGACCTT | 388 |
| MAF | 209348_s_at | -0.14 | GTATTTGGGACTGAATTGCACTAAG | 389 |
| CD8B LOC100996919 | 215332_s_at | -0.14 | TGTCCCCCTTGTGGAACCAAATGTA | 390 |
| ATF3 | 202672_s_at | -0.14 | GAATTCTCCCAGCGTTAACACAAAA | 391 |
| CD3D | 213539_at | -0.14 | TGCTCAGTACAGCCACCTTGGAGGA | 392 |
| SLC1A4 | 212811_x_at | -0.14 | GTTTTCATGAACTAGCAACCCCACC | 393 |
| IGK IGKC | 221651_x_at | -0.14 | CTCGCCCGTCACAAAGAGCTTCAAC | 394 |
| IGK IGKC | 221671_x_at | -0.14 | AAATCTGGAACTGCCTCTGTTGTGT | 395 |
| SAMSN1 | 220330_s_at | -0.14 | GTATCTCTAACATTCCAAATTACTG | 396 |
| PIM2 | 204269_at | -0.14 | CCCTAGCCTAGGGTCCCATATTGGG | 397 |
| DOCK8 | 225502_at | -0.14 | GTAATGGTGGACTAATTGCTGTATA | 398 |
| TCF4 | 203753_at | -0.14 | GTGCAACTTGAGGGACGACTTTCTT | 399 |
| PTPN7 | 204852_s_at | -0.14 | TCATCCATCTCAGCATCAACACAAT | 400 |

Example 3

Predicting Responsiveness to Irofulven in Various Cancer Patient Populations

An mRNA-based predictor of responsiveness to irofulven developed according to the methods of the invention was applied to 3,522 patients having a variety of cancers. Each patient had a pre-treatment measurement of gene expression with an Affymetrix array. The predicted irofulven sensitivity of each patient was calculated as the difference between the mean of the expression levels of the biomarkers of sensitivity and the mean of the expression levels of the biomarkers of resistance for the patient. When the patients were grouped by cancer types, and cancer types predicted to be more responsive to irofulven were identified (FIG. 1).

Of 27 different cancer types, solid tumor cancers were predicted to be more responsive to irofulven treatment than hematological cancers. In particular, patients with prostate cancer, ovarian cancer, hepatocellular carcinoma (HCC), breast cancer, cervical cancer, renal cell carcinoma (RCC), esophageal cancer, melanoma, glioma, pancreatic cancer, gastrointestinal stromal tumors (GIST), sarcoma, estrogen receptor-positive (ERpos) breast cancer, non-small cell lung carcinoma (NSCLC), colon cancer, bladder cancer, and squamous cell carcinoma of the head and neck (SCCHN) were predict to be more responsive to irofulven treatment. Patients with hematological cancer types were also predicted to be responsive to irofulven treatment, in particular, cutaneous T-cell lymphoma (CTCL), multiple myeloma, acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), peripheral T-cell lymphoma (PTCL), and Hodgkin's lymphoma patients were predicted to be the most responsive to irofulven.

The median of the boxplots shown in FIG. 1 is a cutoff that may be used to separate patients predicted to be responsive to irofulven treatment from patients predicted to be non-responsive to irofulven treatment for a given cancer type. Values above the median indicate patients predicted to be responsive to irofulven, while values below the median indicate patients predicted to be non-responsive to irofulven. For a test sample from an individual patient, it is useful to compare the test sample to the reference population for the same cancer type. If the test sample is above the median for the reference population of the same cancer type, then the patient is predicted to be responsive to irofulven treatment. If the test sample is below the median for the reference population of the same cancer type, then the patient is predicted to be non-responsive to irofulven treatment. This method for predicting patient responsiveness can also be used when the reference cancer population consists of only two patients: a patient responsive to irofulven treatment and a patient non-responsive to irofulven treatment.

Example 4

Predicting Responsiveness of Prostate Cancer Patients to Irofulven

The diagnostic methods of the present invention can be used to predict the responsiveness of a prostate cancer patient to treatment with irofulven. In particular, the prostate cancer patient may be one that has not previously received any cancer treatment or one that has received a cancer treatment other than irofulven. Moreover, the patient may be one diagnosed with prostate cancer or one with recurrence of prostate cancer. The patient may also have prostate cancer that is resistant to treatment, such as treatment with docetaxel, cabazitaxel, mitoxantrone, estramustine, prednisone, and/or surgery.

A biological sample (e.g., a prostate tissue sample) may be obtained from the patient through methods well known in the art. The sample may be frozen and/or prepared, e.g., by formalin fixation and paraffin embedding. In particular, mRNA can be isolated from the sample and a gene expression profile can be determined, e.g., using a microarray platform, such as the Affymetrix HG-U133A or HG-U133_Plus_2 array, for one or more of the biomarkers shown in Tables 1-4. One or more of the biomarkers shown in Tables 1-4 can also be measured, e.g., by sequencing or PCR-based techniques, such as those described herein.

For example, the expression level of one or more biomarkers of sensitivity to irofulven can be determined in the sample from the patient, such as one or more of ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), and GJA1 (SEQ ID NO: 218). In particular, the biomarker is ATP1B1 (SEQ ID NO: 201). The expression level of one or more biomarkers of resistance to irofulven can also be determined in the sample from the patient, such as one or more of IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and GTSF1 (SEQ ID NO: 321). In particular, the biomarker is IGLC1 (SEQ ID NO: 301, 302, 303, or 318).

The prostate cancer patient may be responsive to irofulven if the expression level of one or more of the biomarkers of sensitivity is substantially similar to the expression level of the biomarkers of sensitivity in a cell or tissue known to be sensitive to irofulven. The prostate cancer patient may also be responsive to irofulven if the expression level of one or more of the biomarkers of resistance is substantially dissimilar to the expression level of the biomarkers of resistance in a cell or tissue known to be resistant to irofulven. If the patient is predicted to be responsive, then the patient can be administered irofulven, such as irofulven administered intravenously at a dose of about 0.05 mg/kg to 5 mg/kg (e.g., about 0.1 mg/kg to 1 mg/kg, such as about 0.45 mg/kg). Conversely, if the patient is predicted to be non-responsive to irofulven treatment, then the patient can be administered one or more therapies other than irofulven, such as radiation or a therapeutic agent (e.g., docetaxel, cabazitaxel, mitoxantrone, estramustine, prednisone, and/or another therapeutic agent described herein).

Example 5

Predicting Responsiveness of Ovarian Cancer Patients to Irofulven

The diagnostic methods of the present invention can be used to predict the responsiveness of an ovarian cancer patient to treatment with irofulven. In particular, the ovarian cancer patient may be one that has not previously received any cancer treatment or one that has received a cancer treatment other than irofulven. Moreover, the patient may be one diagnosed with ovarian cancer or one with recurrence of ovarian cancer. The patient may also have ovarian cancer that is resistant to treatment, such as treatment with docetaxel, carboplatin, bevacizumab, paclitaxel, gemcitabine, doxorubicin, topotecan, etoposide, tamoxifen, and/or letrozole.

A biological sample (e.g., an ovarian tissue sample) may be obtained from the patient through methods well known in the art. The sample may be frozen and/or prepared, e.g., by formalin fixation and paraffin embedding. In particular, mRNA can be isolated from the sample and a gene expression profile can be determined, e.g., using a microarray platform, such as the Affymetrix HG-U133A or HG-U133_Plus_2 array, for one or more of the biomarkers shown in Tables 1-4. One or more of the biomarkers shown in Tables 1-4 can also be measured, e.g., by sequencing or PCR-based techniques, such as those described herein.

For example, the expression level of one or more biomarkers of sensitivity to irofulven can be determined in the sample from the patient, such as one or more of ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), and GJA1 (SEQ ID NO: 218). In particular, the biomarker is ATP1B1 (SEQ ID NO: 201). The expression level of one or more biomarkers of resistance to irofulven can also be determined in the sample from the patient, such as one or more of IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and GTSF1 (SEQ ID NO: 321). In particular, the biomarker is IGLC1 (SEQ ID NO: 301, 302, 303, or 318).

The ovarian cancer patient may be responsive to irofulven if the expression level of one or more of the biomarkers of sensitivity is substantially similar to the expression level of the biomarkers of sensitivity in a cell or tissue known to be sensitive to irofulven. The ovarian cancer patient may also be responsive to irofulven if the expression level of one or more of the biomarkers of resistance is substantially dissimilar to the expression level of the biomarkers of resistance in a cell or tissue known to be resistant to irofulven. If the patient is predicted to be responsive, then the patient can be administered irofulven, such as irofulven administered intravenously at a dose of about 0.05 mg/kg to 5 mg/kg (e.g., about 0.1 mg/kg to 1 mg/kg, such as about 0.45 mg/kg). Conversely, if the patient is predicted to be non-responsive to irofulven treatment, then the patient can be administered one or more therapies other than irofulven, such as radiation or a therapeutic agent (e.g., docetaxel, carboplatin, bevacizumab, paclitaxel, gemcitabine, doxorubicin, topotecan, etoposide, tamoxifen, letrozole, and/or another therapeutic agent described herein).

Example 6

Predicting Responsiveness of Hepatocellular Carcinoma (HCC) Patients to Irofulven The diagnostic methods of the present invention can be used to predict the responsiveness of a hepatocellular carcinoma (HCC) patient to treatment with irofulven. In particular, the HCC patient may be one that has not previously received any cancer treatment or one that has received a cancer treatment other than irofulven. Moreover, the patient may be one diagnosed with HCC or one with recurrence of HCC. The patient may also have HCC that is resistant to treatment, such as treatment with sorafenib, doxorubicin, cisplatin, fluorouracil, gemcitabine, capecitabine, oxaliplatin, interferon-alpha, and/or 5-fluorouracil (5-FU).

A biological sample (e.g., a liver tissue sample) may be obtained from the patient through methods well known in the art. The sample may be frozen and/or prepared, e.g., by formalin fixation and paraffin embedding. In particular, mRNA can be isolated from the sample and a gene expression profile can be determined, e.g., using a microarray platform, such as the Affymetrix HG-U133A or HG-U133_Plus_2 array, for one or more of the biomarkers shown in Tables 1-4. One or more of the biomarkers shown in Tables 1-4 can also be measured, e.g., by sequencing or PCR-based techniques, such as those described herein.

For example, the expression level of one or more biomarkers of sensitivity to irofulven can be determined in the sample from the patient, such as one or more of ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), and GJA1 (SEQ ID NO: 218). In particular, the biomarker is ATP1B1 (SEQ ID NO: 201). The expression level of one or more biomarkers of resistance to irofulven can also be determined in the sample from the patient, such as one or more of IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and GTSF1 (SEQ ID NO: 321). In particular, the biomarker is IGLC1 (SEQ ID NO: 301, 302, 303, or 318).

The HCC patient may be responsive to irofulven if the expression level of one or more of the biomarkers of sensitivity is substantially similar to the expression level of the biomarkers of sensitivity in a cell or tissue known to be sensitive to irofulven. The HCC patient may also be responsive to irofulven if the expression level of one or more of the biomarkers of resistance is substantially dissimilar to the expression level of the biomarkers of resistance in a cell or tissue known to be resistant to irofulven. If the patient is predicted to be responsive, then the patient can be administered irofulven, such as irofulven administered intravenously at a dose of about 0.05 mg/kg to 5 mg/kg (e.g., about 0.1 mg/kg to 1 mg/kg, such as about 0.45 mg/kg). Conversely, if the patient is predicted to be non-responsive to irofulven treatment, then the patient can be administered one or more therapies other than irofulven, such as radiation or a therapeutic agent (e.g., docetaxel, carboplatin, bevacizumab, paclitaxel, gemcitabine, doxorubicin, topotecan, etoposide, tamoxifen, letrozole, and/or another therapeutic agent described herein).

OTHER EMBODIMENTS

All publications, patents, and patent applications mentioned in the above specification are hereby incorporated by reference. Various modifications and variations of the described device and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. For example, it is anticipated that measuring the level of proteins, metabolites, identifying genetic mutations and DNA copy number variations, all will be useful in determining patient responsiveness.

The invention claimed is:

1. A method of determining irofulven sensitivity in a patient by detecting expression of a biomarker in the patient with a cancer that is resistant to one or more cancer therapies other than irofulven comprising:
   (a) isolating nucleic acid molecules obtained from a sample from the patient: and
   (b) measuring in the sample:
      i) the level of expression of one or more biomarkers of irofulven sensitivity selected from the biomarkers of Tables 1 and 3; and/or
      ii) the level of expression of one or more biomarkers of irofulven resistance selected from the biomarkers of Tables 2 and 4; and
   (c) determining irofulven sensitivity in the patient based on the level of expression of the one or more biomarkers of irofulven sensitivity and/or the one or more biomarkers of irofulven resistance.

2. A method of determining responsiveness of a cancer in a patient having cancer to irofulven comprising:
   (a) contacting one or more nucleic acid molecules obtained from a sample from the patient with a device comprising:
      i) one or more single-stranded nucleic acid molecules capable of specifically hybridizing with the nucleotides of one or more biomarkers of irofulven sensitivity selected from the biomarkers of Tables 1 and 3; and/or
      ii) one or more single-stranded nucleic acid molecules capable of specifically hybridizing with the nucleotides of one or more biomarkers of irofulven resistance selected from the biomarkers of Tables 2 and 4;
   (b) measuring hybridization, or an amplification product resulting from hybridization, between the one or more nucleic acid molecules from the patient and the single-stranded nucleic acid molecules of the device to detect a level of expression of one or more of the biomarkers of irofulven sensitivity and/or one or more of the biomarkers of irofulven resistance; and
   (c) determining irofulven sensitivity in the patient based on the level of expression of the one or more biomarkers of irofulven sensitivity and/or the one or more biomarkers of irofulven resistance.

3. The method of claim 1, wherein one or more of the cancer therapies comprises surgery, radiation, or a therapeutic agent.

4. The method of claim 2, wherein the patient is resistant to one or more cancer therapies other than irofulven, wherein one or more of the cancer therapies comprises surgery, radiation, or a therapeutic agent.

5. The method of claim 1, wherein the biomarker of sensitivity is selected from one or more of ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), and GJA1 (SEQ ID NO: 218) and/or the biomarker of resistance is selected from one or more of IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and GTSF1 (SEQ ID NO: 321).

6. The method of claim 2, wherein the biomarker of sensitivity is selected from one or more of ATP1B1 (SEQ ID NO: 201 or 219), UCHL1 (SEQ ID NO: 202), PTGR1 (SEQ ID NO: 203 or 210), NME7 (SEQ ID NO: 204), PLS3 (SEQ ID NO: 205), S100A10 (SEQ ID NO: 206), CD24 (SEQ ID NO: 207, 209, or 220), NQO1 (SEQ ID NO: 208 or 216), MYOF (SEQ ID NO: 211), LAPTM4B (SEQ ID NO: 212), CALD1 (SEQ ID NO: 213), PDGFC (SEQ ID NO: 214), BASP1 (SEQ ID NO: 215), ID1 (SEQ ID NO: 217), and GJA1 (SEQ ID NO: 218) and/or the biomarker of resistance is selected from one or more of IGLC1 (SEQ ID NO: 301, 302, 303, or 318), LAPTM5 (SEQ ID NO: 304 or 338), ARHGDIB (SEQ ID NO: 305 or 311), SLC43A3 (SEQ ID NO: 307), LCP1 (SEQ ID NO: 308), HCLS1 (SEQ ID NO: 309), CD53 (SEQ ID NO: 310), MZB1 (SEQ ID NO: 313), RASSF5 (SEQ ID NO: 314 or 386), FAM46C (SEQ ID NO: 315), RCSD1 (SEQ ID NO: 316), IGJ (SEQ ID NO: 317), LPXN (SEQ ID NO: 319), ITGB7 (SEQ ID NO: 320), and GTSF1 (SEQ ID NO: 321).

7. The method of claim 1, wherein the method is performed using a device.

8. The method of claim 2, wherein the device is a microarray.

9. The method of claim 1, wherein the method comprises performing an assay selected from the group consisting of microarray, quantitative reverse transcriptase polymerase chain reaction (qRT-PCR), RNA-seq, and Nanostring analysis.

10. The method of claim 2, wherein the method comprises performing an assay selected from the group consisting of microarray, quantitative reverse transcriptase polymerase chain reaction (qRT-PCR), RNA-seq, and Nanostring analysis.

11. The method of claim 1, wherein the level of expression of one or more of the biomarkers of sensitivity and/or one or more of the biomarkers of resistance is determined by detecting the level of mRNA transcribed from one or more genes encoding one or more of the biomarkers of Tables 1-4.

12. The method of claim 2, wherein the level of expression of one or more of the biomarkers of sensitivity and/or one or more of the biomarkers of resistance is determined by detecting the level of mRNA transcribed from one or more genes encoding one or more of the biomarkers of Tables 1-4.

13. The method of claim 1, wherein the cancer is selected from a solid tumor cancer and a hematological cancer and/or wherein the cancer is selected from the group consisting of prostate cancer, ovarian cancer, hepatocellular carcinoma (HCC), cervical cancer, renal cell carcinoma (RCC), esophageal cancer, melanoma, glioma, pancreatic cancer, gastrointestinal stromal tumors (GIST), sarcoma, estrogen receptor-positive (ERpos) breast cancer, non-small cell lung carcinoma (NSCLC), colon cancer, bladder cancer, squamous cell carcinoma of the head and neck (SCCHN), acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), and Hodgkin's lymphoma.

14. The method of claim 2, wherein the cancer is selected from a solid tumor cancer and a hematological cancer and/or wherein the cancer is selected from the group consisting of prostate cancer, ovarian cancer, hepatocellular carcinoma (HCC), cervical cancer, renal cell carcinoma (RCC), esophageal cancer, melanoma, glioma, pancreatic cancer, gastrointestinal stromal tumors (GIST), sarcoma, estrogen receptor-positive (ERpos) breast cancer, non-small cell lung carcinoma (NSCLC), colon cancer, bladder cancer, squamous cell carcinoma of the head and neck (SCCHN), acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), and Hodgkin's lymphoma.

15. The method of claim 1, wherein: (a) the sample from the patient is a tumor sample; (b) the patient exhibits cancer relapse after treatment with a therapeutic agent other than irofulven; (c) the patient exhibits cancer relapse prior to treatment with irofulven; or (d) the patient has not been administered a treatment for cancer.

16. The method of claim 2, wherein: (a) the sample from the patient is a tumor sample; (b) the patient exhibits cancer relapse after treatment with a therapeutic agent other than irofulven; (c) the patient exhibits cancer relapse prior to treatment with irofulven; or (d) the patient has not been administered a treatment for cancer.

17. The method of claim 1, wherein the biomarker of sensitivity is ATP1B1 (SEQ ID NO: 201 or 219) and/or the biomarker of resistance is IGLC1 (SEQ ID NO: 301, 302, 303, or 318).

18. The method of claim 17, wherein the biomarker of sensitivity is ATP1B1 (SEQ ID NO: 201 or 219) and the biomarker of resistance is IGLC1 (SEQ ID NO: 301, 302, 303, or 318).

19. The method of claim 2, wherein the biomarker of sensitivity is ATP1B1 (SEQ ID NO: 201 or 219) and/or the biomarker of resistance is IGLC1 (SEQ ID NO: 301, 302, 303, or 318).

20. The method of claim 19, wherein the biomarker of sensitivity is ATP1B1 (SEQ ID NO: 201 or 219) and the biomarker of resistance is IGLC1 (SEQ ID NO: 301, 302, 303, or 318).

* * * * *

SEQUENCE LISTING

```
<160> NUMBER OF SEQ ID NOS: 400

<210> SEQ ID NO 1
<211> LENGTH: 25
<212> TYPE: DNA
<213> ORGANISM: Homo sapiens

<400> SEQUENCE: 1
```
agagttgtcc aaagggtcgc ttaag                                              25

<210> SEQ ID NO 2
<211> LENGTH: 25
<212> TYPE: DNA
<213> ORGANISM: Homo sapiens

<400> SEQUENCE: 2
tgatcacaag cacaaatctt tccca                                              25

<210> SEQ ID NO 3
<211> LENGTH: 25
<212> TYPE: DNA
<213> ORGANISM: Homo sapiens

<400> SEQUENCE: 3
acaccctgct ctacaatgtt gcatc                                              25

<210> SEQ ID NO 4
<211> LENGTH: 25
<212> TYPE: DNA
<213> ORGANISM: Homo sapiens

<400> SEQUENCE: 4
aaagctgtgc tgtcggtgat acaga                                              25

<210> SEQ ID NO 5
<211> LENGTH: 25
<212> TYPE: DNA
<213> ORGANISM: Homo sapiens

<400> SEQUENCE: 5
gttacaaagt cagcaactct cctgt                                              25

<210> SEQ ID NO 6
<211> LENGTH: 25
<212> TYPE: DNA
<213> ORGANISM: Homo sapiens

<400> SEQUENCE: 6
tgcacgcata ggattgaaga cagta                                              25

<210> SEQ ID NO 7
<211> LENGTH: 25
<212> TYPE: DNA
<213> ORGANISM: Homo sapiens

<400> SEQUENCE: 7
ccagtagcag gttacgccat gtcac                                              25

<210> SEQ ID NO 8
<211> LENGTH: 25
<212> TYPE: DNA
<213> ORGANISM: Homo sapiens

<400> SEQUENCE: 8
aatacaccac tacattctgt taatc                                              25

<210> SEQ ID NO 9
<211> LENGTH: 25
<212> TYPE: DNA
<213> ORGANISM: Homo sapiens

<400> SEQUENCE: 9
gtaacgcctt gagctgggtt gattg                                          25

<210> SEQ ID NO 10
<211> LENGTH: 25
<212> TYPE: DNA
<213> ORGANISM: Homo sapiens

<400> SEQUENCE: 10
gtttggtgca ctctcgtggg agaca                                          25

<210> SEQ ID NO 11
<211> LENGTH: 25
<212> TYPE: DNA
<213> ORGANISM: Homo sapiens

<400> SEQUENCE: 11
ccccagggac attccatcat tgcaa                                          25

<210> SEQ ID NO 12
<211> LENGTH: 25
<212> TYPE: DNA
<213> ORGANISM: Homo sapiens

<400> SEQUENCE: 12
caagcacaaa gttatattcc atcct                                          25

<210> SEQ ID NO 13
<211> LENGTH: 25
<212> TYPE: DNA
<213> ORGANISM: Homo sapiens

<400> SEQUENCE: 13
tgtgtaattg tttgctgtat ctccc                                          25

<210> SEQ ID NO 14
<211> LENGTH: 25
<212> TYPE: DNA
<213> ORGANISM: Homo sapiens

<400> SEQUENCE: 14
taccaaatcg accagaaacc tcctt                                          25

<210> SEQ ID NO 15
<211> LENGTH: 25
<212> TYPE: DNA
<213> ORGANISM: Homo sapiens

<400> SEQUENCE: 15
cacctgctta gggactttga actta                                          25

<210> SEQ ID NO 16
<211> LENGTH: 25
<212> TYPE: DNA
<213> ORGANISM: Homo sapiens

<400> SEQUENCE: 16
aaacttgtcc ttagattaat gtgtc                                          25

<210> SEQ ID NO 17
<211> LENGTH: 25
<212> TYPE: DNA
<213> ORGANISM: Homo sapiens

```
<400> SEQUENCE: 17
aagcggcgca accaggagat gcagc                                          25

<210> SEQ ID NO 18
<211> LENGTH: 25
<212> TYPE: DNA
<213> ORGANISM: Homo sapiens

<400> SEQUENCE: 18
gatttcaagc tgttctgaga catct                                          25

<210> SEQ ID NO 19
<211> LENGTH: 25
<212> TYPE: DNA
<213> ORGANISM: Homo sapiens

<400> SEQUENCE: 19
ttaatttcca gtcaccccaa atatg                                          25

<210> SEQ ID NO 20
<211> LENGTH: 25
<212> TYPE: DNA
<213> ORGANISM: Homo sapiens

<400> SEQUENCE: 20
aacaaggtga cattttctg ctgcc                                           25

<210> SEQ ID NO 21
<211> LENGTH: 25
<212> TYPE: DNA
<213> ORGANISM: Homo sapiens

<400> SEQUENCE: 21
gtggcttcca agtcttagaa cctca                                          25

<210> SEQ ID NO 22
<211> LENGTH: 25
<212> TYPE: DNA
<213> ORGANISM: Homo sapiens

<400> SEQUENCE: 22
aaaatccaga ctctttcgat accca                                          25

<210> SEQ ID NO 23
<211> LENGTH: 25
<212> TYPE: DNA
<213> ORGANISM: Homo sapiens

<400> SEQUENCE: 23
aacttccccc aaatctgatg gacct                                          25

<210> SEQ ID NO 24
<211> LENGTH: 25
<212> TYPE: DNA
<213> ORGANISM: Homo sapiens

<400> SEQUENCE: 24
aattccgcaa acactacgac tagag                                          25

<210> SEQ ID NO 25
<211> LENGTH: 25
<212> TYPE: DNA
```

<213> ORGANISM: Homo sapiens

<400> SEQUENCE: 25
cgtggccatc cctgtgaggg tgacg                                          25

<210> SEQ ID NO 26
<211> LENGTH: 25
<212> TYPE: DNA
<213> ORGANISM: Homo sapiens

<400> SEQUENCE: 26
ttcatcttca ctgcaattttt gtgta                                         25

<210> SEQ ID NO 27
<211> LENGTH: 25
<212> TYPE: DNA
<213> ORGANISM: Homo sapiens

<400> SEQUENCE: 27
acatggggtg acatgcctcg tatgt                                          25

<210> SEQ ID NO 28
<211> LENGTH: 25
<212> TYPE: DNA
<213> ORGANISM: Homo sapiens

<400> SEQUENCE: 28
ctcaccatgc ttccagctaa caggt                                          25

<210> SEQ ID NO 29
<211> LENGTH: 25
<212> TYPE: DNA
<213> ORGANISM: Homo sapiens

<400> SEQUENCE: 29
gagggtgacg ttagcattac cccca                                          25

<210> SEQ ID NO 30
<211> LENGTH: 25
<212> TYPE: DNA
<213> ORGANISM: Homo sapiens

<400> SEQUENCE: 30
tgatgacttc atgctttatt atgcc                                          25

<210> SEQ ID NO 31
<211> LENGTH: 25
<212> TYPE: DNA
<213> ORGANISM: Homo sapiens

<400> SEQUENCE: 31
acagctgtca gaacctcgag agcag                                          25

<210> SEQ ID NO 32
<211> LENGTH: 25
<212> TYPE: DNA
<213> ORGANISM: Homo sapiens

<400> SEQUENCE: 32
tctctgcaag ggatccacgg ggaca                                          25

<210> SEQ ID NO 33
<211> LENGTH: 25

```
<212> TYPE: DNA
<213> ORGANISM: Homo sapiens

<400> SEQUENCE: 33
gcaaatggca gtgtgctgtc acctg                                              25

<210> SEQ ID NO 34
<211> LENGTH: 25
<212> TYPE: DNA
<213> ORGANISM: Homo sapiens

<400> SEQUENCE: 34
gacacgaggc ccttggcagg gaata                                              25

<210> SEQ ID NO 35
<211> LENGTH: 25
<212> TYPE: DNA
<213> ORGANISM: Homo sapiens

<400> SEQUENCE: 35
acaatgcatt tcctcagtga tcact                                              25

<210> SEQ ID NO 36
<211> LENGTH: 25
<212> TYPE: DNA
<213> ORGANISM: Homo sapiens

<400> SEQUENCE: 36
acacgtgctt gtggacatca gcctc                                              25

<210> SEQ ID NO 37
<211> LENGTH: 25
<212> TYPE: DNA
<213> ORGANISM: Homo sapiens

<400> SEQUENCE: 37
ggcgctgtac ggcgagagtg acctc                                              25

<210> SEQ ID NO 38
<211> LENGTH: 25
<212> TYPE: DNA
<213> ORGANISM: Homo sapiens

<400> SEQUENCE: 38
tggccagttt ttcatgcatg cagct                                              25

<210> SEQ ID NO 39
<211> LENGTH: 25
<212> TYPE: DNA
<213> ORGANISM: Homo sapiens

<400> SEQUENCE: 39
aagagtcagc tgatgccaga aggaa                                              25

<210> SEQ ID NO 40
<211> LENGTH: 25
<212> TYPE: DNA
<213> ORGANISM: Homo sapiens

<400> SEQUENCE: 40
gaaaccattg tggaattgcc tcagc                                              25

<210> SEQ ID NO 41
```

-continued

```
<211> LENGTH: 25
<212> TYPE: DNA
<213> ORGANISM: Homo sapiens

<400> SEQUENCE: 41
acttacagct taacccattt tcaag                                              25

<210> SEQ ID NO 42
<211> LENGTH: 25
<212> TYPE: DNA
<213> ORGANISM: Homo sapiens

<400> SEQUENCE: 42
aagcccttgt attttgctga tcagc                                              25

<210> SEQ ID NO 43
<211> LENGTH: 25
<212> TYPE: DNA
<213> ORGANISM: Homo sapiens

<400> SEQUENCE: 43
gaagaaatcc gtgaggcatt ccgag                                              25

<210> SEQ ID NO 44
<211> LENGTH: 25
<212> TYPE: DNA
<213> ORGANISM: Homo sapiens

<400> SEQUENCE: 44
gaacactctt gctttattcc agaat                                              25

<210> SEQ ID NO 45
<211> LENGTH: 25
<212> TYPE: DNA
<213> ORGANISM: Homo sapiens

<400> SEQUENCE: 45
aatttggtca agtctactct tccgt                                              25

<210> SEQ ID NO 46
<211> LENGTH: 25
<212> TYPE: DNA
<213> ORGANISM: Homo sapiens

<400> SEQUENCE: 46
agaaaaagcg gtacgatgcc ttcct                                              25

<210> SEQ ID NO 47
<211> LENGTH: 25
<212> TYPE: DNA
<213> ORGANISM: Homo sapiens

<400> SEQUENCE: 47
cagtaaccac atgcggctgt ttaaa                                              25

<210> SEQ ID NO 48
<211> LENGTH: 25
<212> TYPE: DNA
<213> ORGANISM: Homo sapiens

<400> SEQUENCE: 48
taaccaagga ggggccagtg gattc                                              25
```

```
<210> SEQ ID NO 49
<211> LENGTH: 25
<212> TYPE: DNA
<213> ORGANISM: Homo sapiens

<400> SEQUENCE: 49
aacactaggg gctggcccac tagga                                          25

<210> SEQ ID NO 50
<211> LENGTH: 25
<212> TYPE: DNA
<213> ORGANISM: Homo sapiens

<400> SEQUENCE: 50
cttttatggg gccctgtcca ggtag                                          25

<210> SEQ ID NO 51
<211> LENGTH: 25
<212> TYPE: DNA
<213> ORGANISM: Homo sapiens

<400> SEQUENCE: 51
ctgccttctt ccaggatcag gggtt                                          25

<210> SEQ ID NO 52
<211> LENGTH: 25
<212> TYPE: DNA
<213> ORGANISM: Homo sapiens

<400> SEQUENCE: 52
aatagacact ccccgaagtc ttttg                                          25

<210> SEQ ID NO 53
<211> LENGTH: 25
<212> TYPE: DNA
<213> ORGANISM: Homo sapiens

<400> SEQUENCE: 53
acacagagac ttttgctccg attct                                          25

<210> SEQ ID NO 54
<211> LENGTH: 25
<212> TYPE: DNA
<213> ORGANISM: Homo sapiens

<400> SEQUENCE: 54
gtagcatttc cctgcagatg gtaca                                          25

<210> SEQ ID NO 55
<211> LENGTH: 25
<212> TYPE: DNA
<213> ORGANISM: Homo sapiens

<400> SEQUENCE: 55
tttttagttc tccttgattc tttgt                                          25

<210> SEQ ID NO 56
<211> LENGTH: 25
<212> TYPE: DNA
<213> ORGANISM: Homo sapiens

<400> SEQUENCE: 56
atgaccaggt taaatccctc tacat                                          25
```

```
<210> SEQ ID NO 57
<211> LENGTH: 25
<212> TYPE: DNA
<213> ORGANISM: Homo sapiens

<400> SEQUENCE: 57
agctctgcag tattcaactg ttgat                                  25

<210> SEQ ID NO 58
<211> LENGTH: 25
<212> TYPE: DNA
<213> ORGANISM: Homo sapiens

<400> SEQUENCE: 58
aaccaaaaga atttgcaccc cgctg                                  25

<210> SEQ ID NO 59
<211> LENGTH: 25
<212> TYPE: DNA
<213> ORGANISM: Homo sapiens

<400> SEQUENCE: 59
gagctcactg tgggatgggg ttgac                                  25

<210> SEQ ID NO 60
<211> LENGTH: 25
<212> TYPE: DNA
<213> ORGANISM: Homo sapiens

<400> SEQUENCE: 60
gtaatctaat atggccacag tagtc                                  25

<210> SEQ ID NO 61
<211> LENGTH: 25
<212> TYPE: DNA
<213> ORGANISM: Homo sapiens

<400> SEQUENCE: 61
aatagccaca tttagaacac ttttt                                  25

<210> SEQ ID NO 62
<211> LENGTH: 25
<212> TYPE: DNA
<213> ORGANISM: Homo sapiens

<400> SEQUENCE: 62
aatctgctgg agtttcatgt acaag                                  25

<210> SEQ ID NO 63
<211> LENGTH: 25
<212> TYPE: DNA
<213> ORGANISM: Homo sapiens

<400> SEQUENCE: 63
aattagattt gtctctggga atgtg                                  25

<210> SEQ ID NO 64
<211> LENGTH: 25
<212> TYPE: DNA
<213> ORGANISM: Homo sapiens

<400> SEQUENCE: 64
aaccatcaac attgctgttc aaaga                                  25
```

<210> SEQ ID NO 65
<211> LENGTH: 25
<212> TYPE: DNA
<213> ORGANISM: Homo sapiens

<400> SEQUENCE: 65
cactttaacc cacgcttcaa tgaga                                  25

<210> SEQ ID NO 66
<211> LENGTH: 25
<212> TYPE: DNA
<213> ORGANISM: Homo sapiens

<400> SEQUENCE: 66
tcggcaactt acacacattg aaaat                                  25

<210> SEQ ID NO 67
<211> LENGTH: 25
<212> TYPE: DNA
<213> ORGANISM: Homo sapiens

<400> SEQUENCE: 67
tgtacacaac tcacatcctt catat                                  25

<210> SEQ ID NO 68
<211> LENGTH: 25
<212> TYPE: DNA
<213> ORGANISM: Homo sapiens

<400> SEQUENCE: 68
ttcggggaca atctggtcac ccgct                                  25

<210> SEQ ID NO 69
<211> LENGTH: 25
<212> TYPE: DNA
<213> ORGANISM: Homo sapiens

<400> SEQUENCE: 69
atctgaactt tcaaagcttg ctatt                                  25

<210> SEQ ID NO 70
<211> LENGTH: 25
<212> TYPE: DNA
<213> ORGANISM: Homo sapiens

<400> SEQUENCE: 70
gagtgtccac tattgattgt attat                                  25

<210> SEQ ID NO 71
<211> LENGTH: 25
<212> TYPE: DNA
<213> ORGANISM: Homo sapiens

<400> SEQUENCE: 71
gcaggagaag aacaccctgc cgacc                                  25

<210> SEQ ID NO 72
<211> LENGTH: 25
<212> TYPE: DNA
<213> ORGANISM: Homo sapiens

<400> SEQUENCE: 72
atattggttc atgtgcttgt gtata                                              25

<210> SEQ ID NO 73
<211> LENGTH: 25
<212> TYPE: DNA
<213> ORGANISM: Homo sapiens

<400> SEQUENCE: 73
agcttttggc tgcgtaactg tgaac                                              25

<210> SEQ ID NO 74
<211> LENGTH: 25
<212> TYPE: DNA
<213> ORGANISM: Homo sapiens

<400> SEQUENCE: 74
tgaacgaatt tattttcccc tcagt                                              25

<210> SEQ ID NO 75
<211> LENGTH: 25
<212> TYPE: DNA
<213> ORGANISM: Homo sapiens

<400> SEQUENCE: 75
acagttcacc aaatagctag tcatg                                              25

<210> SEQ ID NO 76
<211> LENGTH: 25
<212> TYPE: DNA
<213> ORGANISM: Homo sapiens

<400> SEQUENCE: 76
catttcacca ctcatgctac taatc                                              25

<210> SEQ ID NO 77
<211> LENGTH: 25
<212> TYPE: DNA
<213> ORGANISM: Homo sapiens

<400> SEQUENCE: 77
gtggagttga tgactttctg ttttc                                              25

<210> SEQ ID NO 78
<211> LENGTH: 25
<212> TYPE: DNA
<213> ORGANISM: Homo sapiens

<400> SEQUENCE: 78
ggccaatgag aactcaactc ctggc                                              25

<210> SEQ ID NO 79
<211> LENGTH: 25
<212> TYPE: DNA
<213> ORGANISM: Homo sapiens

<400> SEQUENCE: 79
aaagcctttt gtcctccaaa gatga                                              25

<210> SEQ ID NO 80
<211> LENGTH: 25
<212> TYPE: DNA
<213> ORGANISM: Homo sapiens

<400> SEQUENCE: 80

```
tgcaagctgc gaggatggct tgggc                                            25

<210> SEQ ID NO 81
<211> LENGTH: 25
<212> TYPE: DNA
<213> ORGANISM: Homo sapiens

<400> SEQUENCE: 81
gaggggtgac acagtgttcc ctcct                                            25

<210> SEQ ID NO 82
<211> LENGTH: 25
<212> TYPE: DNA
<213> ORGANISM: Homo sapiens

<400> SEQUENCE: 82
agcttttcgt cttcagtgtc ttaat                                            25

<210> SEQ ID NO 83
<211> LENGTH: 25
<212> TYPE: DNA
<213> ORGANISM: Homo sapiens

<400> SEQUENCE: 83
ccagagctta ttggccactg ggtct                                            25

<210> SEQ ID NO 84
<211> LENGTH: 25
<212> TYPE: DNA
<213> ORGANISM: Homo sapiens

<400> SEQUENCE: 84
cattcttcct ctccagatat ttttg                                            25

<210> SEQ ID NO 85
<211> LENGTH: 25
<212> TYPE: DNA
<213> ORGANISM: Homo sapiens

<400> SEQUENCE: 85 atggttttg ctctagaata ccgta                                             25

<210> SEQ ID NO 86
<211> LENGTH: 25
<212> TYPE: DNA
<213> ORGANISM: Homo sapiens

<400> SEQUENCE: 86
ggaccaaagt cactaatgtt ttaca                                            25

<210> SEQ ID NO 87
<211> LENGTH: 25
<212> TYPE: DNA
<213> ORGANISM: Homo sapiens

<400> SEQUENCE: 87
tcagcctggg cagtcttacc aaaat                                            25

<210> SEQ ID NO 88
<211> LENGTH: 25
<212> TYPE: DNA
<213> ORGANISM: Homo sapiens
```

```
<400> SEQUENCE: 88
cctaggccat tgcagcatcc ttaga                                             25

<210> SEQ ID NO 89
<211> LENGTH: 25
<212> TYPE: DNA
<213> ORGANISM: Homo sapiens

<400> SEQUENCE: 89
cacccctagg aactcagtcc tgtac                                             25

<210> SEQ ID NO 90
<211> LENGTH: 25
<212> TYPE: DNA
<213> ORGANISM: Homo sapiens

<400> SEQUENCE: 90
taaggtaagg tatccaccct cgatg                                             25

<210> SEQ ID NO 91
<211> LENGTH: 25
<212> TYPE: DNA
<213> ORGANISM: Homo sapiens

<400> SEQUENCE: 91
tagaactaag ggttcccgac tctga                                             25

<210> SEQ ID NO 92
<211> LENGTH: 25
<212> TYPE: DNA
<213> ORGANISM: Homo sapiens

<400> SEQUENCE: 92
tccattttat tcttctgagt gtcta                                             25

<210> SEQ ID NO 93
<211> LENGTH: 25
<212> TYPE: DNA
<213> ORGANISM: Homo sapiens

<400> SEQUENCE: 93
cagcatcaac ccctatggca tgcat                                             25

<210> SEQ ID NO 94
<211> LENGTH: 25
<212> TYPE: DNA
<213> ORGANISM: Homo sapiens

<400> SEQUENCE: 94
aaagtactgc ttgttctctg tggag                                             25

<210> SEQ ID NO 95
<211> LENGTH: 25
<212> TYPE: DNA
<213> ORGANISM: Homo sapiens

<400> SEQUENCE: 95
agagaacctg ttcatctttg gcatg                                             25

<210> SEQ ID NO 96
<211> LENGTH: 25
<212> TYPE: DNA
<213> ORGANISM: Homo sapiens
```

-continued

```
<400> SEQUENCE: 96
ccaattgtgc tgagtctcct actag                                        25

<210> SEQ ID NO 97
<211> LENGTH: 25
<212> TYPE: DNA
<213> ORGANISM: Homo sapiens

<400> SEQUENCE: 97
tagcctttac tgtttgatat accaa                                        25

<210> SEQ ID NO 98
<211> LENGTH: 25
<212> TYPE: DNA
<213> ORGANISM: Homo sapiens

<400> SEQUENCE: 98
gagcattgct tacaggtttt ttgtt                                        25

<210> SEQ ID NO 99
<211> LENGTH: 25
<212> TYPE: DNA
<213> ORGANISM: Homo sapiens

<400> SEQUENCE: 99
tggggcctag aagttacaga gcatc                                        25

<210> SEQ ID NO 100
<211> LENGTH: 25
<212> TYPE: DNA
<213> ORGANISM: Homo sapiens

<400> SEQUENCE: 100
gagacttcgg cggaccatta ggaat                                        25

<210> SEQ ID NO 101
<211> LENGTH: 25
<212> TYPE: DNA
<213> ORGANISM: Homo sapiens

<400> SEQUENCE: 101
gctcacctga aagaggtatg ctctc                                        25

<210> SEQ ID NO 102
<211> LENGTH: 25
<212> TYPE: DNA
<213> ORGANISM: Homo sapiens

<400> SEQUENCE: 102
aaagaagctg gggcttgctc tgacg                                        25

<210> SEQ ID NO 103
<211> LENGTH: 25
<212> TYPE: DNA
<213> ORGANISM: Homo sapiens

<400> SEQUENCE: 103
gtaacattgg gtcctgggtc tttca                                        25

<210> SEQ ID NO 104
<211> LENGTH: 25
<212> TYPE: DNA
```

<213> ORGANISM: Homo sapiens

<400> SEQUENCE: 104
gaggatgacg ccagaggcac ggtcg                                25

<210> SEQ ID NO 105
<211> LENGTH: 25
<212> TYPE: DNA
<213> ORGANISM: Homo sapiens

<400> SEQUENCE: 105
gatcaaactc agcagtactt gggtg                                25

<210> SEQ ID NO 106
<211> LENGTH: 25
<212> TYPE: DNA
<213> ORGANISM: Homo sapiens

<400> SEQUENCE: 106
aaagggcaag atctcatttc aattt                                25

<210> SEQ ID NO 107
<211> LENGTH: 25
<212> TYPE: DNA
<213> ORGANISM: Homo sapiens

<400> SEQUENCE: 107
actgtgatat aggtactctg attta                                25

<210> SEQ ID NO 108
<211> LENGTH: 25
<212> TYPE: DNA
<213> ORGANISM: Homo sapiens

<400> SEQUENCE: 108
gtacgtctag attgtgtggt ttgcc                                25

<210> SEQ ID NO 109
<211> LENGTH: 25
<212> TYPE: DNA
<213> ORGANISM: Homo sapiens

<400> SEQUENCE: 109
caacgactcc acaatcctag ataag                                25

<210> SEQ ID NO 110
<211> LENGTH: 25
<212> TYPE: DNA
<213> ORGANISM: Homo sapiens

<400> SEQUENCE: 110
gtaccccgag ctgcggtgtt tgaag                                25

<210> SEQ ID NO 111
<211> LENGTH: 25
<212> TYPE: DNA
<213> ORGANISM: Homo sapiens

<400> SEQUENCE: 111
accggacacc accagacaat aggat                                25

<210> SEQ ID NO 112
<211> LENGTH: 25

```
<212> TYPE: DNA
<213> ORGANISM: Homo sapiens

<400> SEQUENCE: 112
cttgggacat tgccttttct agccc                                              25

<210> SEQ ID NO 113
<211> LENGTH: 25
<212> TYPE: DNA
<213> ORGANISM: Homo sapiens

<400> SEQUENCE: 113
caaacactca gccccgaaga tgttg                                              25

<210> SEQ ID NO 114
<211> LENGTH: 25
<212> TYPE: DNA
<213> ORGANISM: Homo sapiens

<400> SEQUENCE: 114
atgtggctgt taatatgtgc ttgtt                                              25

<210> SEQ ID NO 115
<211> LENGTH: 25
<212> TYPE: DNA
<213> ORGANISM: Homo sapiens

<400> SEQUENCE: 115
gatcgccagg ttctacaagc tgcac                                              25

<210> SEQ ID NO 116
<211> LENGTH: 25
<212> TYPE: DNA
<213> ORGANISM: Homo sapiens

<400> SEQUENCE: 116
ctttaggcct gtttggctcc gaagc                                              25

<210> SEQ ID NO 117
<211> LENGTH: 25
<212> TYPE: DNA
<213> ORGANISM: Homo sapiens

<400> SEQUENCE: 117
ttgtgtgatc cagcgtcatt tccac                                              25

<210> SEQ ID NO 118
<211> LENGTH: 25
<212> TYPE: DNA
<213> ORGANISM: Homo sapiens

<400> SEQUENCE: 118
gtatatgtct gcaatcatgg atagg                                              25

<210> SEQ ID NO 119
<211> LENGTH: 25
<212> TYPE: DNA
<213> ORGANISM: Homo sapiens

<400> SEQUENCE: 119
gggtacaagc tccagaacag taacc                                              25

<210> SEQ ID NO 120
```

```
<211> LENGTH: 25
<212> TYPE: DNA
<213> ORGANISM: Homo sapiens

<400> SEQUENCE: 120
gtggaagctg tggtcacttt cgcag                                              25

<210> SEQ ID NO 121
<211> LENGTH: 25
<212> TYPE: DNA
<213> ORGANISM: Homo sapiens

<400> SEQUENCE: 121
gaggcttggc cactggatgt tttca                                              25

<210> SEQ ID NO 122
<211> LENGTH: 25
<212> TYPE: DNA
<213> ORGANISM: Homo sapiens

<400> SEQUENCE: 122
tgtggttgat agccagtcac tgcct                                              25

<210> SEQ ID NO 123
<211> LENGTH: 25
<212> TYPE: DNA
<213> ORGANISM: Homo sapiens

<400> SEQUENCE: 123
tttggaggca atcctacctt gcttt                                              25

<210> SEQ ID NO 124
<211> LENGTH: 25
<212> TYPE: DNA
<213> ORGANISM: Homo sapiens

<400> SEQUENCE: 124
acctcatgtc cacgcaaagc ttggg                                              25

<210> SEQ ID NO 125
<211> LENGTH: 25
<212> TYPE: DNA
<213> ORGANISM: Homo sapiens

<400> SEQUENCE: 125
agtgggatgt ctcttcagtt tatga                                              25

<210> SEQ ID NO 126
<211> LENGTH: 25
<212> TYPE: DNA
<213> ORGANISM: Homo sapiens

<400> SEQUENCE: 126
tggtgggcca caaggtgaac ctgca                                              25

<210> SEQ ID NO 127
<211> LENGTH: 25
<212> TYPE: DNA
<213> ORGANISM: Homo sapiens

<400> SEQUENCE: 127
taaccaccga tcagcacagc tgtcc                                              25
```

```
<210> SEQ ID NO 128
<211> LENGTH: 25
<212> TYPE: DNA
<213> ORGANISM: Homo sapiens

<400> SEQUENCE: 128
cataggcgaa tctgttctgc ccgag                                    25

<210> SEQ ID NO 129
<211> LENGTH: 25
<212> TYPE: DNA
<213> ORGANISM: Homo sapiens

<400> SEQUENCE: 129
acatatactt attacccagt acagt                                    25

<210> SEQ ID NO 130
<211> LENGTH: 26
<212> TYPE: DNA
<213> ORGANISM: Homo sapiens

<400> SEQUENCE: 130
gaacatgtac aatttgccac tgggas                                   26

<210> SEQ ID NO 131
<211> LENGTH: 25
<212> TYPE: DNA
<213> ORGANISM: Homo sapiens

<400> SEQUENCE: 131
atgttgtatt ggctatgatg gtgac                                    25

<210> SEQ ID NO 132
<211> LENGTH: 25
<212> TYPE: DNA
<213> ORGANISM: Homo sapiens

<400> SEQUENCE: 132
aaaggtgtga ccagtcattg cccct                                    25

<210> SEQ ID NO 133
<211> LENGTH: 25
<212> TYPE: DNA
<213> ORGANISM: Homo sapiens

<400> SEQUENCE: 133
atttctaacc ctgcaacttt tgcca                                    25

<210> SEQ ID NO 134
<211> LENGTH: 25
<212> TYPE: DNA
<213> ORGANISM: Homo sapiens

<400> SEQUENCE: 134
aaaagccaca gcatacatcc tgtcc                                    25

<210> SEQ ID NO 135
<211> LENGTH: 25
<212> TYPE: DNA
<213> ORGANISM: Homo sapiens

<400> SEQUENCE: 135
aaatcttagg tttgcttatg cccag                                    25
```

<210> SEQ ID NO 136
<211> LENGTH: 25
<212> TYPE: DNA
<213> ORGANISM: Homo sapiens

<400> SEQUENCE: 136
agagaaccca ccatggtgct gtctc                                  25

<210> SEQ ID NO 137
<211> LENGTH: 25
<212> TYPE: DNA
<213> ORGANISM: Homo sapiens

<400> SEQUENCE: 137
aatttaatgg tatcttcctt gctgg                                  25

<210> SEQ ID NO 138
<211> LENGTH: 25
<212> TYPE: DNA
<213> ORGANISM: Homo sapiens

<400> SEQUENCE: 138
cggagaggtg gtgttacgct ttgct                                  25

<210> SEQ ID NO 139
<211> LENGTH: 25
<212> TYPE: DNA
<213> ORGANISM: Homo sapiens

<400> SEQUENCE: 139
agctgctcac aactgggtca acgct                                  25

<210> SEQ ID NO 140
<211> LENGTH: 25
<212> TYPE: DNA
<213> ORGANISM: Homo sapiens

<400> SEQUENCE: 140
ggtcccagcc aattgtgatg atcct                                  25

<210> SEQ ID NO 141
<211> LENGTH: 25
<212> TYPE: DNA
<213> ORGANISM: Homo sapiens

<400> SEQUENCE: 141
gtcactcaac gtggtcccta gaaca                                  25

<210> SEQ ID NO 142
<211> LENGTH: 25
<212> TYPE: DNA
<213> ORGANISM: Homo sapiens

<400> SEQUENCE: 142
gacgactgag gcaagagggc gccag                                  25

<210> SEQ ID NO 143
<211> LENGTH: 25
<212> TYPE: DNA
<213> ORGANISM: Homo sapiens

<400> SEQUENCE: 143
ggttccttgt ctattgggtg atttg                                  25

```
<210> SEQ ID NO 144
<211> LENGTH: 25
<212> TYPE: DNA
<213> ORGANISM: Homo sapiens

<400> SEQUENCE: 144
gtgactgata tttcccacct tgtca                                           25

<210> SEQ ID NO 145
<211> LENGTH: 25
<212> TYPE: DNA
<213> ORGANISM: Homo sapiens

<400> SEQUENCE: 145
gaagaaggcc taatctctct ctttt                                           25

<210> SEQ ID NO 146
<211> LENGTH: 25
<212> TYPE: DNA
<213> ORGANISM: Homo sapiens

<400> SEQUENCE: 146
aagtgcataa ctattttga ccagc                                            25

<210> SEQ ID NO 147
<211> LENGTH: 25
<212> TYPE: DNA
<213> ORGANISM: Homo sapiens

<400> SEQUENCE: 147
tggcatcacc gttgtggact ggccg                                           25

<210> SEQ ID NO 148
<211> LENGTH: 25
<212> TYPE: DNA
<213> ORGANISM: Homo sapiens

<400> SEQUENCE: 148
tggacacatt ttatcctgat ccaca                                           25

<210> SEQ ID NO 149
<211> LENGTH: 25
<212> TYPE: DNA
<213> ORGANISM: Homo sapiens

<400> SEQUENCE: 149
tggcgagtat ggtgcggagg ccctg                                           25

<210> SEQ ID NO 150
<211> LENGTH: 25
<212> TYPE: DNA
<213> ORGANISM: Homo sapiens

<400> SEQUENCE: 150
gtggtctatg ttggcgtctg gatcc                                           25

<210> SEQ ID NO 151
<211> LENGTH: 25
<212> TYPE: DNA
<213> ORGANISM: Homo sapiens

<400> SEQUENCE: 151
```

```
tggacctaga ctgtgctttt ctgtc                                          25

<210> SEQ ID NO 152
<211> LENGTH: 25
<212> TYPE: DNA
<213> ORGANISM: Homo sapiens

<400> SEQUENCE: 152
ctgacctcca ataccgtta agctg                                           25

<210> SEQ ID NO 153
<211> LENGTH: 25
<212> TYPE: DNA
<213> ORGANISM: Homo sapiens

<400> SEQUENCE: 153
cgcacaagct tcgggtggac ccggt                                          25

<210> SEQ ID NO 154
<211> LENGTH: 25
<212> TYPE: DNA
<213> ORGANISM: Homo sapiens

<400> SEQUENCE: 154
gatgtgatgt gaatactctt cccac                                          25

<210> SEQ ID NO 155
<211> LENGTH: 25
<212> TYPE: DNA
<213> ORGANISM: Homo sapiens

<400> SEQUENCE: 155
tcatgtgcat tcaagctgtg tgaca                                          25

<210> SEQ ID NO 156
<211> LENGTH: 25
<212> TYPE: DNA
<213> ORGANISM: Homo sapiens

<400> SEQUENCE: 156
agcacatcat ggttggcctt atcct                                          25

<210> SEQ ID NO 157
<211> LENGTH: 25
<212> TYPE: DNA
<213> ORGANISM: Homo sapiens

<400> SEQUENCE: 157
gaaattcgtc atctgttgac actta                                          25

<210> SEQ ID NO 158
<211> LENGTH: 25
<212> TYPE: DNA
<213> ORGANISM: Homo sapiens

<400> SEQUENCE: 158
gcagctatct taccagactg tgcct                                          25

<210> SEQ ID NO 159
<211> LENGTH: 25
<212> TYPE: DNA
<213> ORGANISM: Homo sapiens

<400> SEQUENCE: 159
```
aaatgtgagg cagctttcgc cacga                                    25

<210> SEQ ID NO 160
<211> LENGTH: 25
<212> TYPE: DNA
<213> ORGANISM: Homo sapiens

<400> SEQUENCE: 160
cactgcactg ccattgtctt ttggt                                    25

<210> SEQ ID NO 161
<211> LENGTH: 25
<212> TYPE: DNA
<213> ORGANISM: Homo sapiens

<400> SEQUENCE: 161
tcctgtgtgg tgtgtctact gtgag                                    25

<210> SEQ ID NO 162
<211> LENGTH: 25
<212> TYPE: DNA
<213> ORGANISM: Homo sapiens

<400> SEQUENCE: 162
tgttttttac agccaaacct ctgtc                                    25

<210> SEQ ID NO 163
<211> LENGTH: 25
<212> TYPE: DNA
<213> ORGANISM: Homo sapiens

<400> SEQUENCE: 163
cctccctctg aggcgtgagg actcg                                    25

<210> SEQ ID NO 164
<211> LENGTH: 25
<212> TYPE: DNA
<213> ORGANISM: Homo sapiens

<400> SEQUENCE: 164
aaagcccatc ctgagacatc ttgct                                    25

<210> SEQ ID NO 165
<211> LENGTH: 25
<212> TYPE: DNA
<213> ORGANISM: Homo sapiens

<400> SEQUENCE: 165
ggttttcata tgagctacac attgt                                    25

<210> SEQ ID NO 166
<211> LENGTH: 25
<212> TYPE: DNA
<213> ORGANISM: Homo sapiens

<400> SEQUENCE: 166
tcaaggccgc ctggggtaag gtcgg                                    25

<210> SEQ ID NO 167
<211> LENGTH: 25
<212> TYPE: DNA
<213> ORGANISM: Homo sapiens

<400> SEQUENCE: 167
aacagctgta ttatcttaaa cccac                                    25

<210> SEQ ID NO 168
<211> LENGTH: 25
<212> TYPE: DNA
<213> ORGANISM: Homo sapiens

<400> SEQUENCE: 168
cagttccctg gctgtttcta gagac                                    25

<210> SEQ ID NO 169
<211> LENGTH: 25
<212> TYPE: DNA
<213> ORGANISM: Homo sapiens

<400> SEQUENCE: 169
agctacgcaa gctgaaggaa gccat                                    25

<210> SEQ ID NO 170
<211> LENGTH: 25
<212> TYPE: DNA
<213> ORGANISM: Homo sapiens

<400> SEQUENCE: 170
cgcccatccg tgctatgaca tggag                                    25

<210> SEQ ID NO 171
<211> LENGTH: 25
<212> TYPE: DNA
<213> ORGANISM: Homo sapiens

<400> SEQUENCE: 171
gtatgtctcg tggtaggact gtaga                                    25

<210> SEQ ID NO 172
<211> LENGTH: 25
<212> TYPE: DNA
<213> ORGANISM: Homo sapiens

<400> SEQUENCE: 172
gaacagcctt gggagtcatc tttgc                                    25

<210> SEQ ID NO 173
<211> LENGTH: 25
<212> TYPE: DNA
<213> ORGANISM: Homo sapiens

<400> SEQUENCE: 173
gtgaagcaac cgccttagtg ctgaa                                    25

<210> SEQ ID NO 174
<211> LENGTH: 25
<212> TYPE: DNA
<213> ORGANISM: Homo sapiens

<400> SEQUENCE: 174
aaccccaatc ctctgacaga agaac                                    25

<210> SEQ ID NO 175
<211> LENGTH: 25
<212> TYPE: DNA
<213> ORGANISM: Homo sapiens

```
<400> SEQUENCE: 175
gtgtcattgc cttgaaatgc ttgct                                            25

<210> SEQ ID NO 176
<211> LENGTH: 25
<212> TYPE: DNA
<213> ORGANISM: Homo sapiens

<400> SEQUENCE: 176
gaaaagggca tttggcacca ctctc                                            25

<210> SEQ ID NO 177
<211> LENGTH: 25
<212> TYPE: DNA
<213> ORGANISM: Homo sapiens

<400> SEQUENCE: 177
gatgtctggg aacactgcat atcca                                            25

<210> SEQ ID NO 178
<211> LENGTH: 25
<212> TYPE: DNA
<213> ORGANISM: Homo sapiens

<400> SEQUENCE: 178
cccatatccc ttctgtaatt tgtac                                            25

<210> SEQ ID NO 179
<211> LENGTH: 25
<212> TYPE: DNA
<213> ORGANISM: Homo sapiens

<400> SEQUENCE: 179
ctgccttagc ttcaggaacc tcgag                                            25

<210> SEQ ID NO 180
<211> LENGTH: 25
<212> TYPE: DNA
<213> ORGANISM: Homo sapiens

<400> SEQUENCE: 180
cccttccaat ctctgttcag tgcaa                                            25

<210> SEQ ID NO 181
<211> LENGTH: 25
<212> TYPE: DNA
<213> ORGANISM: Homo sapiens

<400> SEQUENCE: 181
agtgcagagt gcttggctgt ttcct                                            25

<210> SEQ ID NO 182
<211> LENGTH: 25
<212> TYPE: DNA
<213> ORGANISM: Homo sapiens

<400> SEQUENCE: 182
tgagctggcg ctaagcatca cgcga                                            25

<210> SEQ ID NO 183
<211> LENGTH: 25
<212> TYPE: DNA
```

<213> ORGANISM: Homo sapiens

<400> SEQUENCE: 183
gacggtgctg atggacttcg atgcg                            25

<210> SEQ ID NO 184
<211> LENGTH: 25
<212> TYPE: DNA
<213> ORGANISM: Homo sapiens

<400> SEQUENCE: 184
cctataattt ctacctattg ggcct                            25

<210> SEQ ID NO 185
<211> LENGTH: 25
<212> TYPE: DNA
<213> ORGANISM: Homo sapiens

<400> SEQUENCE: 185
ggctggggac tgaattcctg atgtc                            25

<210> SEQ ID NO 186
<211> LENGTH: 25
<212> TYPE: DNA
<213> ORGANISM: Homo sapiens

<400> SEQUENCE: 186
gtcaaaggac tctcttctag gagac                            25

<210> SEQ ID NO 187
<211> LENGTH: 25
<212> TYPE: DNA
<213> ORGANISM: Homo sapiens

<400> SEQUENCE: 187
atgcccgggg aggacctgaa gttca                            25

<210> SEQ ID NO 188
<211> LENGTH: 25
<212> TYPE: DNA
<213> ORGANISM: Homo sapiens

<400> SEQUENCE: 188 ctccctttc cagaacacca ggtgt                             25

<210> SEQ ID NO 189
<211> LENGTH: 25
<212> TYPE: DNA
<213> ORGANISM: Homo sapiens

<400> SEQUENCE: 189
ttgggtacat agcccattgc cctta                            25

<210> SEQ ID NO 190
<211> LENGTH: 25
<212> TYPE: DNA
<213> ORGANISM: Homo sapiens

<400> SEQUENCE: 190
tacaagttcg gctttgagct tcctc                            25

<210> SEQ ID NO 191
<211> LENGTH: 25

```
<212> TYPE: DNA
<213> ORGANISM: Homo sapiens

<400> SEQUENCE: 191
gactcgggaa gagcagagcc accct                                  25

<210> SEQ ID NO 192
<211> LENGTH: 25
<212> TYPE: DNA
<213> ORGANISM: Homo sapiens

<400> SEQUENCE: 192
gggaaatttt ttgcgactgt acaca                                  25

<210> SEQ ID NO 193
<211> LENGTH: 25
<212> TYPE: DNA
<213> ORGANISM: Homo sapiens

<400> SEQUENCE: 193
atttttccgc aaatcagtcg gttga                                  25

<210> SEQ ID NO 194
<211> LENGTH: 25
<212> TYPE: DNA
<213> ORGANISM: Homo sapiens

<400> SEQUENCE: 194
tgttatcctt tctaattttt actga                                  25

<210> SEQ ID NO 195
<211> LENGTH: 25
<212> TYPE: DNA
<213> ORGANISM: Homo sapiens

<400> SEQUENCE: 195
ccagcaacct ctacatccag gaatg                                  25

<210> SEQ ID NO 196
<211> LENGTH: 25
<212> TYPE: DNA
<213> ORGANISM: Homo sapiens

<400> SEQUENCE: 196
gcagttcaag gatttccagc ggcgg                                  25

<210> SEQ ID NO 197
<211> LENGTH: 25
<212> TYPE: DNA
<213> ORGANISM: Homo sapiens

<400> SEQUENCE: 197
ggtcagcttc aggccttctg gaagc                                  25

<210> SEQ ID NO 198
<211> LENGTH: 25
<212> TYPE: DNA
<213> ORGANISM: Homo sapiens

<400> SEQUENCE: 198
gaagcagctt tacctacttg tttct                                  25

<210> SEQ ID NO 199
```

```
<211> LENGTH: 25
<212> TYPE: DNA
<213> ORGANISM: Homo sapiens

<400> SEQUENCE: 199
gcgtctttgt ttctatcagt ctttg                                          25

<210> SEQ ID NO 200
<211> LENGTH: 25
<212> TYPE: DNA
<213> ORGANISM: Homo sapiens

<400> SEQUENCE: 200
gacctggctg aaactcttaa aaaag                                          25

<210> SEQ ID NO 201
<211> LENGTH: 25
<212> TYPE: DNA
<213> ORGANISM: Homo sapiens

<400> SEQUENCE: 201
ggacctacac ttaatctata tgctt                                          25

<210> SEQ ID NO 202
<211> LENGTH: 25
<212> TYPE: DNA
<213> ORGANISM: Homo sapiens

<400> SEQUENCE: 202
agcccatgat gccgtggcac aggaa                                          25

<210> SEQ ID NO 203
<211> LENGTH: 25
<212> TYPE: DNA
<213> ORGANISM: Homo sapiens

<400> SEQUENCE: 203
aggatttgaa aacatgccag ctgca                                          25

<210> SEQ ID NO 204
<211> LENGTH: 25
<212> TYPE: DNA
<213> ORGANISM: Homo sapiens

<400> SEQUENCE: 204
gacacagctt tagaacatac cggag                                          25

<210> SEQ ID NO 205
<211> LENGTH: 25
<212> TYPE: DNA
<213> ORGANISM: Homo sapiens

<400> SEQUENCE: 205
tgtactcttg ctttgtcaag ctgtt                                          25

<210> SEQ ID NO 206
<211> LENGTH: 25
<212> TYPE: DNA
<213> ORGANISM: Homo sapiens

<400> SEQUENCE: 206
ggacctggac cagtgtagag atggc                                          25
```

```
<210> SEQ ID NO 207
<211> LENGTH: 25
<212> TYPE: DNA
<213> ORGANISM: Homo sapiens

<400> SEQUENCE: 207
gaacctggtc ctaagcctaa aagtg                                    25

<210> SEQ ID NO 208
<211> LENGTH: 25
<212> TYPE: DNA
<213> ORGANISM: Homo sapiens

<400> SEQUENCE: 208
atatagcatt gggcacactc cagca                                    25

<210> SEQ ID NO 209
<211> LENGTH: 25
<212> TYPE: DNA
<213> ORGANISM: Homo sapiens

<400> SEQUENCE: 209
catggtcaca cactgatgct tagat                                    25

<210> SEQ ID NO 210
<211> LENGTH: 25
<212> TYPE: DNA
<213> ORGANISM: Homo sapiens

<400> SEQUENCE: 210
aatggagagg tcctgcttga agctt                                    25

<210> SEQ ID NO 211
<211> LENGTH: 25
<212> TYPE: DNA
<213> ORGANISM: Homo sapiens

<400> SEQUENCE: 211
ccagtagcag gttacgccat gtcac                                    25

<210> SEQ ID NO 212
<211> LENGTH: 25
<212> TYPE: DNA
<213> ORGANISM: Homo sapiens

<400> SEQUENCE: 212
atatttgata tacttctgcc taaca                                    25

<210> SEQ ID NO 213
<211> LENGTH: 25
<212> TYPE: DNA
<213> ORGANISM: Homo sapiens

<400> SEQUENCE: 213
atcactgctg acttttattc caata                                    25

<210> SEQ ID NO 214
<211> LENGTH: 25
<212> TYPE: DNA
<213> ORGANISM: Homo sapiens

<400> SEQUENCE: 214
aagtagacat tcagatccag ccatt                                    25
```

```
<210> SEQ ID NO 215
<211> LENGTH: 25
<212> TYPE: DNA
<213> ORGANISM: Homo sapiens

<400> SEQUENCE: 215
tggatctcaa tgccaatcct ccatt                                           25

<210> SEQ ID NO 216
<211> LENGTH: 25
<212> TYPE: DNA
<213> ORGANISM: Homo sapiens

<400> SEQUENCE: 216
aatagtcaat ttctacttct ggaag                                           25

<210> SEQ ID NO 217
<211> LENGTH: 25
<212> TYPE: DNA
<213> ORGANISM: Homo sapiens

<400> SEQUENCE: 217
caccctcaac ggcgagatca gcgcc                                           25

<210> SEQ ID NO 218
<211> LENGTH: 25
<212> TYPE: DNA
<213> ORGANISM: Homo sapiens

<400> SEQUENCE: 218
gagtggacta ttaaatgtgc ctaaa                                           25

<210> SEQ ID NO 219
<211> LENGTH: 25
<212> TYPE: DNA
<213> ORGANISM: Homo sapiens

<400> SEQUENCE: 219
gttatgcttg tattgaatgc tgtct                                           25

<210> SEQ ID NO 220
<211> LENGTH: 25
<212> TYPE: DNA
<213> ORGANISM: Homo sapiens

<400> SEQUENCE: 220
gagaggtttg actagatgat ggatg                                           25

<210> SEQ ID NO 221
<211> LENGTH: 25
<212> TYPE: DNA
<213> ORGANISM: Homo sapiens

<400> SEQUENCE: 221
tgagcatgtc cctcacaatt gcaca                                           25

<210> SEQ ID NO 222
<211> LENGTH: 25
<212> TYPE: DNA
<213> ORGANISM: Homo sapiens

<400> SEQUENCE: 222
gtgccactaa aacagcctca ggaga                                           25
```

<210> SEQ ID NO 223
<211> LENGTH: 25
<212> TYPE: DNA
<213> ORGANISM: Homo sapiens

<400> SEQUENCE: 223
cttcattttg gagcttgtgg agttg        25

<210> SEQ ID NO 224
<211> LENGTH: 25
<212> TYPE: DNA
<213> ORGANISM: Homo sapiens

<400> SEQUENCE: 224
gcaaccatac tcagcttcaa cagaa        25

<210> SEQ ID NO 225
<211> LENGTH: 25
<212> TYPE: DNA
<213> ORGANISM: Homo sapiens

<400> SEQUENCE: 225
ttgcttctat tgtttgggcc ttgtg        25

<210> SEQ ID NO 226
<211> LENGTH: 25
<212> TYPE: DNA
<213> ORGANISM: Homo sapiens

<400> SEQUENCE: 226
gctttcacct atactggctg tggag        25

<210> SEQ ID NO 227
<211> LENGTH: 25
<212> TYPE: DNA
<213> ORGANISM: Homo sapiens

<400> SEQUENCE: 227
gagcctttgt ataggtacat tcctg        25

<210> SEQ ID NO 228
<211> LENGTH: 25
<212> TYPE: DNA
<213> ORGANISM: Homo sapiens

<400> SEQUENCE: 228
agtaagtttt gctggatttt tgtag        25

<210> SEQ ID NO 229
<211> LENGTH: 25
<212> TYPE: DNA
<213> ORGANISM: Homo sapiens

<400> SEQUENCE: 229
cagttcttga ctttggacaa tccca        25

<210> SEQ ID NO 230
<211> LENGTH: 25
<212> TYPE: DNA
<213> ORGANISM: Homo sapiens

<400> SEQUENCE: 230
catatgatgt ttgagtgctg ttgtt                                              25

<210> SEQ ID NO 231
<211> LENGTH: 25
<212> TYPE: DNA
<213> ORGANISM: Homo sapiens

<400> SEQUENCE: 231
cattctctgg ccaattcaga gtggc                                              25

<210> SEQ ID NO 232
<211> LENGTH: 25
<212> TYPE: DNA
<213> ORGANISM: Homo sapiens

<400> SEQUENCE: 232
taccaaatcg accagaaacc tcctt                                              25

<210> SEQ ID NO 233
<211> LENGTH: 25
<212> TYPE: DNA
<213> ORGANISM: Homo sapiens

<400> SEQUENCE: 233 aaagccttt gtcctccaaa gatga                                               25

<210> SEQ ID NO 234
<211> LENGTH: 25
<212> TYPE: DNA
<213> ORGANISM: Homo sapiens

<400> SEQUENCE: 234
ggcagccaca tgcacgaaga tgcta                                              25

<210> SEQ ID NO 235
<211> LENGTH: 25
<212> TYPE: DNA
<213> ORGANISM: Homo sapiens

<400> SEQUENCE: 235
ccatttcttt cactgattac accat                                              25

<210> SEQ ID NO 236
<211> LENGTH: 25
<212> TYPE: DNA
<213> ORGANISM: Homo sapiens

<400> SEQUENCE: 236
ataacctttg caaaccttca agctg                                              25

<210> SEQ ID NO 237
<211> LENGTH: 25
<212> TYPE: DNA
<213> ORGANISM: Homo sapiens

<400> SEQUENCE: 237
tttttatctt tgaccaaccg aacat                                              25

<210> SEQ ID NO 238
<211> LENGTH: 25
<212> TYPE: DNA
<213> ORGANISM: Homo sapiens

<400> SEQUENCE: 238

-continued gatacaatgc tgtgccctaa agtgt                                        25

<210> SEQ ID NO 239
<211> LENGTH: 25
<212> TYPE: DNA
<213> ORGANISM: Homo sapiens

<400> SEQUENCE: 239
tgttgacttg atgttttatc acttc                                        25

<210> SEQ ID NO 240
<211> LENGTH: 25
<212> TYPE: DNA
<213> ORGANISM: Homo sapiens

<400> SEQUENCE: 240
acacagggaa gtgactttgc tacaa                                        25

<210> SEQ ID NO 241
<211> LENGTH: 25
<212> TYPE: DNA
<213> ORGANISM: Homo sapiens

<400> SEQUENCE: 241
gtgtcaacag cacattcgac agccc                                        25

<210> SEQ ID NO 242
<211> LENGTH: 25
<212> TYPE: DNA
<213> ORGANISM: Homo sapiens

<400> SEQUENCE: 242
gctgaactga atggtacttc gtatg                                        25

<210> SEQ ID NO 243
<211> LENGTH: 25
<212> TYPE: DNA
<213> ORGANISM: Homo sapiens

<400> SEQUENCE: 243
aaagctcaat tcctattttg gtgtg                                        25

<210> SEQ ID NO 244
<211> LENGTH: 25
<212> TYPE: DNA
<213> ORGANISM: Homo sapiens

<400> SEQUENCE: 244
agaagctaca gcctggactt accac                                        25

<210> SEQ ID NO 245
<211> LENGTH: 25
<212> TYPE: DNA
<213> ORGANISM: Homo sapiens

<400> SEQUENCE: 245
cgctcagtgc tcttactaga tgaac                                        25

<210> SEQ ID NO 246
<211> LENGTH: 25
<212> TYPE: DNA
<213> ORGANISM: Homo sapiens

<400> SEQUENCE: 246
gagtaacttc ttaaatccct gttct                                    25

<210> SEQ ID NO 247
<211> LENGTH: 25
<212> TYPE: DNA
<213> ORGANISM: Homo sapiens

<400> SEQUENCE: 247
atctctcctg cttggtgatt tcagc                                    25

<210> SEQ ID NO 248
<211> LENGTH: 25
<212> TYPE: DNA
<213> ORGANISM: Homo sapiens

<400> SEQUENCE: 248
cacatcgcct ctggttaaat ctctc                                    25

<210> SEQ ID NO 249
<211> LENGTH: 25
<212> TYPE: DNA
<213> ORGANISM: Homo sapiens

<400> SEQUENCE: 249
cagtcaacta cagctgagtc catag                                    25

<210> SEQ ID NO 250
<211> LENGTH: 25
<212> TYPE: DNA
<213> ORGANISM: Homo sapiens

<400> SEQUENCE: 250
ttcactaacc ttccctaggc attga                                    25

<210> SEQ ID NO 251
<211> LENGTH: 25
<212> TYPE: DNA
<213> ORGANISM: Homo sapiens

<400> SEQUENCE: 251
agaatcactc ctctcaaata tgccc                                    25

<210> SEQ ID NO 252
<211> LENGTH: 25
<212> TYPE: DNA
<213> ORGANISM: Homo sapiens

<400> SEQUENCE: 252
ccatgaagag gtttgccgtc tgggc                                    25

<210> SEQ ID NO 253
<211> LENGTH: 25
<212> TYPE: DNA
<213> ORGANISM: Homo sapiens

<400> SEQUENCE: 253
gagcactgtg tatgactgaa atttc                                    25

<210> SEQ ID NO 254
<211> LENGTH: 25
<212> TYPE: DNA
<213> ORGANISM: Homo sapiens

```
<400> SEQUENCE: 254
caacaacgaa ggactttct ccctg                                          25

<210> SEQ ID NO 255
<211> LENGTH: 25
<212> TYPE: DNA
<213> ORGANISM: Homo sapiens

<400> SEQUENCE: 255
tcactttagc tgtttgcctt actct                                         25

<210> SEQ ID NO 256
<211> LENGTH: 25
<212> TYPE: DNA
<213> ORGANISM: Homo sapiens

<400> SEQUENCE: 256
agaaacttgg atgtcactgc ctgac                                         25

<210> SEQ ID NO 257
<211> LENGTH: 25
<212> TYPE: DNA
<213> ORGANISM: Homo sapiens

<400> SEQUENCE: 257
aagaccatta gaaagcacca ggccg                                         25

<210> SEQ ID NO 258
<211> LENGTH: 25
<212> TYPE: DNA
<213> ORGANISM: Homo sapiens

<400> SEQUENCE: 258
ctactgtgtg tgtgaatgaa cactc                                         25

<210> SEQ ID NO 259
<211> LENGTH: 25
<212> TYPE: DNA
<213> ORGANISM: Homo sapiens

<400> SEQUENCE: 259
ttctacacat ctgcctaact tggga                                         25

<210> SEQ ID NO 260
<211> LENGTH: 25
<212> TYPE: DNA
<213> ORGANISM: Homo sapiens

<400> SEQUENCE: 260
cccccctaat tatccatttt ctgat                                         25

<210> SEQ ID NO 261
<211> LENGTH: 25
<212> TYPE: DNA
<213> ORGANISM: Homo sapiens

<400> SEQUENCE: 261
gttttatgtc cttgttccta atgta                                         25

<210> SEQ ID NO 262
<211> LENGTH: 25
<212> TYPE: DNA
```

```
<213> ORGANISM: Homo sapiens

<400> SEQUENCE: 262 caccectagg aactcagtcc tgtac                                    25

<210> SEQ ID NO 263
<211> LENGTH: 25
<212> TYPE: DNA
<213> ORGANISM: Homo sapiens

<400> SEQUENCE: 263
tgggttcttt gcatgtgggt tccat                                    25

<210> SEQ ID NO 264
<211> LENGTH: 25
<212> TYPE: DNA
<213> ORGANISM: Homo sapiens

<400> SEQUENCE: 264
gctgagcatg aaagctgcct tggaa                                    25

<210> SEQ ID NO 265
<211> LENGTH: 25
<212> TYPE: DNA
<213> ORGANISM: Homo sapiens

<400> SEQUENCE: 265 aacactttt gttatcagtc aatat                                     25

<210> SEQ ID NO 266
<211> LENGTH: 25
<212> TYPE: DNA
<213> ORGANISM: Homo sapiens

<400> SEQUENCE: 266
taaagttcag caacctctgt ccaag                                    25

<210> SEQ ID NO 267
<211> LENGTH: 25
<212> TYPE: DNA
<213> ORGANISM: Homo sapiens

<400> SEQUENCE: 267
gtgacttaat atctattcca tttgt                                    25

<210> SEQ ID NO 268
<211> LENGTH: 25
<212> TYPE: DNA
<213> ORGANISM: Homo sapiens

<400> SEQUENCE: 268
atatggtgct gttctctatg tgttt                                    25

<210> SEQ ID NO 269
<211> LENGTH: 25
<212> TYPE: DNA
<213> ORGANISM: Homo sapiens

<400> SEQUENCE: 269
cttgggtcta aggcatccac gactg                                    25

<210> SEQ ID NO 270
<211> LENGTH: 25
```

```
<212> TYPE: DNA
<213> ORGANISM: Homo sapiens

<400> SEQUENCE: 270
tcaccatctc ttatgttgtt gccgt                                      25

<210> SEQ ID NO 271
<211> LENGTH: 25
<212> TYPE: DNA
<213> ORGANISM: Homo sapiens

<400> SEQUENCE: 271
caagtgggtc ttgtgttgcc agctt                                      25

<210> SEQ ID NO 272
<211> LENGTH: 25
<212> TYPE: DNA
<213> ORGANISM: Homo sapiens

<400> SEQUENCE: 272
tctgtcctcc taagaaatct gccca                                      25

<210> SEQ ID NO 273
<211> LENGTH: 25
<212> TYPE: DNA
<213> ORGANISM: Homo sapiens

<400> SEQUENCE: 273
cactttaacc cacgcttcaa tgaga                                      25

<210> SEQ ID NO 274
<211> LENGTH: 25
<212> TYPE: DNA
<213> ORGANISM: Homo sapiens

<400> SEQUENCE: 274
gcaccccaac gagcaatagc agaga                                      25

<210> SEQ ID NO 275
<211> LENGTH: 25
<212> TYPE: DNA
<213> ORGANISM: Homo sapiens

<400> SEQUENCE: 275
ttctcttacc gccatggagt tcgac                                      25

<210> SEQ ID NO 276
<211> LENGTH: 25
<212> TYPE: DNA
<213> ORGANISM: Homo sapiens

<400> SEQUENCE: 276
cttaatgtct gctctgagcc ttaaa                                      25

<210> SEQ ID NO 277
<211> LENGTH: 25
<212> TYPE: DNA
<213> ORGANISM: Homo sapiens

<400> SEQUENCE: 277
cccttcctca agtggtgcta tttta                                      25

<210> SEQ ID NO 278
```

```
<211> LENGTH: 25
<212> TYPE: DNA
<213> ORGANISM: Homo sapiens

<400> SEQUENCE: 278
ggtacattac tgcaatgttc tctta                                      25

<210> SEQ ID NO 279
<211> LENGTH: 25
<212> TYPE: DNA
<213> ORGANISM: Homo sapiens

<400> SEQUENCE: 279
gtttgcctgt ggtagacacc tgcac                                      25

<210> SEQ ID NO 280
<211> LENGTH: 25
<212> TYPE: DNA
<213> ORGANISM: Homo sapiens

<400> SEQUENCE: 280
aatgcattgc atcaacctac tatag                                      25

<210> SEQ ID NO 281
<211> LENGTH: 25
<212> TYPE: DNA
<213> ORGANISM: Homo sapiens

<400> SEQUENCE: 281
aaaccacaga ctttggcctc agaga                                      25

<210> SEQ ID NO 282
<211> LENGTH: 25
<212> TYPE: DNA
<213> ORGANISM: Homo sapiens

<400> SEQUENCE: 282
ataaagtacc tttgagcatg agtgt                                      25

<210> SEQ ID NO 283
<211> LENGTH: 25
<212> TYPE: DNA
<213> ORGANISM: Homo sapiens

<400> SEQUENCE: 283
ggtccttatt attcttctgt ttatt                                      25

<210> SEQ ID NO 284
<211> LENGTH: 25
<212> TYPE: DNA
<213> ORGANISM: Homo sapiens

<400> SEQUENCE: 284
gactactatg gctgtttaga actac                                      25

<210> SEQ ID NO 285
<211> LENGTH: 25
<212> TYPE: DNA
<213> ORGANISM: Homo sapiens

<400> SEQUENCE: 285
tggaacttca agtaactcct cccag                                      25
```

```
<210> SEQ ID NO 286
<211> LENGTH: 25
<212> TYPE: DNA
<213> ORGANISM: Homo sapiens

<400> SEQUENCE: 286
attcctttct gattggcaca cgtgc                                    25

<210> SEQ ID NO 287
<211> LENGTH: 25
<212> TYPE: DNA
<213> ORGANISM: Homo sapiens

<400> SEQUENCE: 287
actagggaat ttgctcctgt tctgt                                    25

<210> SEQ ID NO 288
<211> LENGTH: 25
<212> TYPE: DNA
<213> ORGANISM: Homo sapiens

<400> SEQUENCE: 288
tgtggtcctg gccaagagct acaat                                    25

<210> SEQ ID NO 289
<211> LENGTH: 25
<212> TYPE: DNA
<213> ORGANISM: Homo sapiens

<400> SEQUENCE: 289
aaagccatgt tgactatttt acagc                                    25

<210> SEQ ID NO 290
<211> LENGTH: 25
<212> TYPE: DNA
<213> ORGANISM: Homo sapiens

<400> SEQUENCE: 290
aaagctcaag aattagcaag actgg                                    25

<210> SEQ ID NO 291
<211> LENGTH: 25
<212> TYPE: DNA
<213> ORGANISM: Homo sapiens

<400> SEQUENCE: 291 tcccccaaact tgctgtcaat tccga                                   25

<210> SEQ ID NO 292
<211> LENGTH: 25
<212> TYPE: DNA
<213> ORGANISM: Homo sapiens

<400> SEQUENCE: 292
gatttcaagc tgttctgaga catct                                    25

<210> SEQ ID NO 293
<211> LENGTH: 25
<212> TYPE: DNA
<213> ORGANISM: Homo sapiens

<400> SEQUENCE: 293
taaacagcca caatcgcatt cagtc                                    25
```

```
<210> SEQ ID NO 294
<211> LENGTH: 25
<212> TYPE: DNA
<213> ORGANISM: Homo sapiens

<400> SEQUENCE: 294
gggagaaact gcatcctaag tggaa                                          25

<210> SEQ ID NO 295
<211> LENGTH: 25
<212> TYPE: DNA
<213> ORGANISM: Homo sapiens

<400> SEQUENCE: 295
tatggttatc cactctgtgt gccaa                                          25

<210> SEQ ID NO 296
<211> LENGTH: 25
<212> TYPE: DNA
<213> ORGANISM: Homo sapiens

<400> SEQUENCE: 296
gaaataccgg cccaagtact gcggt                                          25

<210> SEQ ID NO 297
<211> LENGTH: 25
<212> TYPE: DNA
<213> ORGANISM: Homo sapiens

<400> SEQUENCE: 297
gtaataatgt cttgttttta gccat                                          25

<210> SEQ ID NO 298
<211> LENGTH: 25
<212> TYPE: DNA
<213> ORGANISM: Homo sapiens

<400> SEQUENCE: 298
atttcctttg gagttgcttg cttcc                                          25

<210> SEQ ID NO 299
<211> LENGTH: 25
<212> TYPE: DNA
<213> ORGANISM: Homo sapiens

<400> SEQUENCE: 299
tccaaaagct agtccctact cttta                                          25

<210> SEQ ID NO 300
<211> LENGTH: 25
<212> TYPE: DNA
<213> ORGANISM: Homo sapiens

<400> SEQUENCE: 300
ccatgtttcc tctcaataaa gttcc                                          25

<210> SEQ ID NO 301
<211> LENGTH: 25
<212> TYPE: DNA
<213> ORGANISM: Homo sapiens

<400> SEQUENCE: 301
aagtcccaca gaagctacag ctgcc                                          25
```

<210> SEQ ID NO 302
<211> LENGTH: 25
<212> TYPE: DNA
<213> ORGANISM: Homo sapiens

<400> SEQUENCE: 302
aagacagtgg cccctacaga atgtt                                    25

<210> SEQ ID NO 303
<211> LENGTH: 25
<212> TYPE: DNA
<213> ORGANISM: Homo sapiens

<400> SEQUENCE: 303
gagccgtgac agtggcctgg aaggc                                    25

<210> SEQ ID NO 304
<211> LENGTH: 25
<212> TYPE: DNA
<213> ORGANISM: Homo sapiens

<400> SEQUENCE: 304
aaaacagtcc cttcaaacac acaat                                    25

<210> SEQ ID NO 305
<211> LENGTH: 25
<212> TYPE: DNA
<213> ORGANISM: Homo sapiens

<400> SEQUENCE: 305
gtctccatct cagtacacaa tcatt                                    25

<210> SEQ ID NO 306
<211> LENGTH: 25
<212> TYPE: DNA
<213> ORGANISM: Homo sapiens

<400> SEQUENCE: 306
ctcctctgag gagcttcaag ccaac                                    25

<210> SEQ ID NO 307
<211> LENGTH: 25
<212> TYPE: DNA
<213> ORGANISM: Homo sapiens

<400> SEQUENCE: 307
cgaagcctat atgtgcctgg atcct                                    25

<210> SEQ ID NO 308
<211> LENGTH: 25
<212> TYPE: DNA
<213> ORGANISM: Homo sapiens

<400> SEQUENCE: 308
taagcatcct tagggttctg cctct                                    25

<210> SEQ ID NO 309
<211> LENGTH: 25
<212> TYPE: DNA
<213> ORGANISM: Homo sapiens

<400> SEQUENCE: 309
ctgtctactg caactgtgat ttccc                                              25

<210> SEQ ID NO 310
<211> LENGTH: 25
<212> TYPE: DNA
<213> ORGANISM: Homo sapiens

<400> SEQUENCE: 310
aaagggcaag atctcatttc aattt                                              25

<210> SEQ ID NO 311
<211> LENGTH: 25
<212> TYPE: DNA
<213> ORGANISM: Homo sapiens

<400> SEQUENCE: 311
ctgtggtgac agatccgaaa gcccc                                              25

<210> SEQ ID NO 312
<211> LENGTH: 25
<212> TYPE: DNA
<213> ORGANISM: Homo sapiens

<400> SEQUENCE: 312
tcatcctgca agtgatcagc cgctc                                              25

<210> SEQ ID NO 313
<211> LENGTH: 25
<212> TYPE: DNA
<213> ORGANISM: Homo sapiens

<400> SEQUENCE: 313
taaaacccag tgacctcact tcttt                                              25

<210> SEQ ID NO 314
<211> LENGTH: 25
<212> TYPE: DNA
<213> ORGANISM: Homo sapiens

<400> SEQUENCE: 314
tgctgcaacc gctgtgaatg ctgct                                              25

<210> SEQ ID NO 315
<211> LENGTH: 25
<212> TYPE: DNA
<213> ORGANISM: Homo sapiens

<400> SEQUENCE: 315
tgttctatat ttgcatagcc tttga                                              25

<210> SEQ ID NO 316
<211> LENGTH: 25
<212> TYPE: DNA
<213> ORGANISM: Homo sapiens

<400> SEQUENCE: 316
caaaaaggcc ttatgtcacc actgg                                              25

<210> SEQ ID NO 317
<211> LENGTH: 25
<212> TYPE: DNA
<213> ORGANISM: Homo sapiens

<400> SEQUENCE: 317
ataggtcaat tatatgtctc catta                                          25

<210> SEQ ID NO 318
<211> LENGTH: 25
<212> TYPE: DNA
<213> ORGANISM: Homo sapiens

<400> SEQUENCE: 318
taatcggccc tcagggtttt ctaat                                          25

<210> SEQ ID NO 319
<211> LENGTH: 25
<212> TYPE: DNA
<213> ORGANISM: Homo sapiens

<400> SEQUENCE: 319
tttcacctct agtgatggcc ctact                                          25

<210> SEQ ID NO 320
<211> LENGTH: 25
<212> TYPE: DNA
<213> ORGANISM: Homo sapiens

<400> SEQUENCE: 320
tgcaaagagc ggaccctgga caacc                                          25

<210> SEQ ID NO 321
<211> LENGTH: 25
<212> TYPE: DNA
<213> ORGANISM: Homo sapiens

<400> SEQUENCE: 321
aactgacaag cacactttt tcctc                                           25

<210> SEQ ID NO 322
<211> LENGTH: 25
<212> TYPE: DNA
<213> ORGANISM: Homo sapiens

<400> SEQUENCE: 322
gtggcccctg cagaatgttc atagg                                          25

<210> SEQ ID NO 323
<211> LENGTH: 25
<212> TYPE: DNA
<213> ORGANISM: Homo sapiens

<400> SEQUENCE: 323
tagtcacggt ggtgtcggtg ttgct                                          25

<210> SEQ ID NO 324
<211> LENGTH: 25
<212> TYPE: DNA
<213> ORGANISM: Homo sapiens

<400> SEQUENCE: 324
gagagcacaa catcgaagtc ctgga                                          25

<210> SEQ ID NO 325
<211> LENGTH: 25
<212> TYPE: DNA
<213> ORGANISM: Homo sapiens

```
<400> SEQUENCE: 325
tacacgatgt cctggaccgg agctg                                    25

<210> SEQ ID NO 326
<211> LENGTH: 25
<212> TYPE: DNA
<213> ORGANISM: Homo sapiens

<400> SEQUENCE: 326
caacctttgc actccactgt gcaat                                    25

<210> SEQ ID NO 327
<211> LENGTH: 25
<212> TYPE: DNA
<213> ORGANISM: Homo sapiens

<400> SEQUENCE: 327
tgcagtcata tttccagtct gcctc                                    25

<210> SEQ ID NO 328
<211> LENGTH: 25
<212> TYPE: DNA
<213> ORGANISM: Homo sapiens

<400> SEQUENCE: 328 gtcaccttttt gctgaactca cagtt                                   25

<210> SEQ ID NO 329
<211> LENGTH: 25
<212> TYPE: DNA
<213> ORGANISM: Homo sapiens

<400> SEQUENCE: 329
gccagatggt tgctgccaca acttg                                    25

<210> SEQ ID NO 330
<211> LENGTH: 25
<212> TYPE: DNA
<213> ORGANISM: Homo sapiens

<400> SEQUENCE: 330
accctcttct tgaactggtg ctgtc                                    25

<210> SEQ ID NO 331
<211> LENGTH: 25
<212> TYPE: DNA
<213> ORGANISM: Homo sapiens

<400> SEQUENCE: 331
gatgtcgatg acagacttgc tgaac                                    25

<210> SEQ ID NO 332
<211> LENGTH: 25
<212> TYPE: DNA
<213> ORGANISM: Homo sapiens

<400> SEQUENCE: 332
cagcctgcca taggatccaa ctgga                                    25

<210> SEQ ID NO 333
<211> LENGTH: 25
<212> TYPE: DNA
<213> ORGANISM: Homo sapiens
```

```
<400> SEQUENCE: 333
gtgtttctgt tgcagtggca aaggt                                          25

<210> SEQ ID NO 334
<211> LENGTH: 25
<212> TYPE: DNA
<213> ORGANISM: Homo sapiens

<400> SEQUENCE: 334
aagcatgcgt tgcacttctt ttttg                                          25

<210> SEQ ID NO 335
<211> LENGTH: 25
<212> TYPE: DNA
<213> ORGANISM: Homo sapiens

<400> SEQUENCE: 335
gtctagtgct cttttgctat aaaat                                          25

<210> SEQ ID NO 336
<211> LENGTH: 25
<212> TYPE: DNA
<213> ORGANISM: Homo sapiens

<400> SEQUENCE: 336
tatgttcatc acccttatat catgt                                          25

<210> SEQ ID NO 337
<211> LENGTH: 25
<212> TYPE: DNA
<213> ORGANISM: Homo sapiens

<400> SEQUENCE: 337
aagactctta ggcagctatg ggttt                                          25

<210> SEQ ID NO 338
<211> LENGTH: 25
<212> TYPE: DNA
<213> ORGANISM: Homo sapiens

<400> SEQUENCE: 338
tgttcaagtg cgtgtggcgg tgcta                                          25

<210> SEQ ID NO 339
<211> LENGTH: 25
<212> TYPE: DNA
<213> ORGANISM: Homo sapiens

<400> SEQUENCE: 339
gcttcaggca acttagctgt gtaca                                          25

<210> SEQ ID NO 340
<211> LENGTH: 25
<212> TYPE: DNA
<213> ORGANISM: Homo sapiens

<400> SEQUENCE: 340
gacatactca atcctgattc caagt                                          25

<210> SEQ ID NO 341
<211> LENGTH: 25
<212> TYPE: DNA
```

```
<213> ORGANISM: Homo sapiens

<400> SEQUENCE: 341
agaaagacat actcaatcct gattc                                              25

<210> SEQ ID NO 342
<211> LENGTH: 25
<212> TYPE: DNA
<213> ORGANISM: Homo sapiens

<400> SEQUENCE: 342
acaccagctt atcaaccaac acagc                                              25

<210> SEQ ID NO 343
<211> LENGTH: 25
<212> TYPE: DNA
<213> ORGANISM: Homo sapiens

<400> SEQUENCE: 343
gggtgcatgt tccttaaagg tgcat                                              25

<210> SEQ ID NO 344
<211> LENGTH: 25
<212> TYPE: DNA
<213> ORGANISM: Homo sapiens

<400> SEQUENCE: 344
gctccagaag cgcttggaca ggctg                                              25

<210> SEQ ID NO 345
<211> LENGTH: 25
<212> TYPE: DNA
<213> ORGANISM: Homo sapiens

<400> SEQUENCE: 345
gagggaccat atctactctt gtcat                                              25

<210> SEQ ID NO 346
<211> LENGTH: 25
<212> TYPE: DNA
<213> ORGANISM: Homo sapiens

<400> SEQUENCE: 346
gcaggtgtgc ttagctcttg atagt                                              25

<210> SEQ ID NO 347
<211> LENGTH: 25
<212> TYPE: DNA
<213> ORGANISM: Homo sapiens

<400> SEQUENCE: 347
gaaaataccc catcattcat gctac                                              25

<210> SEQ ID NO 348
<211> LENGTH: 25
<212> TYPE: DNA
<213> ORGANISM: Homo sapiens

<400> SEQUENCE: 348
gaaggcaaac agatcccaga ctcgc                                              25

<210> SEQ ID NO 349
<211> LENGTH: 25
```

```
<212> TYPE: DNA
<213> ORGANISM: Homo sapiens

<400> SEQUENCE: 349
ggtagagact accctagaca tctgc                                    25

<210> SEQ ID NO 350
<211> LENGTH: 25
<212> TYPE: DNA
<213> ORGANISM: Homo sapiens

<400> SEQUENCE: 350
aggttgtgtg ctggagttcc ttcaa                                    25

<210> SEQ ID NO 351
<211> LENGTH: 25
<212> TYPE: DNA
<213> ORGANISM: Homo sapiens

<400> SEQUENCE: 351
acaggaatta ttgccatcac attgg                                    25

<210> SEQ ID NO 352
<211> LENGTH: 25
<212> TYPE: DNA
<213> ORGANISM: Homo sapiens

<400> SEQUENCE: 352
cagtgtagat ggctcttgtt tttgt                                    25

<210> SEQ ID NO 353
<211> LENGTH: 25
<212> TYPE: DNA
<213> ORGANISM: Homo sapiens

<400> SEQUENCE: 353
caatgactcc agatactgcc tgagc                                    25

<210> SEQ ID NO 354
<211> LENGTH: 25
<212> TYPE: DNA
<213> ORGANISM: Homo sapiens

<400> SEQUENCE: 354
aaaaaatcat ctcaccttga gccca                                    25

<210> SEQ ID NO 355
<211> LENGTH: 25
<212> TYPE: DNA
<213> ORGANISM: Homo sapiens

<400> SEQUENCE: 355
atctctatat aactgtcaac accat                                    25

<210> SEQ ID NO 356
<211> LENGTH: 25
<212> TYPE: DNA
<213> ORGANISM: Homo sapiens

<400> SEQUENCE: 356
tgttttgttg cttactcttt agtat                                    25

<210> SEQ ID NO 357
```

```
<211> LENGTH: 25
<212> TYPE: DNA
<213> ORGANISM: Homo sapiens

<400> SEQUENCE: 357
acatcatatt ccttacctct tttgg                                     25

<210> SEQ ID NO 358
<211> LENGTH: 25
<212> TYPE: DNA
<213> ORGANISM: Homo sapiens

<400> SEQUENCE: 358
ggctccaggc tgaggatgag gctga                                     25

<210> SEQ ID NO 359
<211> LENGTH: 25
<212> TYPE: DNA
<213> ORGANISM: Homo sapiens

<400> SEQUENCE: 359
ggctctggaa atctaagttc atact                                     25

<210> SEQ ID NO 360
<211> LENGTH: 25
<212> TYPE: DNA
<213> ORGANISM: Homo sapiens

<400> SEQUENCE: 360
tggtacttat cagtgccaag cgtcc                                     25

<210> SEQ ID NO 361
<211> LENGTH: 25
<212> TYPE: DNA
<213> ORGANISM: Homo sapiens

<400> SEQUENCE: 361
tgttttttac agccaaacct ctgtc                                     25

<210> SEQ ID NO 362
<211> LENGTH: 25
<212> TYPE: DNA
<213> ORGANISM: Homo sapiens

<400> SEQUENCE: 362
gaatagttgt cttttgagcc tcaga                                     25

<210> SEQ ID NO 363
<211> LENGTH: 25
<212> TYPE: DNA
<213> ORGANISM: Homo sapiens

<400> SEQUENCE: 363
ttgagtccgg gtgttcaagg gccaa                                     25

<210> SEQ ID NO 364
<211> LENGTH: 25
<212> TYPE: DNA
<213> ORGANISM: Homo sapiens

<400> SEQUENCE: 364
ccaaggaccc cttatttatc atgcc                                     25
```

```
<210> SEQ ID NO 365
<211> LENGTH: 25
<212> TYPE: DNA
<213> ORGANISM: Homo sapiens

<400> SEQUENCE: 365
agctgaggaa attccgcttc cgaaa                                              25

<210> SEQ ID NO 366
<211> LENGTH: 25
<212> TYPE: DNA
<213> ORGANISM: Homo sapiens

<400> SEQUENCE: 366
tccatcctca aatgactctt ttttc                                              25

<210> SEQ ID NO 367
<211> LENGTH: 25
<212> TYPE: DNA
<213> ORGANISM: Homo sapiens

<400> SEQUENCE: 367
gtgaaatcag ggtgctgtta ccaaa                                              25

<210> SEQ ID NO 368
<211> LENGTH: 25
<212> TYPE: DNA
<213> ORGANISM: Homo sapiens

<400> SEQUENCE: 368
gatggaaagg ctcgctcaat caaga                                              25

<210> SEQ ID NO 369
<211> LENGTH: 25
<212> TYPE: DNA
<213> ORGANISM: Homo sapiens

<400> SEQUENCE: 369
atccacagac ggacgtcttc ctcat                                              25

<210> SEQ ID NO 370
<211> LENGTH: 25
<212> TYPE: DNA
<213> ORGANISM: Homo sapiens

<400> SEQUENCE: 370
tactgcctca tgtaaagact cttgc                                              25

<210> SEQ ID NO 371
<211> LENGTH: 25
<212> TYPE: DNA
<213> ORGANISM: Homo sapiens

<400> SEQUENCE: 371
acttcatttt cttagcgttt ctgga                                              25

<210> SEQ ID NO 372
<211> LENGTH: 25
<212> TYPE: DNA
<213> ORGANISM: Homo sapiens

<400> SEQUENCE: 372
ctgatgtgtc cccaaaactga tttaa                                             25
```

<210> SEQ ID NO 373
<211> LENGTH: 25
<212> TYPE: DNA
<213> ORGANISM: Homo sapiens

<400> SEQUENCE: 373
tgtaacacat agtggcttct ccgcc                               25

<210> SEQ ID NO 374
<211> LENGTH: 25
<212> TYPE: DNA
<213> ORGANISM: Homo sapiens

<400> SEQUENCE: 374
gctaacccag tatgttcttc ttttt                               25

<210> SEQ ID NO 375
<211> LENGTH: 25
<212> TYPE: DNA
<213> ORGANISM: Homo sapiens

<400> SEQUENCE: 375
ctccttgact ccttgtggtt tatgt                               25

<210> SEQ ID NO 376
<211> LENGTH: 25
<212> TYPE: DNA
<213> ORGANISM: Homo sapiens

<400> SEQUENCE: 376
tgagccctga cagatgccgt atttc                               25

<210> SEQ ID NO 377
<211> LENGTH: 25
<212> TYPE: DNA
<213> ORGANISM: Homo sapiens

<400> SEQUENCE: 377
acattgaccc acaggacatt gtaaa                               25

<210> SEQ ID NO 378
<211> LENGTH: 25
<212> TYPE: DNA
<213> ORGANISM: Homo sapiens

<400> SEQUENCE: 378
gcatttagtc caatgtcttt ttaag                               25

<210> SEQ ID NO 379
<211> LENGTH: 25
<212> TYPE: DNA
<213> ORGANISM: Homo sapiens

<400> SEQUENCE: 379
agaaagcatt accagtcacc tactc                               25

<210> SEQ ID NO 380
<211> LENGTH: 25
<212> TYPE: DNA
<213> ORGANISM: Homo sapiens

<400> SEQUENCE: 380
tgtgggagtc ttgggtactc gcacc                               25

<210> SEQ ID NO 381
<211> LENGTH: 25
<212> TYPE: DNA
<213> ORGANISM: Homo sapiens

<400> SEQUENCE: 381
cctcctgcgt caatgccatg gaagg                                   25

<210> SEQ ID NO 382
<211> LENGTH: 25
<212> TYPE: DNA
<213> ORGANISM: Homo sapiens

<400> SEQUENCE: 382
atacggtgat tcctgttctt ggctt                                   25

<210> SEQ ID NO 383
<211> LENGTH: 25
<212> TYPE: DNA
<213> ORGANISM: Homo sapiens

<400> SEQUENCE: 383
ctcgcccgtc acaaagagct tcaac                                   25

<210> SEQ ID NO 384
<211> LENGTH: 25
<212> TYPE: DNA
<213> ORGANISM: Homo sapiens

<400> SEQUENCE: 384
aatgaggaaa ctccaaacct cctgt                                   25

<210> SEQ ID NO 385
<211> LENGTH: 25
<212> TYPE: DNA
<213> ORGANISM: Homo sapiens

<400> SEQUENCE: 385
tatcttaaac ccacataaac acttc                                   25

<210> SEQ ID NO 386
<211> LENGTH: 25
<212> TYPE: DNA
<213> ORGANISM: Homo sapiens

<400> SEQUENCE: 386
agcacattcc ttttgcaggt ctgag                                   25

<210> SEQ ID NO 387
<211> LENGTH: 25
<212> TYPE: DNA
<213> ORGANISM: Homo sapiens

<400> SEQUENCE: 387
acgttgtcac cggagcactg aagat                                   25

<210> SEQ ID NO 388
<211> LENGTH: 25
<212> TYPE: DNA
<213> ORGANISM: Homo sapiens

<400> SEQUENCE: 388
ggaacacatt agtctatggg acctt                                    25

<210> SEQ ID NO 389
<211> LENGTH: 25
<212> TYPE: DNA
<213> ORGANISM: Homo sapiens

<400> SEQUENCE: 389
gtatttggga ctgaattgca ctaag                                    25

<210> SEQ ID NO 390
<211> LENGTH: 25
<212> TYPE: DNA
<213> ORGANISM: Homo sapiens

<400> SEQUENCE: 390
tgtccccctt gtggaaccaa atgta                                    25

<210> SEQ ID NO 391
<211> LENGTH: 25
<212> TYPE: DNA
<213> ORGANISM: Homo sapiens

<400> SEQUENCE: 391
gaattctccc agcgttaaca caaaa                                    25

<210> SEQ ID NO 392
<211> LENGTH: 25
<212> TYPE: DNA
<213> ORGANISM: Homo sapiens

<400> SEQUENCE: 392
tgctcagtac agccaccttg gagga                                    25

<210> SEQ ID NO 393
<211> LENGTH: 25
<212> TYPE: DNA
<213> ORGANISM: Homo sapiens

<400> SEQUENCE: 393
gttttcatga actagcaacc ccacc                                    25

<210> SEQ ID NO 394
<211> LENGTH: 25
<212> TYPE: DNA
<213> ORGANISM: Homo sapiens

<400> SEQUENCE: 394
ctcgcccgtc acaaagagct tcaac                                    25

<210> SEQ ID NO 395
<211> LENGTH: 25
<212> TYPE: DNA
<213> ORGANISM: Homo sapiens

<400> SEQUENCE: 395
aaatctggaa ctgcctctgt tgtgt                                    25

<210> SEQ ID NO 396
<211> LENGTH: 25
<212> TYPE: DNA
<213> ORGANISM: Homo sapiens

<400> SEQUENCE: 396

```
gtatctctaa cattccaaat tactg                                          25

<210> SEQ ID NO 397
<211> LENGTH: 25
<212> TYPE: DNA
<213> ORGANISM: Homo sapiens

<400> SEQUENCE: 397
ccctagccta gggtcccata ttggg                                          25

<210> SEQ ID NO 398
<211> LENGTH: 25
<212> TYPE: DNA
<213> ORGANISM: Homo sapiens

<400> SEQUENCE: 398
gtaatggtgg actaattgct gtata                                          25

<210> SEQ ID NO 399
<211> LENGTH: 25
<212> TYPE: DNA
<213> ORGANISM: Homo sapiens

<400> SEQUENCE: 399
gtgcaacttg agggacgact ttctt                                          25

<210> SEQ ID NO 400
<211> LENGTH: 25
<212> TYPE: DNA
<213> ORGANISM: Homo sapiens

<400> SEQUENCE: 400
tcatccatct cagcatcaac acaat                                          25
```